US008569230B2

(12) United States Patent
Yount et al.

(10) Patent No.: US 8,569,230 B2
(45) Date of Patent: Oct. 29, 2013

(54) ANTIMICROBIAL KINOCIDIN COMPOSITIONS AND METHODS OF USE

(75) Inventors: Nannette I. Yount, San Juan Capistrano, CA (US); Michael Yeaman, Redondo Beach, CA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 0 days.

(21) Appl. No.: 13/101,935

(22) Filed: May 5, 2011

(65) Prior Publication Data

US 2011/0319319 A1 Dec. 29, 2011

Related U.S. Application Data

(63) Continuation of application No. 12/438,923, filed as application No. PCT/US2007/014499 on Jun. 20, 2007, now abandoned.

(60) Provisional application No. 60/815,491, filed on Jun. 20, 2006.

(51) Int. Cl.
| | | |
|---|---|---|
| A01N 37/18 | (2006.01) |
| A61K 38/00 | (2006.01) |
| A61K 38/04 | (2006.01) |
| A61P 31/00 | (2006.01) |
| C07K 5/00 | (2006.01) |
| C07K 7/00 | (2006.01) |
| C07K 16/00 | (2006.01) |
| C07K 17/00 | (2006.01) |

(52) U.S. Cl.
USPC ............. 514/2.3; 530/324; 530/325; 530/326

(58) Field of Classification Search
None
See application file for complete search history.

(56) References Cited

U.S. PATENT DOCUMENTS 7,091,310 B2 * 8/2006 Merzouk et al. ............... 530/300
2004/0197303 A1 * 10/2004 Merzouk et al. ............. 424/85.1

FOREIGN PATENT DOCUMENTS

WO  WO 2005/066205  7/2005

OTHER PUBLICATIONS

Bjorstad et al., (Antimicrob Agents Chemother. Sep. 2005;49(9):3889-95).*
Yount et al., (PNAS USA. May 11, 2004;101(19):7363-8. Epub Apr. 26, 2004).*
UniProt/SwissProt P10145 IL-8_Human (Mar. 1, 1989).*
Anonymous, "Chemokine/Chemokine Receptor Nomenclature," J. Leukoc Biol., 70:465-466 (2001).
Bauer et al., "Structure determination of human and murine β-defensins reveals structural conservation in the absence of significant sequence similarity," Protein Sci., 10:2470-2479 (2001).
Bevins et al., "Human Enteric Defensin Genes: Chomosomal Map Position and a Model for Possible Evolutionary Relationships," Genomics, 31:95-106 (1996).

(Continued)

*Primary Examiner* — Cherie M Stanfield
(74) *Attorney, Agent, or Firm* — Jones Day

(57) ABSTRACT

The present invention provides novel kinocidin peptides comprising a C-terminal portion of a kinocidin, wherein the C-terminal portion encompasses an α-helical secondary structure and further displays antimicrobial activity. The kinocidin peptides of the invention are derived from and correspond to a C-terminal portion of a kinocidin that includes a $\gamma_{KC}$ core and that can be a CXC, CC, or C class chemokine. Structural, physicochemical and functional properties of this novel class of antimicrobial peptides and amino acid sequences of particular kinocidin peptides are also disclosed. The invention also provides related antimicrobial methods.

20 Claims, 26 Drawing Sheets

(56) References Cited

OTHER PUBLICATIONS

Bjorstad et al., "Interleukin-8-derived peptide has antibacterial activity," Antimicrobial Agents and Chemotherapy, 49(9):3889-3895 (2005).
Blaser, M.J., "Clinical Implications of Basic Research," N. Engl. J. Med., 346:2083-2085 (2002).
Bontems et al., "Analysis of Side-Chain Organization on a Refined Model of Charybdotoxin: Structural and Functional Implications," Biochemistry, 31:7756-7764 (1992).
Bruix et al., "Solution Stucture y1-H and y1-P Thionins from Barley and Wheat Endosperm Determined by H-NMR: A Structural Motif Common to Toxic Arthropod Proteins," Biochemistry, 32:715-724 (1993).
Caldwell et al., "Solution structure of the thermostable sweet-tasting protein brazzein," Nat. Struct. Biol., 5:427-431 (1998).
Campos-Olivas et al., "NMR Solution Structure of the Anitfungal Protein form *Aspergillus giganteus*: Evidence for Cysteine Pairing Isomerism," Biochemistry, 34:3009-3021 (1995).
Charlet et al., "Innate Immunity, Isolation of Several Cysteine-Rich Antimicrobial Peptides From the Blood of a Mollusc, *Mytilus edulis*" J. Biol. Chem., 271:21808-212813 (1996).
Clore et al., "Three-Dimensional Structure of Interleukin 8 in Solution," Biochemistry, 29:1689-1696 (1990).
Cole et al., "Cutting Edge: IFN-Inducible ELE CXC Chemokines Display Defensin-Like Antimicrobial Activity," J. Immunol., 167:623-627 (2001).
Dauter et al., "Atomic Resolution (0.94 A) Structure of *Clostridium acidurici* Ferredoxin, Detailed Geometry of [4Fe-4S] Clusters in a Protein," Biochemistry, 36:16065-10673(1997).
Fahrner et al., "Solution structure of protegrin-1, a broad spectrum antimicrobial peptide from porcine leukocytes," Chem. Biol., 3:543-550 (1996).
Fant et al., "Determination of the Three-dimensional Solution Structure of *Rapanus sativus* Antifungal Protein 1 by H NMR," J. Mol. Biol., 279:257-270 (1998).
Fant et al., "The Three-Dimensional Solution Structure of *Aesculus hippocastanum* Antimicrobial Protein 1 Determined by H Nuclear Magnetic Resonance," Proteins, 37:388-403 (1999).
Ganz, "Versatile Defensins," Science, 298:977-978 (2002).
Gesell et al., "Two-dimensional H NMR experiments show that the 23-residue magainin antibiotic peptide is an α-helix in dodecylphosphocholine micelles, sodium dodecylsulfate micelles, and trifluoroethanol/water solution," J. Biomol. NMR, 9:127-135 (1997).
Gudmundsson et al., "Structure of the gene for porcine peptide antibiotic PR-39, a cathelin gene family member: Comparative mapping of the locus for the human peptide antibiotic FALL-39," Proc. Natl. Acad. Sci. USA, 92:7085-7089 (1995).
Hanzawa et al., "H nuclear magnetic resonance study of the solution conformation of an antibacterial protein, sapecin," FEBS Lett., 269:413-420 (1990).
Harvey et al., "The solution structure of human transforming growth factor α," Eur. J. Biochem., 198:555-562 (1991).
Hill et al., "Crystal Stuctural of Defensin HNP-3, an Amphiphilic Dimer: Mechanisms of Membrane Permeabilizations," Science, 251:1481-1485 (1991).
Hoffman et al., "Multiple control of interleukin-8 gene expression," J. Leukoc. Biol., 72:847-855 (2002).
Hughes, A.L., "Evolutionary diversification of the mammalian defensins," Cell. Mol. Life Sci., 56:94-103 (1999).
Krijgsveld et al., "Thrombocidins, Microbicidal Proteins from Human Blood Platelets, Are C-terminal Deletion Products of CXC Chemokines," J. Biol. Chem., 275:20374-20381 (2000).
Laederach et al., "Solution and Micelle-Bound Structures of Tachyplesin I and Its Active Aromatic Linear Derivatives," Biochem., 41:12359-12368 (2002).
Landon et al., "Solution structure of drosomycin, the first inducible antifungal protein from insects," Protein Sci., 6:1878-1884 (1997).

Lehrer et al.., "Interaction of Human Defensins with *Escherichia coli*," J. Clin. Invest., 84:553-561 (1989).
Mandard et al., "Solution structure of thanatin, a potent bactericidal and fungicidal insect peptide, deteremined from proton two-dimensional nuclear magnetic resonance data," Eur. J. Biochem., 256:404-410 (1998).
Mandard et al., "The solution structure of gomesin, an antimicrobial cysteine-rich peptide from the spider," Eur. J. Biochem., 269:1190-1198 (2002).
Melo et al., "Inhibition of Trypsin by Cowpea Thionin: Characterization, Molecular Modeling, and Docking," Proteins, 48:311-319 (2002).
Metzler et al., "Determination of the Three-Dimensional Solution Structure of Ragweed Allergen Amb t V by Nuclear Magnetic Resonance Spectroscopy," Biochemistry, 31:5117-5127 (1992).
Mezzano et al., "Glomerular Localization of Platelet Factor 4 in Streptococcal Nephritis," Nephron., 61:58-63 (1992).
Moller et al., "Chemokine Patterns in Meningococcal Disease," J. Infect. Dis., 191:768-775 (2005).
Nakamura et al., Tachyplesin, a Class of Antimicrobial Peptide fromt he Hemocytes of the Horseshoe Crab (*Tachypleus tridentatus*) J. Biol. Chem., 263:16709-16713 (1988).
Nei et al., "Estimation of divergence times from multiprotein sequences for a few mammalian species and several distantly related organisms," Proc. Natl. Acad. Sci. USA, 98:2497-2502 (2001).
Nibbering et al., "Tc-Labeled UBI 29-41 Peptide for Monitoring the Efficacy of Antibacterial Agents in Mice Infected with *Staphylococcus aureus*," J. Nucl. Med., 45:321-326 (2004).
P10145 (IL8_Human) Mar. 6, 2013, Version 158, UniProtKB/Swiss Port, [>database < online]. UniProt/SwissProt P10145 IL-8_Human (1989) [retrieved on Mar. 28, 2013]. Retrieved from: UniProtKB/Swiss-Prot IL8_Human.
Park et al., "Antimicrobial Peptides from the Skin of a Korean Frog," Biochem. Biophys. Res. Commun., 205:948-954 (1994).
Peterson et al., "3D solution structure of copper and silver-substituted yeast metallothioneins," FEBS Lett., 379:85-93 (1996).
Qiu et al., "Chemokine Expression Dynamics in Mycobacterial (Type-1) and Schistosomal (Type-2) Antigen-Elicited Pulmonary Granuloma Formation," Am. J. Pathol., 158:1503-1515 (2001).
Sallenave, J. M., "Antimicrobial Activity of Antiproteinases," Biochem. Soc. Trans., 30:111-115 (2002).
Silva et al., "Isolation and Characterization of Gomesin, an 18-Residue Cysteine-Rich Defense Peptide from Spider *Acanthoscurria gomesiana* Hemocytes with Sequence Similarities to Horseshoe Crab Antimicrobial Peptides of the Tachyplesin Family," J. Biol. Chem., 275:33464-33470 (2000).
Tang et al., "Antimicrobial Peptides from Human Platelets," Infect. Immun., 70:6524-6533 (2002).
Uematsu et al., "Polar Angle as a Determinant of Amphipathic α-Helix-Lipid Interactions: A Model Peptide Study," Biophys. J., 79:2075-2083 (2000).
Walz et al., "Purification and Amino Acid Sequencing of NAF, A Novel Neutrophil-Activating Factor Produced by Monocytes," Biochem. Biophys. Res. Commun., 149:755-761 (1987).
White et al., "Structure, function, and membrane integration of defensins," Curr. Opin. Struct. Biol., 5:521-527 (1995).
Wieprecht et al., "Peptide Hydrophobicity Controls the Activity and Selectivity of Magainin 2 Amide in Interaction wit Membranes," Biochemistry, 36:6124-6132 (1997).
Wijaya et al., "Defense proteins from seed of *Cassia fistula* include a lipid transfer protein homologue and a protease inhibitory plant defensin," Plant Sci., 159:243-255 (2000).
Yang et al., "Many chemokines including CCL20/MIP-3α display antimicrobial activity," J. Leukoc. Biol., 74:448-455 (2003).
Yang et al., "Solution Structure and Activity of the Synthetic Four-Disulfide Bond Mediterranean Mussel Defensin (MGD-1)" Biochemistry, 39:14436-14447 (2000).
Yeaman et al., "Code among chaos: Immunorelativity and the AEGIS Model of Antimicrobial Peptides," ASM News, 71:21-27 (2005).
Yeaman et al., "Mechanisms of Antimicrobial Peptide Action Resistane," Pharmacol. Rev., 55:27-55 (2003).
Yeaman et al., "Purification and In Vitro Activities of Rabbit Platelet Microbicidal Proteins," Infect. Immun., 65:1023-1031 (1997).

(56) References Cited

OTHER PUBLICATIONS

Yeaman et al., "Synthetic Peptides That Exert Antimicrobial Activities in Whole Blood and Blood-Derived Matrices," Antimicrob. Agents Chemother., 46:3883-3891 (2002).

Yeaman, Clin. "The Role of Platelets in Antimicrobial Host Defense," Infect. Dis., 25:951-970 (1997).

Yoshimura et al., "Purification of a human monocyte-derived neutrophil chemotactic factor that has peptide sequence similarity to other host defense cytokines," Proc. Natl. Acad. Sci. USA, 84:9233-9237 (1987).

Yount et al., "Advances in antimicrobial peptide immunobiology," Biopolymers, 84(5):435-458 (2006).

Yount et al., "Cloning and Expression of Bovine Neutrophil β-Defensins," J. Biol. Chem., 274:2624926258 (1999).

Yount et al., "Modular determinants of antimicrobial activity in platelet factor-4 family kinocidins," Biochimica et Biophysica Acta 1768:609-619 (2007).

Yount et al., "Multidimensional signatures in antimicrobial peptides," Proc. Natl. Acad. Sci. USA, 101:7363-7368 (2004).

Yount et al., "Platelet Microbicidal Protein 1: Structural Themes of a Multifunctional Antimicrobial Peptide," Antimicrob. Agents Chemother., 48:4395-4404 (2004).

Yount et al., "Structural congruence among membrane-active host defense polypeptides of diverse phylogeny," Biochimica Et Biophysica Acta, 1758 (9):1373-1386 (2006).

Yount et al., "Structural correlates of antimicrobial efficacy in IL-8 and related human kinocidins," Biochimica et Biophysica Acta, 1768:598-608 (2007).

\* cited by examiner

| Sequence Formula | $[X_{n1}]$ 'G/X C | $(X_{n3})$ | C $[X_{n4}]$ C | Peptide Family | Representative |
|---|---|---|---|---|---|
| DCYCRIPACIAGE- | RRYQTCIYQGRLWAFC | | C | α Defensins | HNP-3 (*Homo*) |
| EPVSCIRNGGICQ-YRC- | IGLRHKIGTCGSP | ----F KC | C K | β Defensins | mBD-8 (*Mus*) |
| ATCDLLSGTGINHSACA-AHC-LLRG | NRGGYCNGK | ----GVC | V CRN | Insect defensins | Phormicin (*Protophormia*) |
| DCLSGRYKGPCAVWDNETCR-RVC-KEEG | RSSGHCSPS | ----LKC | W CEGC | Insect CS-αβ | Drosomycin (*Drosophila*) |
| CNERPSQTWSGNCGNTAHC-DKQCQDWEK | ASHGACHKR-ENHWKC | F | CYFNC | Plant CS-αβ | Ah-AMP-1 (*Aesculus*) |
| GFGCPNNYQC-HRHCKSIPG | RCGGYCGGWH--RLRC | T | CYRCG | Crustacea CS-αβ | MGD-1 (*Mytilus*) |
| | -RGVCVCF---RRRC | Y | CLRGGR | *levo*-Protegrin | Protegrin-1 (*Sus*) |
| GRFCKCYCRGRFSASAWGK | CRR'GACKAKC---RSAC | Q | - | *levo*-Mytilin | Mytilin A (*Mytilus*) |
| SLFSLIKAGAKFLGKNL | LKQGACY------AAC | K | ASKQC | Gaegurin | Gaegurin-1 (*Rana*) |
| | -RGRCY-TVCRQKYC | L | RRC | *levo*-Gomesin | Gomesin (*Acanthoscurria*) |
| | MRGCKOTR-----RNC | Y | IIPVPKKSG | *levo*-Thanatin | Thanatin (*Podisus*) |
| RC | RRYCI-GRY---CVRFC | W | K | *levo*-Tachyplesin | Tachyplesin-1 (*Tachypleus*) |
| | CYCKGKYSD---FEC | K | AGDRPCKKVYCK... | *levo*-AFP-1 | AFP-1 (*Aspergillus*) |
| | γ-core Signature | | | | |

FIG. 2 B

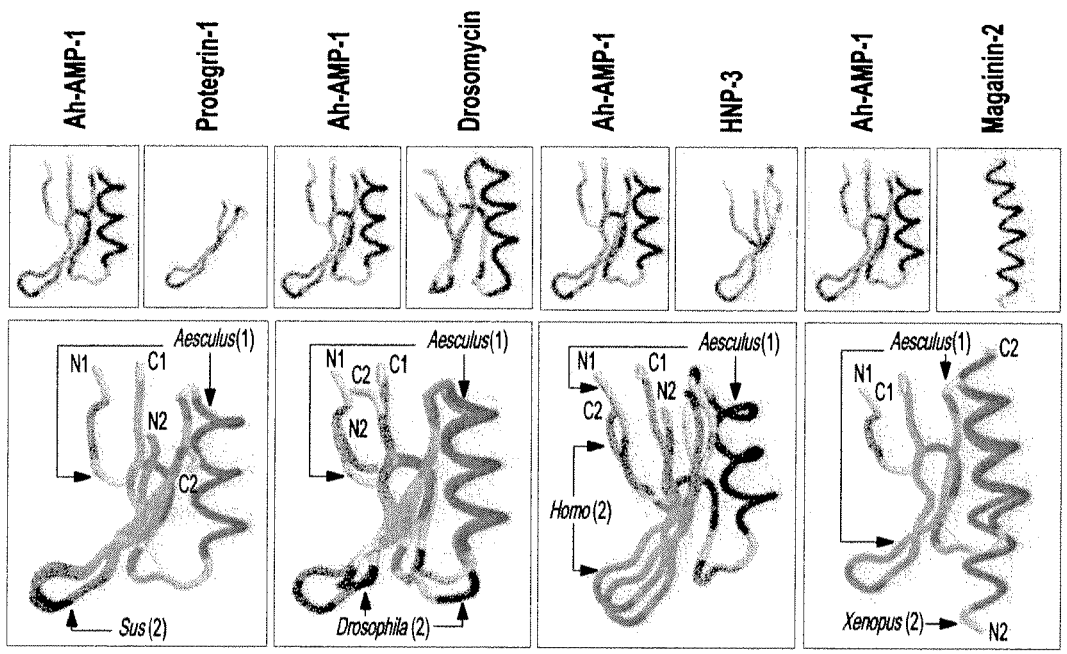
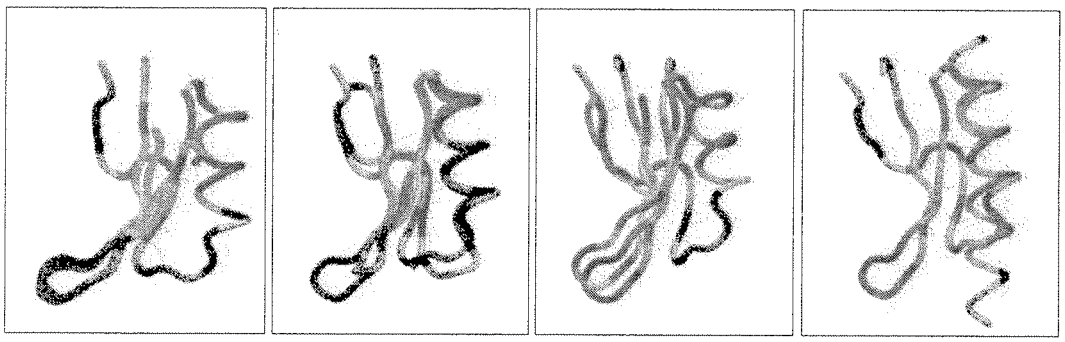
FIG. 3A  FIG. 3C  FIG. 3E  FIG. 3G
FIG. 3B  FIG. 3D  FIG. 3F  FIG. 3H

γ-Group

| Molecule (Source) | γ-Core Sequence | 3D Structure |
|---|---|---|
| Protegrin (Pig; *Sus*) | RGVCVCFRRRCYCLRGGR | |
| Gomesin (Spider, *Acanthoscurria*) | RGRCYTVCRQKYCLRRC | |
| Tachyplesin-1 (Horseshoe crab; *Tachypleus*) | RCRRYCIGRYCVRFCWK | |
| RTD-1 (Rhesus macaque; *Macaca*) | CICRCVGRRCLCRC | |
| Thanatin (Soldier bug; *Podisus*) | RQCKGTRRNCYI | |
| Hepcidin (Human; *Homo*) | CIFCCGCCHRSKCGMCC | |

γ–α Group

| Molecule (Source) | γ-Core Sequence | 3D Structure |
|---|---|---|
| Sapecin (Flesh fly; *Sarcophage*) | RGGYCNGKAVCVCRN | |
| Insect defensin A (Flesh fly; *Protophormia*) | RGGYCNGKGVCVCRN | |
| Heliomycin (Tobacco budworm; *Heliothis*) | KGGHCGSFANVNCWCET | |
| Drosomycin (Friut fly; *Drosophila*) | SSGHCSPSLKCWCEGC | |
| MGD-1 (Mussel; *Mytilus*) | RCGGYCGGWHRLRCTCYRCG | |
| Charybdotoxin (Scorpion; *Leiurus*) | SRGKCMNKKCRCYS | |

β–γ Group

| Molecule (Source) | γ-Core Sequence | 3D Structure |
|---|---|---|
| HNP-3 (Human; *Homo*) | RYGTCIYQGRLWAFCC | |
| RK-1 (Rabbit; *Oryctolagus*) | EVIDGSCGLFNSKYICCREK | |
| BNBD-12 (Cow; *Bos*) | MRQIGTCFGRPVKCCRSW | |
| HBD-1 (Human; *Homo*) | KIQGTCYRGKAKCCK | |
| HBD-2 (Human; *Homo*) | RYKQIGTCGLPGTKCCKKP | |
| mBD-8 (Mouse; *Mus*) | HKIGTCGSPFKCCK | |

β–γ–α Group

| Molecule (Source) | γ-Core Sequence | 3D Structure |
|---|---|---|
| Ah-AMP-1 (Horse chestnut; *Aesculus*) | SHGACHKRENHWKCFCYFNC | |
| Rs-AFP-1 (Radish; *Raphanus*) | RHGSCNYVFPAHKCICYFPC | |
| Ps-defensin-1 (Pea; *Pisum*) | ISGTCHNWKCFCTQNC | |
| G-1-H-thionin (Barley; *Hordeum*) | GGGNCDGPLRRCKCMRRC | |
| G-1-P-thionin (Wheat; *Triticum*) | GGGNCDGPFRRCKCIRQC | |
| Brazzein (J'oublie; *Pentadiplandra*) | RSGECFYDEKRNLQCICDY | |

FIG. 4

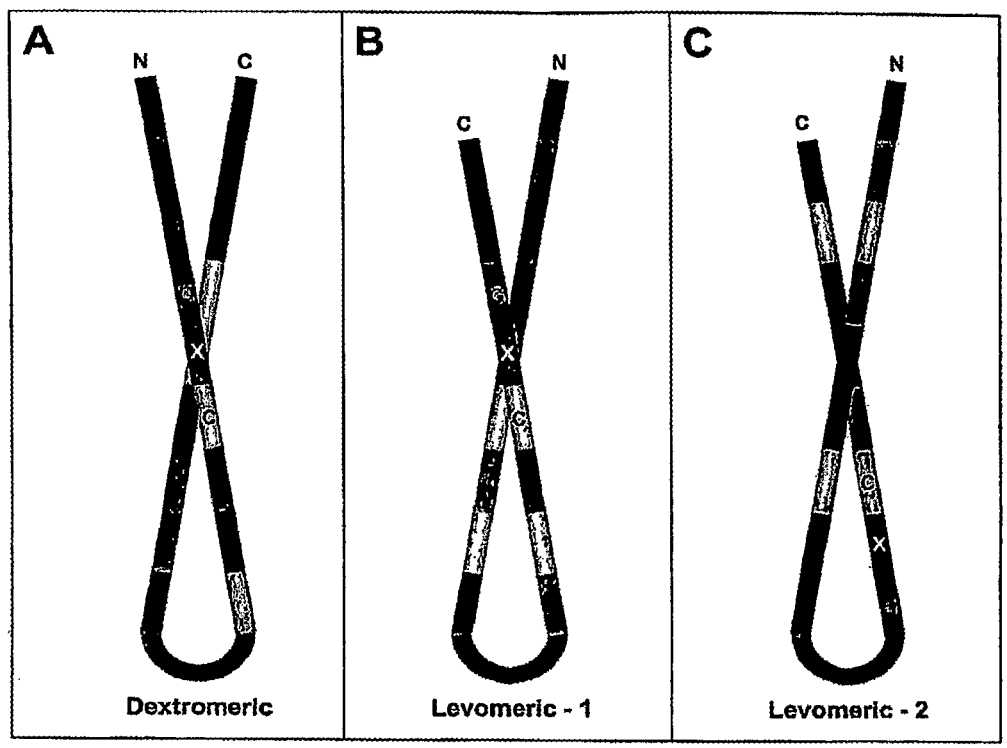
FIG. 5 A-C

Brazzein

Charybdotoxin

Tachyplesin

Brazzein

Charybdotoxin

Tachyplesin

Brazzein

Charybdotoxin

Tachyplesin

| Sequence | TOXIN CLASS | Database Code(s) | RMSD |
|---|---|---|---|
| 1 | KEGYLVKKSDGCKVGCLKLGENEGCDTECKAKNQGGEYGYCYAFACWCEGLPESTPTVPLPNKSC | gi|494834|pdb|2BN2| | -1 |
| 2 | MKKNGYPLDRNGXTTECEGVNAMAPHVCNEECTKVYYAESGYCCWGACYCFGLEDDKPIGPMKDITKKYCDVQIIPS | gi|4140001|pdb|1BCG| | 1.1 |
| 3 | VRDAYIAKPENCVYHCAGNEGCNKLCTDNGAESGYCQWGGRYGNACWCIKLPDDVPIRVPGKCH | gi|17368154|sp|P56329|SCX4_MESMA | 1.1 |
| 4 | ASCRTPKDCADPCRKETGCPYGKCMNRKCKCNRC | gi|37037299|sp|P59557|SCK1_HETSP | 1.2 |
| 5 | KKOGYPVDSGNCKYECLKDDYCNDLCLERKADKGYCYWGKVSCYCYGLPDNSPTKTSGKCNPA | gi|999885|pdb|1NRA| | 1.2 |
| 6 | MNYLVMISPALLLMTGVESVRDAYIAKPHNCVYECARNEYCNDLCTKNGAKSGYCQWVGKYGNGCWCIELFDNVPIRVPGKCHR | gi|6094252|sp|P45607|SCX1_MESMA | 1.3 |
| 7 | VRINAKCRGSPECLPKCKEAIGKAAGKCMNGKCKCYP | gi|1173382|sp|P46114|SCKA_TITSE | 1.5 |
| 8 | XFTQESGTASNGCWBICKRLHNTNRGKCMNRKCRCYS | gi|3315925|pdb|1LJR| | 1.5 |
| 9 | VRDAYIAQPENCVYHCFPGSGGCDTLCKEKGGTSGHCGFKVGHGLAGWCNALPDNVGIIVEGEKCHSX | gi|4930278|pdb|1BMR| | 1.8 |
| 10 | GVEINVKCSGSPQCLKPCKDAGMRFGKCMNRKCHCTPK | gi|2392702|pdb|2KTX| | 1.8 |

FIG. 11 B

| Sequence | PROTEASE INHIBITOR CLASS | Database Code(s) | RMSD |
|---|---|---|---|
| 36 | XPEIEADGNECLKEYDGDVGFGFCAPRFPTICYTRCRBNKGAKGGRCRWGQGSNVKCLCDPCGDTPQ | gi|25373448|pdb|1JXCIA | 3.5 |
| 37 | RVCPRILLECKKDSDCLAECVCLEHGYCG | gi|23320036|pdb|1LUO|A | 3.2 |
| 38 | AHMDCTEFNPLCRCNSKMLGDLICAVIGDAKEEHRNMCALCCEHPCGFEVBNGPCE | gi|23200155|pdb|1IW4|A | 4.2 |
| 39 | CIPKWNRCGPKMDGVPCCEPYTGTSDYYGNCS | gi|15826209|pdb|1HTXQA | 4 |
| 40 | GCPRILMRCKQDSDCLAGCVGGPNGFCG | gi|230422|pdb|2ETI| | 3.6 |
| 41 | RVCPRILMECKKDSDCLAECVCLEHGYCG | gi|29775|pdb|1CTI| | 3.3 |
| 42 | XGSDGGVCPKILKKCRRDSDCPGACICRGNGYCG | gi|14270521|pdb|1HA9|A | 3.1 |

| Sequence | OTHER CLASS | Database Code(s) | RMSD |
|---|---|---|---|
| 43 | NLMKRCTRGFRKLGKCTTLEEERCKTLYPRGQCTCSDSKMNTHSCDCKSC | gi|37028170|pdb|1UGL|A | |
| 44 | ADCNGACSPFEVPPCRSRDCRCVPIGLFVGFCIHPTG | gi|33357101|pdb|1JU8|A | |
| 45 | KSCCRNTLARNCYNACRFTGGSQPTCGILCDCIHVTTTCPSSHPS | gi|29726000|pdb|1NBL|A | 4.5 |
| 46 | XTTGPCCRQCKLKPAGTTGWKTSLTSHYCTGKSCDCPLYPG | gi|26946558|pdb|1MFZ|A | 4.5 |
| 47 | RKGHFSRCPKQYKHYCIKGRCRFVVAEQTPSCVCDEGYIGARCERVDLFY | gi|22216780|pdb|1IPO|A | 4.2 |
| 48 | XGLPVCGETCVGGTCNTPGCTCSWPVCTR | gi|21730326|pdb|1JJZ|A | 3.3 |
| 49 | XNFNGGCLAGYMRTADGRCKPTF | gi|6730059|pdb|1B1V|A | 2.7 |
| 50 | ENFSGGCVAGYMRTPDGRCKPTFYQ | gi|6729396|pdb|1B0F|A | 2.9 |
| 51 | PIEVNDDCMACEAOVEICPDVFEMNEEGDKAVVINPDSDLDCVEEAIDSCPAEAIVRS | gi|8137634|pdb|1F2G| | 6 |
| 52 | XCLGDKCDYNNGCCSGYVCSRTWKWCVLAGPW | gi|15022308|pdb|1CK7|A | 2.6 |
| 53 | TQGNTCGGETCSAAQVCLKGKCVCNEVHCRIRCKYGLKKDENGCEYPCSCAKASQ | gi|4829933|pdb|1BX7| | 6.5 |
| 54 | XDKCKKVYENYPVSKCQLANGCNYDCKLDKHARSGECFYDEKRNLQCICDYCEY | gi|3318668|pdb|1BRZ| | 3 |
| 55 | TTCCPSIVARSNFNVCRLPGT5EAICATYTGCIIPGATCPGDYAN | gi|2392042|pdb|1AB1| | 8.1 |
| 56 | XVYTDGTESGQNLCLCEEGSNVCGQGNKCILGSDGEKNOCVTGEGTPKPQSH | gi|1431745|pdb|1HIC| | 4.2 |
| 57 | TCEICAYAACTGC | gi|540431|pdb|1GNA| | |
| 58 | NSYPGCPSSYDGYCLNGGVCMHIESLDSYTCNCVIGYSGDRCQTRDLRWWELR | gi|494001|pdb|1EGF| | 3.9 |
| 59 | NDDCELCVNVACTGCL | gi|2961619|pdb|1UVA| | |
| 60 | EQCGRQAGGKLCPNNLCDSQWGWCGSTDEYCSPCHNCGSNCKD | gi|494093|pdb|1HEV| | 7.3 |

FIG. 12

Ah-AMP-1 (Plant)
HGA--CHKRENHWKCFCYFNC

IL-8 (Human)
CANTEIIVKLSDGRELCLDP

PF-4 (Human)
CPTAQLIATLKNGRKICLDLQAP

GRO-α (Human)
CAQTEVIATLKNGRKACLNPASP

Lymphotactin (Human)
RAVIFITKRGLKVCADP

MCP-1 (Human)
CPKEAVIFKTIVAKEICADP

RANTES (Human)
CSNPAVVFVTRKNRQVCANP

ANTIMICROBIAL KINOCIDIN COMPOSITIONS AND METHODS OF USE

This application is a continuation application of U.S. Non-Provisional application Ser. No. 12/438,923, filed Oct. 6, 2009 now abandoned, which was a 371 National Stage of International Application No. PCT/US2007/14499, filed on Jun. 20, 2007, which claims the benefit of the filing date of U.S. Provisional Application No. 60/815,491, filed Jun. 20, 2006, and which are incorporated herein by reference in their entirety.

BACKGROUND OF THE INVENTION

This invention relates to peptides having antibacterial and antifungal properties. The invention also concerns the preparation of these peptides and compositions containing the same which may be used in agriculture and for human or animal therapy.

Nature provides a context in which organisms across the phylogenetic spectrum are confronted by potential microbial pathogens. In turn, natural selection provides a corresponding requirement for rapid and effective molecular stratagems of host defense against unfavorable microbial infection. Antimicrobial peptides represent a key result of this co-evolutionary relationship. While higher organisms have evolved complex and adaptive immune systems, virtually all organisms rely upon primary innate immune mechanisms that are rapidly deployed to ward off microbial invasion. Discoveries over the last decade indicate that antimicrobial peptides elaborated by essentially all organisms play integral roles in these innate mechanisms of antimicrobial host defense.

Antimicrobial peptides may be generally categorized as those with or without disulfide bridges. Those that contain disulfides commonly adopt β-sheet structures, while those lacking cysteine crosslinkages often exhibit α-helical conformation. Antimicrobial peptides from both classes have a number of conserved features that likely contribute to their toxicity to microorganisms, including: 1) small size, typically ranging from 12-50 amino acids; 2) cationicity, with net charges ranging from +2 to +7 at pH 7; and 3) amphipathic stereogeometry conferring relatively polarized hydrophilic and hydrophobic facets (Yeaman and Yount, *Pharmacol. Rev.* 55:27 (2003)). The limited size of these polypeptides places restrictions on the structural repertoire available to meet these requirements. Despite these limitations, as a group antimicrobial peptides display a high degree of variability at non-conserved sites, with amino acid substitution rates on the order of those associated with positive selection (A. L. Hughes, *Cell. Mol. Life. Sci.* 56:94 (1999)). These observations are consistent with the hypothesis that co-evolutionary selective pressures drive host-pathogen interactions (M. J. Blaser, *N. Engl. J. Med.* 346:2083 (2002)).

Amino acid sequence motifs have previously been identified within certain antimicrobial peptide subclasses (eg., the cysteine array in certain mammalian defensins; White et al., *Curr. Opin. Struct. Biol.* 5:521 (1995)). Yet, comparatively little is known about more comprehensive relationships uniting all antimicrobial peptides. Conventional sequence analyses performed have yielded limited sequence conservation, and no universal structural homology has been identified amongst antimicrobial peptides. If present, such a consensus motif across the diverse families of antimicrobial peptides would provide insights into the mechanism of action of these molecules, yield information on the evolutionary origin of these sequences, and allow prediction of antimicrobial activity in molecules recognized to have other functions.

The ability of certain bacteria such as *M. tuberculosis* and *S. aureus* among others, to develop resistance to antibiotics represents a major challenge in the treatment of infectious disease. Unfortunately, relatively few new antibiotic drugs have reached the market in recent years. Methods for administering new classes of antibiotics might provide a new scientific weapon in the war against bacterial infections.

There are only a handful of antifungal drugs known for the treatment of mammals. In fact, there were only ten FDA approved antifungal drugs available in 2000 for the treatment of systemic fungal infections. There are three important classes of fungal drugs for the treatment of systemic infections: polyenes, pyrimidines, and azoles. The FDA has also approved certain drugs belonging to other classes for topical treatment of fungal infections. Certain traditional antifungal drugs may have a significant toxicity, and certain antifungal drugs available for use in treatment have a limited spectrum of activity. Still further, certain antifungal drugs among the azoles can have interactions with coadministered drugs, which can result in adverse clinical consequences. As with the antibiotics, certain fungi have developed resistance to specific antifungal drugs. Patients with compromised immune systems (e.g., AIDS) patients have in some cases had prolonged exposure to fluconazole for both prophylactic and therapeutic purposes. In 2000, increased use of the drug fluconazole correlated with the isolation of increasing numbers of resistant infectious fungi among AIDS patients. Methods of using a new class of antifungal drugs could make new treatments for fungal infections possible.

Invasive mycoses are very serious infections caused by fungi found in nature and which become pathogenic in immunocompromised persons. Immunosuppression may be the result of various causes: corticotherapy, chemotherapy, transplants, HIV infection. Opportunistic fungal infections currently account for a high mortality rate in man. They may be caused by yeasts, mainly of *Candida* type, or filamentous fungi, chiefly of *Aspergillus* type. In immunosuppressed patients, failure of antifungal treatment is frequently observed on account of its toxicity, for example, treatment with Amphotericin B, or the onset of resistant fungi, for example resistance of *Candida albicans* to nitrogen derivatives. It is, therefore, vital to develop new antifungal medicinal products derived from innovative molecules. In this context, antimicrobial peptides offer an attractive alternative.

Antimicrobial peptides are ubiquitous in nature and play an important role in the innate immune system of many species. Antimicrobial peptides are diverse in structure, function, and specificity. A number of antimicrobial peptides occur naturally as "host-defense" compounds in humans, other mammals, amphibians, plants and insects, as well as in bacteria themselves. Synthetic antimicrobial peptides have also been described, including highly amphipathic peptides whose amino acid sequences are related to or derived from the sequences of various viral membrane proteins.

The significant advantage of peptide antimicrobials resides in the global mechanism of their anti-microbial action; because peptides have an inherent capacity to bind and penetrate biological membranes, these compounds act by physically disrupting cellular membranes, usually causing membrane lysis and eventually cell death. Organisms such as bacteria have little ability to combat this physical mechanism and acquire resistance.

Thus, there exists a need for employing multidimensional proteomic techniques to determine structural commonalities amongst peptides elaborated in phylogenetically diverse organisms—microbial to human—and explore the potential convergence of structural paradigms in these molecules. The present invention satisfies this need and provides related advantages as well.

SUMMARY OF THE INVENTION

The present invention provides novel kinocidin peptides comprising a C-terminal portion of a kinocidin, wherein the C-terminal portion encompasses an α-helical secondary structure and further displays antimicrobial activity. The kinocidin peptides of the invention are derived from and correspond to a C-terminal portion of a kinocidin, wherein the kinocidin includes a $\gamma_{KC}$ core and can be a CXC, CX$_3$C, CC, or C class chemokine. Structural, physicochemical and functional properties of this novel class of antimicrobial peptides and amino acid sequences of particular kinocidin peptides are also disclosed. The invention also provides related antimicrobial methods.

BRIEF DESCRIPTION OF THE DRAWINGS

FIG. 2 (B) shows convergence in the sequence patterns of cysteine-containing antimicrobial peptides. The consensus primary structural motifs were identified amongst the prototypical disulfide-containing antimicrobial peptide study set. Sequence data and disulfide arrays indicated were derived from the following sources (in descending order): α-defensins (SEQ ID NO: 56) (Yount et al., *J. Biol. Chem.* 274: 26249 (1999)); β-defensins (SEQ ID NO: 57) (Yount et al., *J. Biol. Chem.* 274:26249 (1999)); insect defensins (SEQ ID NO: 58) (sapecin; Hanzawa et al., *FEBS Lett.* 269:413 (1990)); insect CS-αβ peptides (SEQ ID NO: 59) (drosomycin; Landon et al., *Protein Sci.* 6:1878 (1997)); plant CS-αβ peptides (SEQ ID NO: 60) (Ah-AMP-1; Fant et al., *Proteins* 37:388 (1999)); crustacea CS-αβ peptides (SEQ ID NO: 61) (MGD-1; Yang et al., *Biochemistry* 39:14436 (2000)); gaegurin (SEQ ID NO: 64) (gaegurin-1; Park et al., *Biochem. Biophys. Res. Commun.* 205:948 (1994)); protegrin (SEQ ID NO: 62) (protegrin-1; Fahrner et al., *Chem. Biol.* 3:543 (1996)); gomesin (SEQ ID NO: 65) (Silva et al., *J. Biol. Chem.* 275:33464 (2000); Mandard et al., *Eur. J. Biochem.* 269:1190 (2002)); thanatin (SEQ ID NO: 66) (Mandard et al., *Eur. J. Biochem.* 256:404 (1998)); tachyplesin (SEQ ID NO: 67) (tachyplesin I; Nakamura et al., *J. Biol. Chem.* 263:16709 (1988)); mytilin (SEQ ID NO: 63) (mytilin Charlet et al., *J. Biol. Chem.* 271:21808 (1996)); AFP-1 (SEQ ID NO: 68) (Campos-Olivas et al., *Biochemistry* 34:3009 (1995)). The primary sequences corresponding to the γ-core motif are outlined in red (see FIG. 4). Sequences are shown in their conventional dextromeric orientations (N- to C-termini from left to right) unless indicated to be projected in a levomeric orientation (levo; C- to N-termini from left to right).

FIG. 3 (I-L) demonstrates the absence of the γ-core signature in non-antimicrobial peptides. Three-dimensional conformity between prototypic antimicrobial and non-antimicrobial peptides was determined as described in FIG. 3 A-H. Representative comparisons are between the antimicrobial peptide Ah-AMP1, and the following non-antimicrobial peptides (identified as formatted in FIG. 3 A-H): allergen-5 ([2BBG], *Ambrosia*, ragweed; RMSD 6.5 Å; panel I); metallothionein II ([1AOO], *Saccharomyces*, yeast; RMSD 5.3 Å; panel J); TGF-α ([3TGF], *Homo*, human; RMSD 4.7 Å; panel K); and ferredoxin ([2FDN], *Clostridium*, bacterium; RMSD 7.4 Å; panel L). Each non-antimicrobial comparator peptide (blue) is shown in maximal alignment with Ah-AMP1 (gray). Amino-(N) and carboxy-(C) termini are indicated as defined in FIG. 3 A-H. See Table II for references.

FIG. 4 shows conservation of the γ-core motif amongst disulfide-containing antimicrobial peptides. The conserved γ-core motif (red) is indicated with corresponding sequences (GXC or CXG-C motifs are denoted in red text). Examples are organized into four structural groups relative to the γ-core. Group (γ): protegrin-1, [1PG1] (SEQ ID NO: 69); gomesin [1KFP] (SEQ ID NO: 70); tachyplesin-1 [1MA2] (SEQ ID NO: 71); RTD-1 [1HVZ] (SEQ ID NO: 72); thanatin [8TFV] (SEQ ID NO: 73); hepcidin [1M4F] (SEQ ID NO: 74)); Group (γ-α): sapecin [1LV4] (SEQ ID NO: 75); insect defensin A [1ICA] (SEQ ID NO: 76); heliomicin [1I2U] (SEQ ID NO: 77); drosomycin [1MYN] (SEQ ID NO: 78); MGD-1 [1FJN] (SEQ ID NO: 79); charybdotoxin [2CRD] (SEQ ID NO: 80)); Group (β-γ): HNP-3 [1DFN] (SEQ ID NO: 81); RK-1 [1EWS] (SEQ ID NO: 82); BNBD-12 [1BNB] (SEQ ID NO: 83); HBD-1 [1E4S] (SEQ ID NO: 82); HBD-2 [1E4Q] (SEQ ID NO: 85); mBD-8 [1E4R] (SEQ ID NO: 86)); and Group (β-γ-α): Ah-AMP-1 [1BK8] (SEQ ID NO: 87); Rs-AFP-1 [1AYJ] (SEQ ID NO: 88); Ps-Def-1 [1JKZ] (SEQ ID NO: 89); γ-1-H-thionin [1GPT] (SEQ ID NO: 91); γ-1-P-thionin [1GPS] (SEQ ID NO: 91); and brazzein [1BRZ] (SEQ ID NO: 92). Protegrin, gomesin, tachyplesin, RTD-1, and thanatin γ-core sequences (Group γ) are depicted in levomeric orientation. Other peptide data are formatted as in FIG. 3. See Table II for additional references.

FIG. 5 (A-C) shows iterations of the 3-dimensional γ-core motif. Amino acid consensus patterns of the three γ-core sequence isoforms are shown. Coloration represents the most common residue (>50% frequency) at a given position, as adapted from the RASMOL schema: cysteine (C), yellow; glycine (G), orange; lysine or arginine, royal blue; serine or threonine, peach; leucine, isoleucine, alanine or valine, dark green; aromatic, aqua; and variable positions (<50% consensus), gray.

FIG. 8 (B) shows modular iterations of multidimensional signatures in disulfide-stabilized antimicrobial peptides. Distinct configurations integrating the γ-core are found in naturally occurring antimicrobial peptides from diverse organisms. Specific examples are used to illustrate this theme (modular formulae are as described in the text): [γ], Protegrin-1; [γα$_1$], MGD-1; [γβ$_1$], HNP-3; and [γα$_1$β$_1$], Ah-AMP-1. Color schema and peptide identification are as indicated in FIG. 3 (A, C, E, G).

Figure 10C:
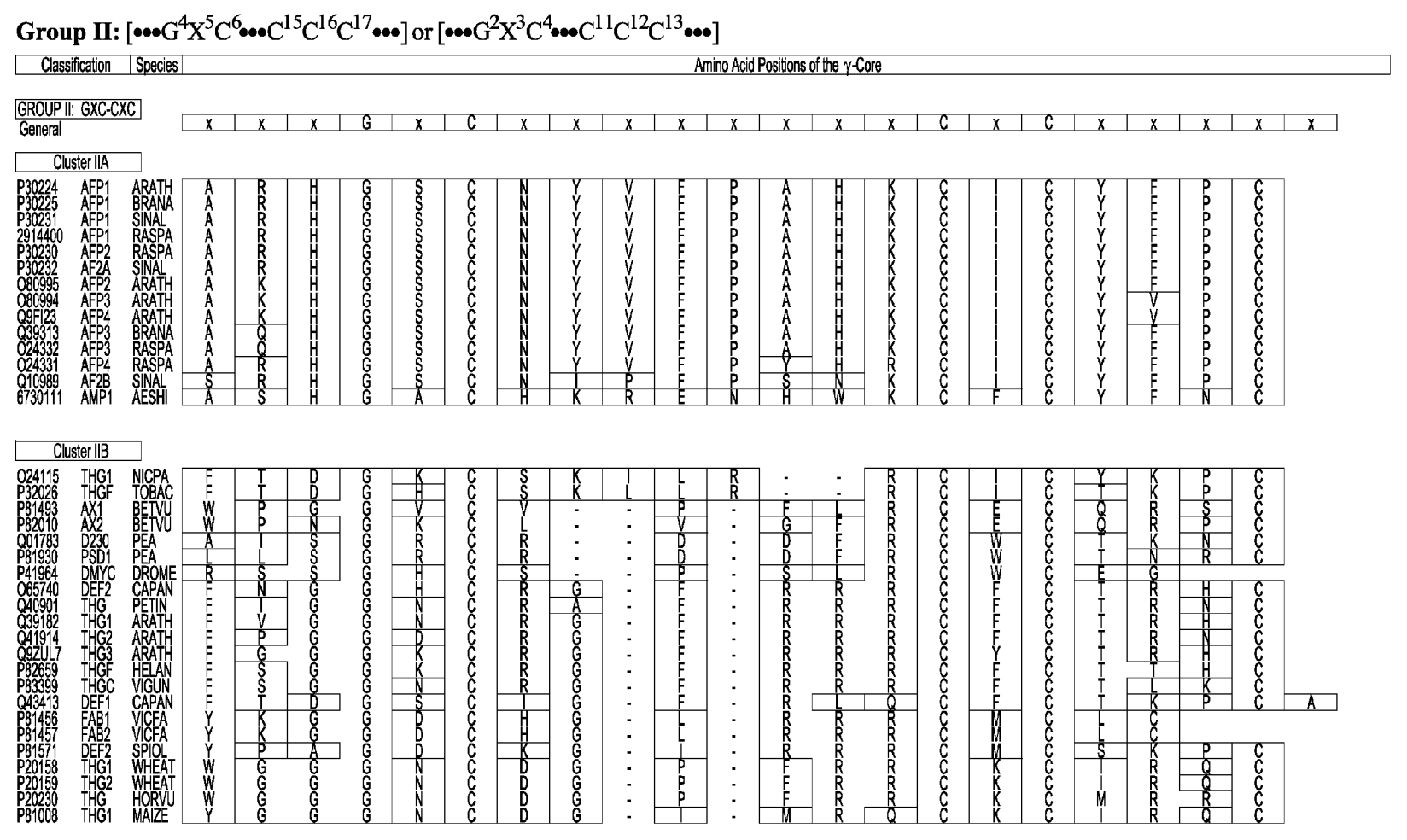
Figure 10D:
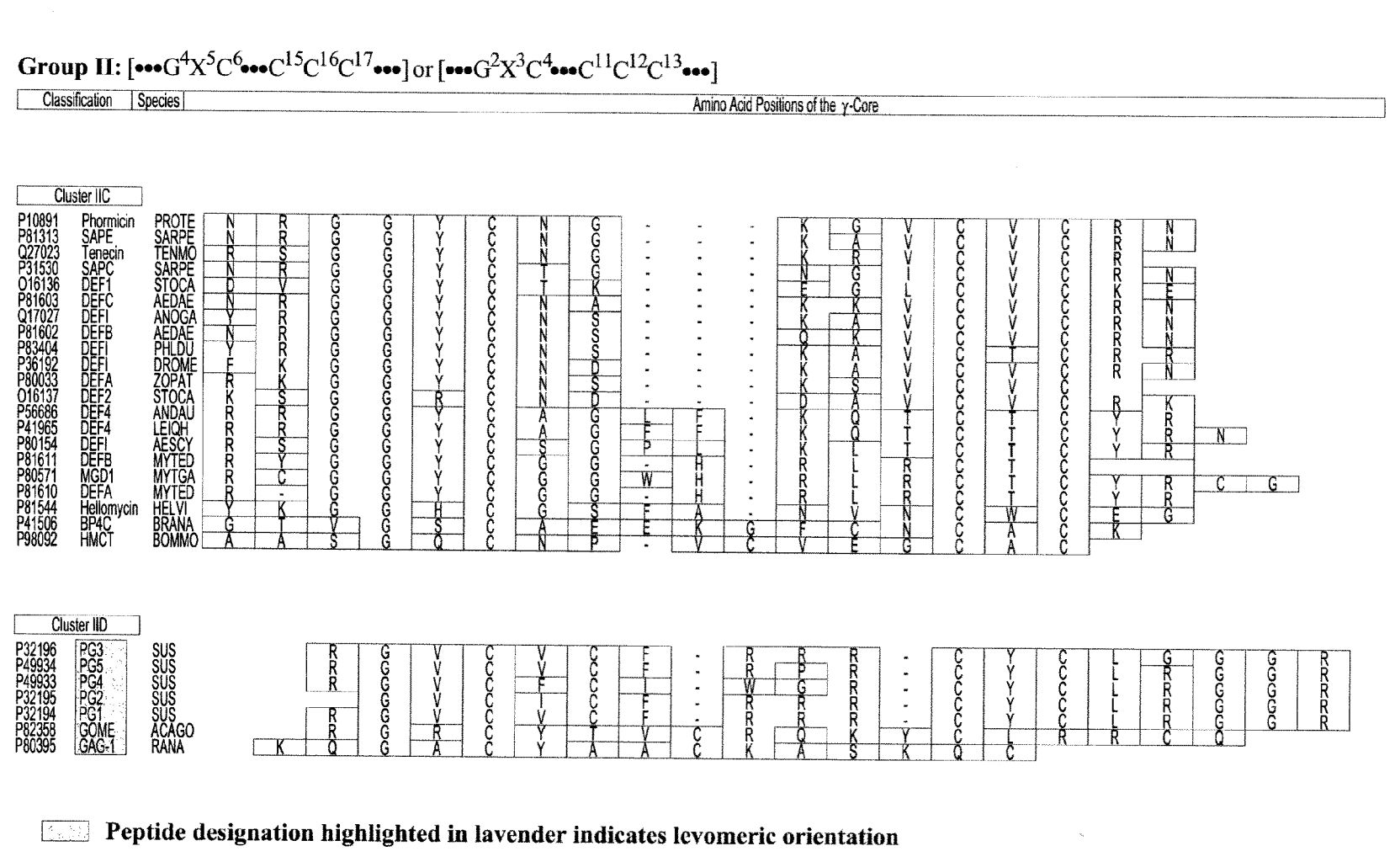

FIG. 10, panels A-E, depict amino acid sequences of γ-core signature motifs amongst disulfide-containing antimicrobial peptides. Nomenclature and coloration are as indicated in FIGS. 2 and 3 of the primary manuscript; standard abbreviations are used for peptide names where appropriate. Lavender shading of molecule identities in Groups IID and IIIB indicates peptides aligned in the levomeric orientation. These sequences correspond to the γ-core pattern map as depicted in FIG. 3 of the primary manuscript. FIG. 10C depicts amino acid sequences of SEQ ID NOS: 173-210, in order from top to bottom. FIG. 10D depicts amino acid sequences of SEQ ID NOS: 211-238, in order from top to bottom.

FIG. 11, Panels A and B, show peptides with predicted antimicrobial activity based on the multidimensional signature. Candidate peptides were identified by VAST alignment, 3D-RMSD, and manual comparisons; all RMSD scores compared with Ah-AMP-1 (1BK8; Aesculus); threshold typically >4.5 excluded; each sequence is identified by NCBI accession number. FIG. 11A depicts amino acid sequences of SEQ ID NOS: 256-390, in order from top to bottom. FIG. 11B depicts amino acid sequences of SEQ ID NOS: 291-315, in order from top to bottom.

FIG. 12 shows alignment of C, CC and CXC class human chemokines (SEQ ID NOS: 316-351). The highlighted $GX_3C$ motif [glycine (G), orange; cysteine (C), yellow; proline (P), aqua] corresponds to the $\gamma_{KC}$ core signature (outlined in red). Conserved cysteine residues beyond the $\gamma_{KC}$ core are shaded gray. Gaps were introduced to achieve maximal alignment; * indicates truncated sequence.

DETAILED DESCRIPTION OF THE INVENTION

Figure 1:
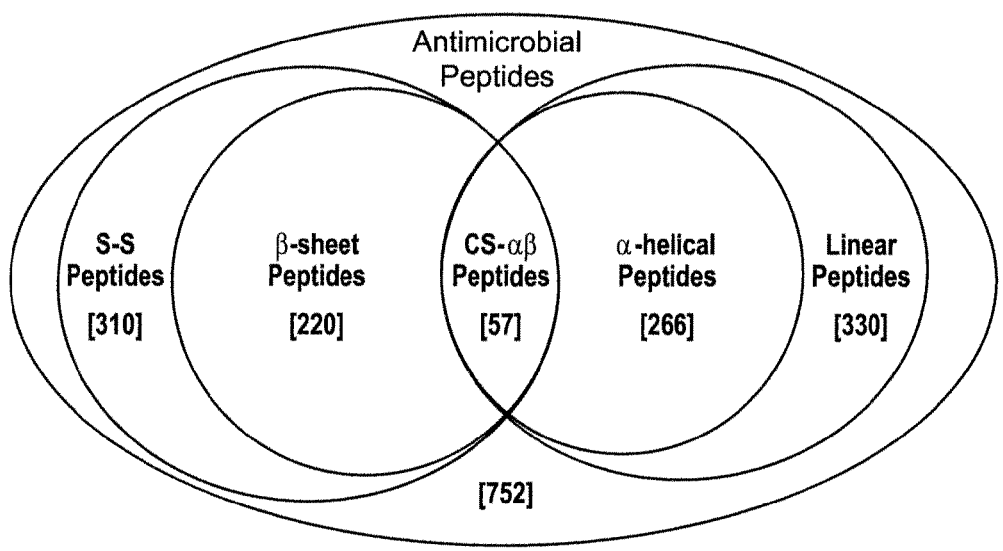
FIG. 1 shows conventional antimicrobial peptide structure classification and distribution. Relationship amongst structure and predominance is summarized for the commonly recognized antimicrobial peptide classes. Concatenation represents the proportionate distribution of peptides encompassing a given structural class, as calculated from the Antimicrobial Sequences Database. Numbers of peptides classified in each group are indicated in brackets for each class.

This application file contains drawings executed in color. Copies of this patent or application publication with color drawings will be provided by the Office upon request and payment of the necessary fee.

This invention provides antimicrobial kinocidin peptides and related methods of use. The antimicrobial kinocidin peptides of the invention encompass at least a portion of the C-terminal α-helical region of a kinocidin, wherein the C-terminal portion encompasses an α-helical secondary structure. The kinocidin peptides of the invention are derived from and correspond to a C-terminal portion of a kinocidin that includes a $\gamma_{KC}$ core predictive of antimicrobial activity. A kinocidin is a antimicrobial CXC, $CX_3C$, CC, or C class chemokine.

The kinocidin peptide can include up to the entire C-terminal α-helix of the corresponding kinocidin from which it is derived. A kinocidin peptide generally has physicochemical properties within the ranges set forth in Table IV below and also has antimicrobial activity The term "kinocidin," as used herein refers to a chemokine having microbicidal activity. As described herein, the ability of a chemokine to exert antimicrobial activity can be predicted based on the presence of the $\gamma_{KC}$ core consensus formula, and specific physicochemical patterns of amphipathicity, charge distribution, and proline positioning within the chemokine (see FIG. 1). More than 40 human chemokines have been characterized and are classified into four groups according to conserved N-terminal cysteine motifs: CXC (α-chemokines), CC (β-chemokines), C, and $CX_3C$ (Hoffmann et al. (2002) J Leukoc Biol 72, 847-855).

As used herein, the term "kinocidin peptide" refers to a peptide that has microbicidal activity and that contains all or a portion of a C-terminal α-helix of a kinocidin. In structural terms, a kinocidin peptide of the invention is characterized by corresponding to a C-terminal portion of a kinocidin. As described throughout this disclosure, a kinocidin can be selected based on the presence of the $\gamma_{KC}$ core consensus formula, and specific physicochemical patterns of amphipathicity, charge distribution, and proline positioning within the chemokine (see FIG. 12). In functional terms, a kinocidin peptide has antimicrobial, for example, antimicrobial and/or antifungal activity, which can be confirmed via routine methods described in the art and exemplified herein. A kinocidin peptide of the invention can have any length provided the requisite activity is present, for example, can be between 50 or less, 45 or less, 40 or less, 35 or less, 34 or less, 33 or less, 32 or less, 30 or less, 29 or less, 28 or less, 27 or less, 26 or less, 25 or less, 24 or less. 23 or less, 22 or less, 21 or less, 20 or less, 19 or less, 18 or less, 17 or less, 16 or less, 15 or less, 14 or less, 13 or less, 12 or less, 11 or less, 10 or less, 9 or less, 8 or less, 7 or less, 6 or less, 5 or less, and preferably between 10 and 40, more preferably between 12 and 38, more preferably between 14 and 32 amino acids in length. Also encompassed within the term are dimers and other multimers, truncated molecules, and molecules that contain repetitions of particular subsequences within the motif as long as the peptide has microbicidal activity and that contains all or a portion of a C-terminal α-helix of a kinocidin.

Figure 18:
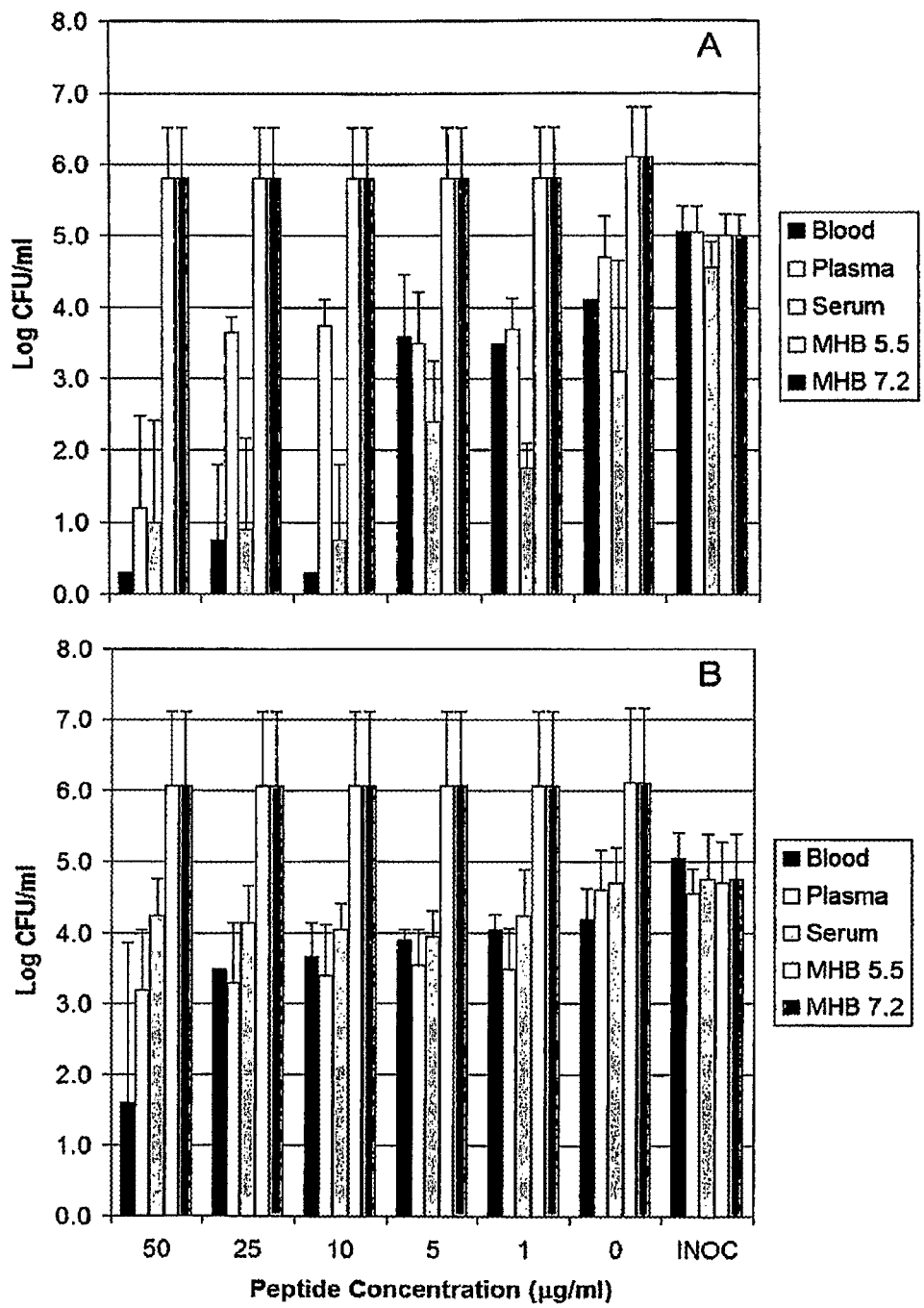
FIG. 18 shows antimicrobial efficacy of IL-8α in human blood and blood-derived matrices as compared with artificial media (MHB) at pH 5.5 and 7.2. Panel 18 (A) shows co-incubation of IL-8α and the organism simultaneously added to the test biomatrix or medium; Panel 18 (B) shows pre-incubation of IL-8α in biomatrices or media for 2 h at 37° C. prior to introduction of the organism. The *E. coli* inocula (INOC) were $10^5$ CFU/ml, and the threshold of sensitivity was considered 0.3 log 10 CFU/ml.

The invention provides particular kinocidin peptides, each comprising a C-terminal portion of a kinocidin having an sequence DAPRIKKIVQKKLAGDES (SEQ ID NO: 4). Additional kinocidin peptides of the invention based on Human CXC, CC and C Chemokine C-terminal α-Helical Domains are set forth in FIG. 18.

TABLE I

Antimicrobial peptides of the invention based on Human CXC, CC and C Chemokine C-terminal α-Helical Domains.

| Origin | Name | Amino Acid Sequence |
|---|---|---|
| CXCL1/GRO-alpha | Aegicidin hGro-α-C1 | ASPIVKKIIEKMLNSDKSN (SEQ ID NO: 3) |
| CXCL2/MIP2-alpha | Aegicidin hMIP2-α-C1 | ASPMVKKIIEKMLKNGKSN (SEQ ID NO: 5) |
| CXCL3/GRO-beta | Aegicidin hGro-β-C1 | ASPMVQKIIEKILNKGSTN (SEQ ID NO: 6) |
| CXCL4/PF-4 | | QAPLYKKIIKKLLES; (SEQ ID NO: 2) |
| CXCL5/ENA-78 | Aegicidin hENA-78-C1 | EAPFLKKVIQKILDGGNKEN (SEQ ID NO: 7) |
| CXCL6/GCP-2 | Aegicidin hGCP-2-C1 | EAPFLKKVIQKILDSGNKKN (SEQ ID NO: 8) |
| CXCL7/PBP, CTAP3, NAP2 | | DAPRIKKIVQKKLAGDESAD (SEQ ID NO: 9) |
| CXCL8/IL-8 | Aegicidin hIL-8-C1 | KENWVQRVVEKFLKRAENS (SEQ ID NO: 1) |
| CXCL9/MIG | Aegicidin hMIG-C1 | DSADVKELIKKWEKQVSQKKKQKNGKK (SEQ ID NO: 359) |
| CXCL10/IP-10 | Aegicidin hIP-10-C1 | ESKAIKNLLKAVSKERSKRSP (SEQ ID NO: 10) |
| CXCL11/I-TAC | Aegicidin hI-TAC-C1 | KSKQARLIIKKVERKNF (SEQ ID NO: 11) |
| CXCL12/SDF-1 | Aegicidin hSDF-1-C1 | KLKWIQEYLEKALNKRFKM (SEQ ID NO: 12) |
| CXCL13/BCA-1 | Aegicidin hBCA-1-C1 | QAEWIQRMMEVLRKRSSSTLPVPVFKRKIP* (SEQ ID NO: 13) |
| CXCL14/BRAK | Aegicidin hBRAK-C1 | KLQSTKRFIKWYNAWNEKRRVYEE (SEQ ID NO: 14) |

Group 2
Based on Human CC Chemokine α-Helical Domains

| | | |
|---|---|---|
| CCL1/I-309 | Aegicidin hI-309-C1 | TVGWVQRHRKMLRHCPSKRK (SEQ ID NO: 15) |
| CCL2/MCP-1 | Aegicidin hMCP-1-C1 | KQKWVQDSMDHLDKQTQTPKT (SEQ ID NO: 16) |
| CCL3/MIP-1alpha | Aegicidin hMIP-1α-C1 | SEEWVQKYVSDLELSA (SEQ ID NO: 17) |
| CCL4/MIP-1beta | Aegicidin hMIP-1β-C1 | SESWVQEYVYDLELN (SEQ ID NO: 18) |
| CCL5/RANTES | Aegicidin hRANTES-C1 | EKKWVREYINSLEMS (SEQ ID NO: 19) |
| CCL7/MCP-3 | Yeaman & Yount terminology: Aegicidin hMCP3-C1 | TQKWVQDFMKHLDKKTQTPKL (SEQ ID NO: 20) |
| CCL8/MCP-2 | Aegicidin hMCP-2-C1 | KERWVRDSMKHLDQIFQNLKP (SEQ ID NO: 21) |
| CCL11/EOTAXIN | Aegicidin hEOTx-C1 | KKKWVQDSMKYLDQKSPTPKP (SEQ ID NO: 22) |
| CCL13/MCP-4 | Aegicidin hMCP-4-C1 | KEKWVQNYMKHLGRKAHTLKT (SEQ ID NO: 23) |
| CCL14/HCC-1 | Aegicidin hHCC-1-C1 | SDKWVQDYIKDMKEN (SEQ ID NO: 24) |
| CCL15/HCC-2 | Aegicidin hHCC-2-C1 | SGPGVQDCMKKLKPYSI (SEQ ID NO: 25) |
| CCL16/HCC-4 | Aegicidin hHCC-4-C1 | NDDWVQEYIKDPNLPLLPTRNLSTVKII (SEQ ID NO: 26) |
| CCL17/TARC | Aegicidin hTARC-C1 | NNKRVKNAVKYLQSLERS (SEQ ID NO: 27) |
| CCL18/PARC | Aegicidin hPARC-C1 | NKKWVQKYISDLKLNA (SEQ ID NO: 28) |
| CCL19/MIP-3beta | Aegicidin hMIP-3β-C1 | DQPWVERIIQRLQRTSAKMKRRSS (SEQ ID NO: 29) |
| CCL20/LARC | Aegicidin hLARC-C1 | KQTWVKYIVRLLSKKVKNM (SEQ ID NO: 30) |
| CCL21/SLC | Aegicidin hSLC-C1 | KELWVQQLMQHLDKTPSPQKPAQG (SEQ ID NO: 31) |
| CCL22/MDC | Aegicidin hMDC-C1 | RVPWVKMILNKLSQ (SEQ ID NO: 32) |
| CCL23/MPIF-1 | Aegicidin hMPIF-1-C1 | SDKQVQVCVRMLKLDTRIKTRKN (SEQ ID NO: 33) |
| CCL24/MPIF-2 | Aegicidin hMPIF-2-C1 | KQEWVQRYMKNLDAKQKKASPRAR (SEQ ID NO: 34) |
| CCL25/TECK | Aegicidin hTECK-C1 | KSREVQRAMKLLDARNK* (SEQ ID NO: 35) |
| CCL27/SKINKINE | Aegicidin hSkine-C1 | QNPSLSQWFEHQERKLHGTLPKLNFGMLRKMG (SEQ ID NO: 36) |
| CCL28/CCK1 | Aegicidin hCCK-1-C1 | HNHTVKQWMKVQAAKKNGKGN* (SEQ ID NO: 37) |

Group 3
Peptides Based on C Chemokine α-Helical Domains

| | | |
|---|---|---|
| CL1/Lymphotactin | Aegicidin hLym-C1 | QATWVRDVVRSMDRKSNTRNN* (SEQ ID NO: 38) |

α-helical secondary structure and antimicrobial activity, and further having a $\gamma_{KC}$ core. As described herein, the kinocidin can be a CXC, CC, or C class chemokine. In one embodiment, the invention provides a kinocidin peptide that corresponds to a CXC chemokine has the amino acid sequence KENWVQRVVEKFLKRAENS (SEQ ID NO: 1). In another embodiment, the invention provides a kinocidin peptide that corresponds to a CXC chemokine has the amino acid sequence QAPLYKKIIKKLLES (SEQ ID NO: 2). In a further embodiment, the invention provides a kinocidin peptide that corresponds to a CXC chemokine has the amino acid sequence ASPIVKKIIEKMLNSDKSN (SEQ ID NO: 3). In a further embodiment, the invention provides a kinocidin peptide that corresponds to a CXC chemokine has the amino acid Chemokines comprise a class of small secretory cytokines that play important roles in potentiating leukocyte chemonavigation and antimicrobial activity. More than 40 human chemokines have been characterized and are classified into four groups according to conserved N-terminal cysteine motifs: CXC (α-chemokines), CC (β-chemokines), C, and $CX_3C$ (*J Leukoc Biol* 70, 465-466 (2001)). Chemokines have been identified in vertebrates as distant as teleost fish, and are expressed in a broad array of mammalian cell types including those of myeloid, endothelial, epithelial and fibroblast lineages (Hoffmann et al. (2002) *J Leukoc Biol* 72, 847-855). Of the chemokines, interleukin-8 (IL-8; or CXC-ligand 8 [CXCL8]) is perhaps the best characterized, having been first identified as neutrophil-activating factor from human monocytes more than 15 years ago (Walz et al. (1987) *Biochem*

Biophys Res Commun 149, 755-761; Yoshimura et al. (1987) Proc Natl Acad Sci USA 84, 9233-9237).

This invention further describes methods for identifying multidimensional protein signatures that are useful as predictors of protein activity. Prior to this invention it was unknown that proteins can be classified based on common multidimensional signatures that are predictive of activity. While exemplified herein for a subclass of antimicrobial peptides, this discovery allows for the invention methods of using experimental proteomics techniques to identify multidimensional protein signatures that are predictive of protein activity.

Based, in part, on the discovery of structural signatures in antimicrobial peptides, the invention provides methods for designing, creating or improving anti-infective agents and anti-infective strategies that are refractory to microbial resistance. The invention methods can improve the efficacy of a drug or a drug candidate by altering the multidimensional antimicrobial signature so as to approximate the multidimensional signature model.

In one embodiment, the invention provides a method for predicting antimicrobial activity of a candidate protein by determining the presence a multidimensional antimicrobial signature in a candidate protein, and comparing the multidimensional antimicrobial signature to a multidimensional antimicrobial signature model. As taught herein, the degree of similarity between the multidimensional antimicrobial signature of the candidate protein and the multidimensional antimicrobial signature model is predictive of antimicrobial activity of the candidate protein.

In a further embodiment, the invention provides a method for identifying a protein having antimicrobial activity by screening a library of candidate proteins to identify a multidimensional antimicrobial signature in a candidate protein, and subsequently comparing the multidimensional antimicrobial signature to a multidimensional antimicrobial signature model. As taught herein, the degree of similarity between the multidimensional antimicrobial signature of the candidate protein and the multidimensional antimicrobial signature model is predictive of antimicrobial activity of the candidate protein.

In a further embodiment, the invention provides a method for improving the antimicrobial activity of a protein by altering the multidimensional antimicrobial signature of the protein to increase the degree of similarity between the multidimensional antimicrobial signature of the protein and a multidimensional antimicrobial signature model. The invention also provides a protein having improved antimicrobial activity as a result of alteration of the multidimensional antimicrobial signature of the protein to increase the degree of similarity between the multidimensional antimicrobial signature of the protein and a multidimensional antimicrobial signature model.

In a further embodiment, the invention provides a method for designing a protein having antimicrobial activity by incorporating configurations that include iterations of a γ-core signature into a peptide structure that is designed. The invention also provides a protein having antimicrobial activity designed by incorporating configurations that include iterations of a γ-core signature into a peptide structure.

As used herein, the term "multidimensional protein signature" is intended to refer to a set of essential physicochemical components that make up a structural motif characteristic of a class or subclass of proteins. A multidimensional protein signature can incorporate any structural information ascertainable, including, information regarding primary structure, including amino acid sequence, composition, and distribution patterns; secondary structure, stereospecific sequence and 3-dimensional conformation. As used herein, the term "multidimensional protein signature model" refers to a protein that represents the essential structural components associated with a particular multidimensional protein signature. Individual peptides each contain an iteration of the multidimensional signature, and the essential features of this signature are reflected in the multidimensional signature model. CS-αβ family antimicrobial peptides also contain a $\gamma_{AP}$ core and α-helix Kinocidins, including IL-8, share a common topology comprised of a $\gamma_{KC}$ core and α-helix.

As used herein, the terms "gamma-core motif," "γ-core," "$\gamma_{AP}$-core," "γ-core signature" and equivalents thereof refer to a multidimensional protein signature, in particular a multidimensional antimicrobial signature, that is characterized by two anti-parallel β-sheets interposed by a short turn region with a conserved GXC (dextromeric) or CXG (levomeric) sequence pattern integrated into one β-sheet. Additional features that characterize the γ-core motif include a hydrophobic bias toward the C-terminal aspect and cationic charge positioned at the inflection point and termini of the β-sheet domains, polarizing charge along the longitudinal axis of the γ-core.

The kinocidin γ-core ($\gamma_{KC}$ core) signature is an iteration of the antimicrobial peptide γ-core ($\gamma_{AP}$), conforming to an anti-parallel β-hairpin comprised of a 13-17 amino acid pattern with a central hydrophobic region typically flanked by basic residues. The $\gamma_{KC}$ core motif can be characterized by the following consensus sequence formula:

$$NH_2[C]-[X_{10-13}]-[GX_{2-3}C]-[X_2]-[P]COOH \quad \text{(SEQ ID NO:39)}$$

Human IL-8, which contains the kinocidin γ-core ($\gamma_{KC}$ core) signature, has the sequence:

$$NH_2 \text{ CANTEIIVKLSDGRELCLDP COOH} \quad \text{(SEQ ID NO: 40)}$$

This fragment of the IL-8 sequence is consistent with the consensus $\gamma_{KC}$-core motif. Furthermore, many kinocidins exhibit a recurring amino acid position pattern, consistent with the consensus $\gamma_{KC}$ core formula:

(SEQ ID NO: 41)

$$NH_2CX_4Z_3X_{0-2}[K^{81}]X_{1-3}G[K^{72}][B^{86}][Z^{92}]C[Z^{86}][D^{86}][P^{95}]COOH$$
$$\phantom{NH_2CX_4Z_3X_{0-2}[K^{81}]X_{1-3}G[K^{72}][}R\phantom{^{86}][Z^{92}]C[Z^{86}][}N$$

where Z represents the hydrophobic residues A, F, I, L, V, W, Y; B represents the charged or polar residues D, E, H, K, N, R, Q; C, P, or G correspond to cysteine, proline, or glycine, respectively, X indicates variable amino acid position; and numeric superscripts of bracketed positions indicate relative frequency in percent, with common alternate residues listed beneath.

As used herein, the term "protein activity" is intended to mean a functional activity or bioactivity of a protein.

Many disulfide-containing antimicrobial peptides have multiple structural domains that encompass β-sheet and/or α-helical motifs connected through an interposing region. As described herein, the invention methods provide a strategy incorporating a synthesis of proteomic and experimental methods to identify essential structural features integral to antimicrobial bioactivity that are shared amongst broad classes of antimicrobial peptides. Stereospecific sequence and 3-dimensional conformation analyses of cysteine-containing antimicrobial peptides with known structures were integrated and reduced to identify essential structural components. These approaches enabled the identification of sequence patterns and a 3-dimensional conformation integral to a multidimensional signature common to virtually all noncyclic antimicrobial peptides containing disulfide bridges. This compelling signature transcends class-specific motifs identified previously, and reflects a unifying structural code in antimicrobial peptides from organisms separated by profound evolutionary distances.

Figure 2A:
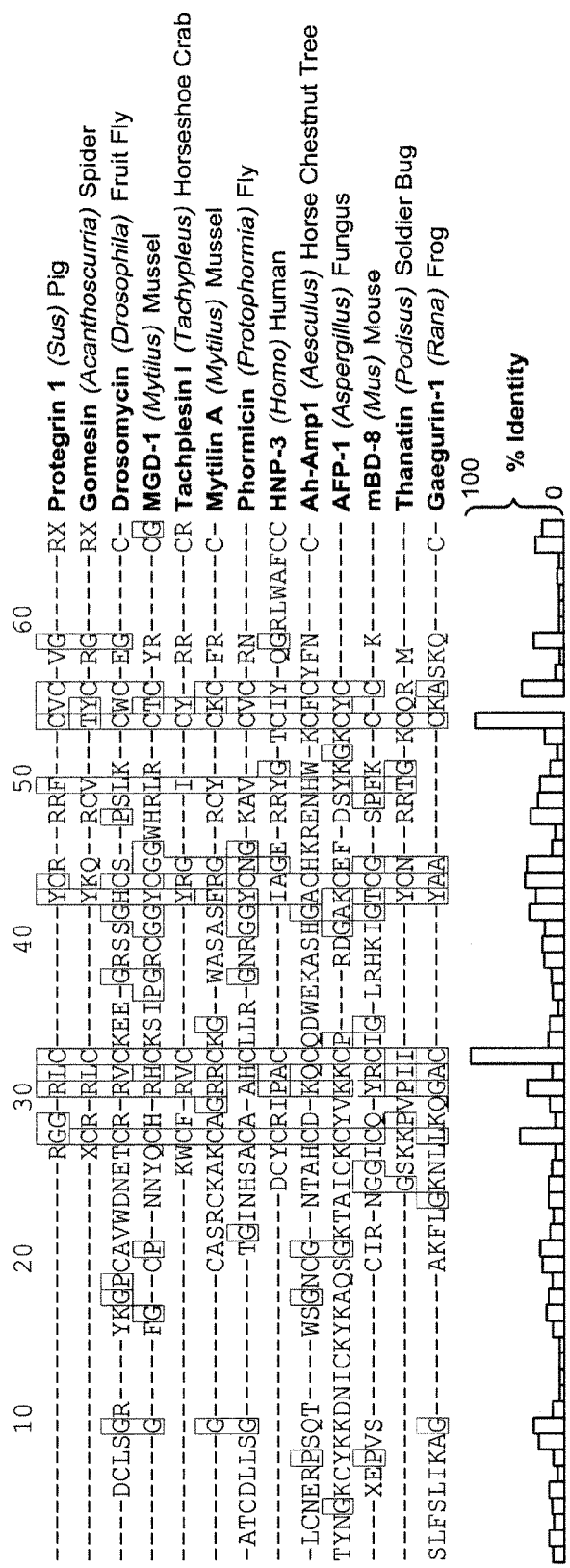
FIG. 2 (A) shows multiple sequence alignment of antimicrobial peptides examined. The MSA of the β-sheet peptide study set was generated using the Clustal W tool (Version 1.81; Higgins and Sharp, *Gene* 73:237 (1988); Higgins and Sharp, *Comput. Appl. Biosci.* 5:151 (1989)), as visualized with Jalview (M. Clamp, Jalview—java multiple alignment editor, version 1.7b (1998). Public domain (www.ebi.ac.uk/jalview/)). The coloration scheme is formatted to the Clustal degree of conservation. Individual peptides are designated by the following information series: peptide name, (source genus), and [Swiss Protein accession code]: protegrin 1, (*Sus*), [3212589] (SEQ ID NO: 43); gomesin, (*Acanthoscurria*), [20664097] (SEQ ID NO: 44); drosomycin, (*Drosophila*), [2780893] (SEQ ID NO: 45); MGD-1, (*Mytilus*), [12084380] (SEQ ID NO: 46); tachyplesin I, (*Tachypleus*), [84665] (SEQ ID NO: 47); mytilin A, (*Mytilus*), [6225740] (SEQ ID NO: 48); sapecin, (*Sarcophaga*), [20151208] (SEQ ID NO: 49); HNP-3, (*Homo*), [229858] (SEQ ID NO: 50); Ah-Amp1, (*Aesculus*), [6730111] (SEQ ID NO: 51); AFP-1, (*Aspergillus*), [1421258] (SEQ ID NO: 52); mBD-8, (*Mus*), [15826276] (SEQ ID NO: 53); thanatin, (*Podisus*), [6730068] (SEQ ID NO: 54); and gaegurin-1, (*Rana*), [1169813] (SEQ ID NO: 55).
Figure 3I:
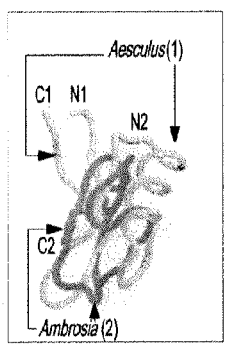
FIG. 3 (A-H) shows conservation of 3-dimensional signatures amongst antimicrobial peptides. Three-dimensional structural alignments were carried out by the combinatorial extension method (Shindyalov and. Bourne, *Protein Eng.* 11:739 (1998)), visualized using Protein Explorer (Martz, *Trends Biochem. Sci.* 27:107 (2002)). Comparisons are between (Ah-AMP-1 ([1BK8], *Aesculus*, horsechestnut tree) and (peptide name, [PDB accession code], genus, common name; RMSD): protegrin-1 ([1PG1], *Sus*, domestic pig; RMSD 1.2 Å; panels A and B); drosomycin ([1MYN], *Drosophila*, fruit fly; RMSD 1.4 Å; panels C and D); HNP-3 ([1DFN]; *Homo*, human; RMSD 3.2 Å; panels E and F); and magainin-2 ([2MAG]; *Xenopus*, frog; Gesell et al., *J. Biomol. NMR* 9:127 (1997); RMSD 2.6 Å; panels G and H). Respective amino- and carboxy-termini are indicated in panels A, C, E and G. Panels A, C, E, and G use the Clustal degree of 2° structure conservation coloration scheme. Panels B, D, F, and H employ the DRuMS polarity-2 color scheme, in which hydrophobic residues are colored gray, while hydrophilic residues are colored purple. By convention, cysteine residues are indicated as hydrophilic, although in these peptides, they are oxidized (cystine) and colored gray indicating hydrophobicity. Amino-(N-) and carboxy-(C-) termini for comparative peptides are denoted as N1 or N2 and C1 or C2, respective of peptides designated 1 or 2. Relative positions of the disulfide bonds are indicated as dotted yellow lines in panels A-H. See Table II for additional references. Proteins were visualized using Protein Explorer as described by Martz, *Trends Biochem. Sci.* 27, 107-109 (2002).
Figure 3J:
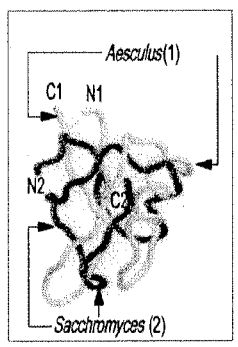
Figure 3K:
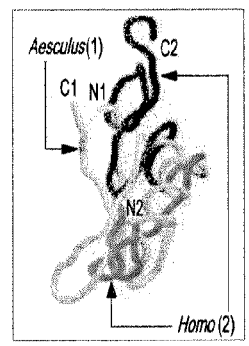
Figure 3L:
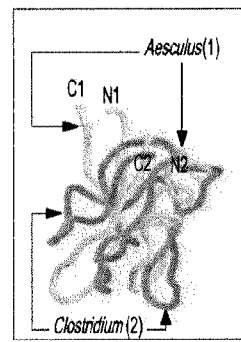
Figure 6A:
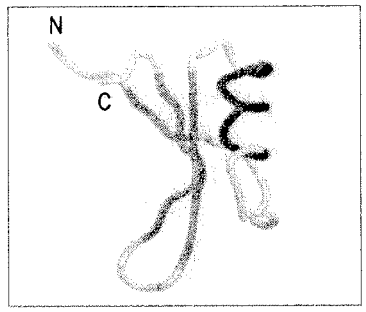
FIG. 6 (A-I) shows molecules exemplifying structure-based or activity-based validation of the multidimensional signature model. Representative molecules retrieved using the enantiomeric sequence patterns were identified (Table III) and analyzed for presence or absence of a γ-core motif as described. Thus, appropriate molecules were identified to challenge each of the respective model-based predictions. Three-dimensional structures visualized using Protein Explorer are indicated for: brazzein ([1BRZ], *Pentadiplandra*, J'Oblie berry, panels A, D, and G; Caldwell et al., *Nat. Struct. Biol.* 5:427 (1998)); charybdotoxin ([2CRD], *Leiurus*, scorpion, panels B, E, and H; Bontems et al., *Biochemistry* 31:7756 (1992)), tachyplesin I ([1MA2], *Tachypleus*, horseshoe crab, panels C, F, and I); and metallothionein II (see FIG. 3). As in FIG. 3, comparative panels A-C use the Clustal degree of 2° structure conservation coloration scheme. Panels D-F employ the DRuMS polarity-2 color scheme, in which hydrophobic residues are colored gray, and hydrophilic residues are colored purple. As in FIG. 4, amino acids comprising the γ-core motifs are highlighted in red (panels G-I) within the 3-dimensional structures of these representative peptides. Other data are formatted as in FIG. 3.
Figure 6B:
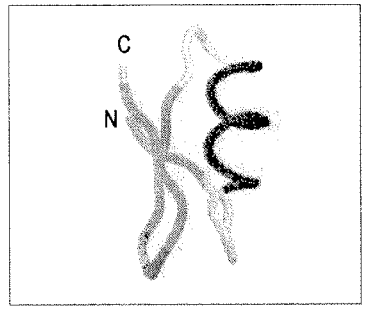
Figure 6C:
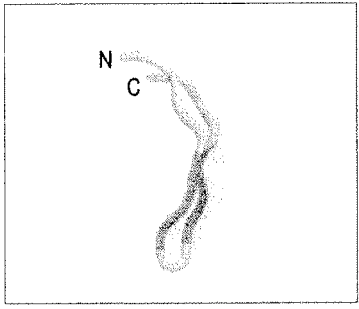
Figure 6D:
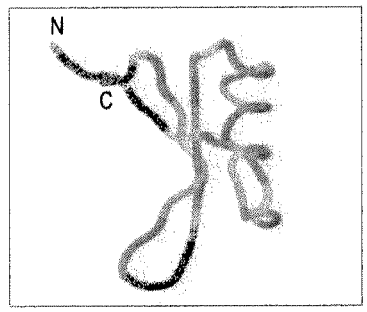
Figure 6E:
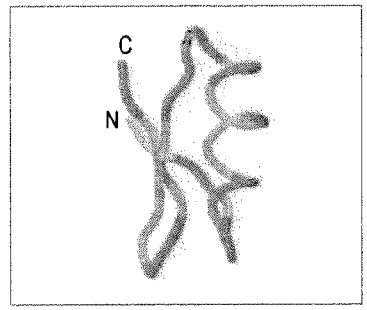
Figure 6F:
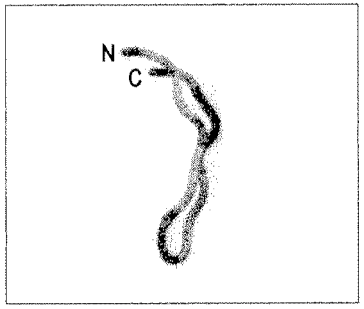
Figure 6G:
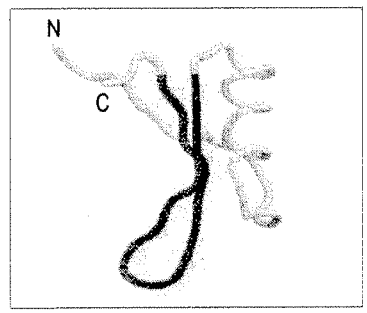
Figure 6H:
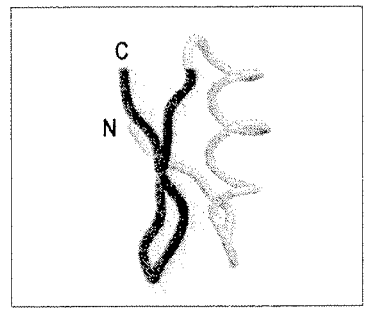
Figure 6I:
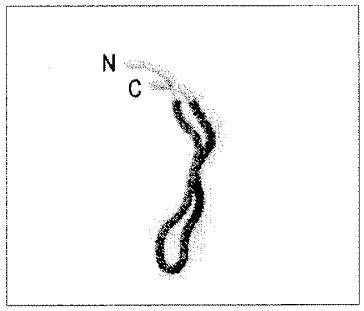

The γ-core motif is a pivotal element in the multidimensional signature of antimicrobial peptides. This motif corresponds to a hydrophobic and structurally rigid region in these molecules. Moreover, the γ-core motif consists of hallmark amino acid sequence, composition, and distribution patterns that likely facilitate antimicrobial functions. For example, patterns identified are congruent with segregation of the most polar or charged residues to solvent-accessible facets, continuity of hydrophilic or hydrophobic surfaces, and flexibility near structural extremities of these peptides. Such physicochemical properties appear to be integral to the antimicrobial mechanisms of disulfide-containing peptides such as the CS-αβ or defensin families (Yeaman and Yount, *Pharmacol. Rev.* 55:27 (2003); Hill et al., *Science* 251:1481 (1991)). Thus, the γ-core motif is more than simply a β-hairpin fold. As described herein, the γ-core component of the antimicrobial peptide signature can be derived from dextromeric or levomeric sequence patterns (FIG. 2B). The necessity for host defense against microbial pathogens has favored conservation of an effective 3-dimensional determinant, despite site- or orientation-specific variations in the primary sequences that comprise this motif. Thus, the present invention provides a method for stereospecific analysis of primary sequences that can identify structural patterns or relationships in any protein class selected by the user.

Figure 8A:
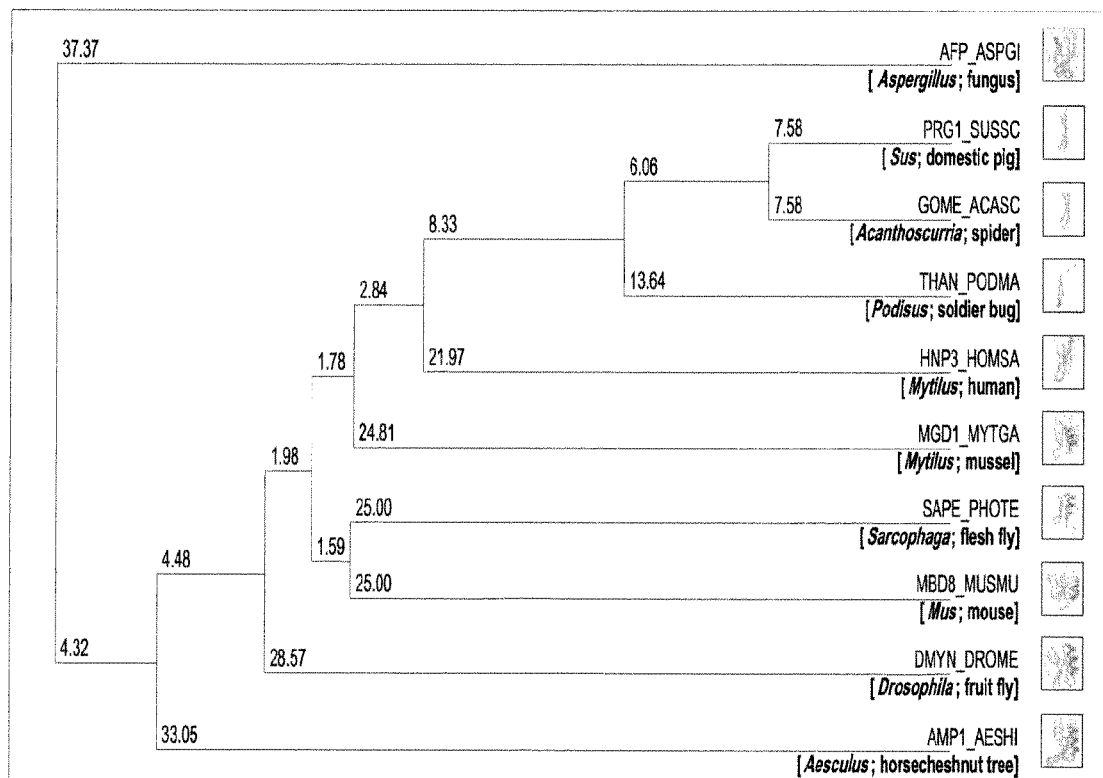
FIG. 8 (A) shows phylogenetic relationship amongst structural signatures in prototypical antimicrobial peptides. Relative evolutionary distances are indicated at branch nodes in this average distance dendrogram (Saito and Nei, *Mol. Biol. Evol.* 4:406 (1987)). Representative peptides for which structures have been determined are (descending order): AFP (AFP-1; *Aspergillus*, fungal); PRG1 (Protegrin-1; *Sus*, domestic pig); GOME (Gomesin; *Acanthoscurria*, spider); THAN (Thanatin; *Podisus*, soldier bug); HNP3 (Human neutrophil peptide-3; *Homo*, human); MGD1 (MGD-1; *Mytilus*, mussel); SAPE (Sapecin; *Sarcophaga*, flesh fly); MBD8 (Murine β-defensin-8; *Mus*, mouse); DMYN (Drosomycin; *Drosophila*, fruit fly); Ah-AMP1 (AMP-1; *Aesculus*, horsechestnut tree). Color schema are the Clustal degree of 2° structure conservation. These data illustrate the concept that the γ-core is the common structural element in these peptides, suggesting it is an archetype motif of the antimicrobial peptide signature (see FIG. 4).

Conservation of the γ-core motif across the phylogenetic spectrum demonstrates it is an archetype of the antimicrobial peptide signature (FIG. 8A). Yet, the γ-core is not necessarily an exclusive structural determinant of antimicrobial activity. In some cases, the γ-core alone is sufficient for antimicrobial activity (eg., protegrins, tachyplesins, RTD-1). However, the motif also can serve as a scaffold, to which complementary antimicrobial determinants (eg., α-helices or β-sheets) are added as adjacent modules.

Thus, disulfide-stabilized antimicrobial peptides represent structural modules coordinated in varying configurations relative to the γ-core (FIG. 8B). Examples of the invention discovery are abundant in nature: Protegrin-1 illustrates the simplest configuration, consisting solely of the γ-core, represented by the modular formula [γ]; MGD-1 contains an α-helical module linked to a γ-core, collectively represented as [γ-α]; alternatively, HNP-3 exemplifies the addition of a β-sheet module to the γ-core, represented as [β-γ]; Ah-AMP-1 illustrates a more complex configuration in which β-sheet and α-helical modules are linked to the γ-core, represented by the formula [β-γ-α]. Permutations of these modular formulae are readily observed in naturally-occurring antimicrobial peptides, encompassing diverse antimicrobial peptide families, including α-defensins, β-defensins, θ-defensins, cathelicidins, protegrins, and CS-αβ peptides found in plants, invertebrates, insects, and arthropods. Based on this discovery the present invention provides methods of utilizing specific mosaic configurations of such structural modules to optimize the function of a given antimicrobial peptide against relevant pathogens in specific physiologic contexts.

Thus, peptides with common evolutionary precursors may have conserved structural elements independent of functional divergence. As one verification of this discovery, AFP-1 and TGF-α were intentionally included in the exemplified phylogenetic and structural analyses as relative outliers in the comparative antimicrobial and non-antimicrobial peptide groups. This level of divergence is reflected in their significant phylogenetic distances from other peptides in their respective subsets. Yet, as described herein, despite equidistant divergence from Ah-AMP-1, AFP-1 exhibits the fundamental γ-core signature of antimicrobial peptides, while TGF-α does not (FIGS. 3 I-L and 8A). This result reinforces the importance of the γ-core motif as part of a multidimensional signature for antimicrobial activity. Moreover, structural divergence of AFP-1 from other antimicrobial peptides lies predominantly in modules beyond the γ-core. Thus, as exemplified for AFP-1, the invention provides new insights into eukaryotic evolution of the multidimensional signature of antimicrobial peptides that confer survival advantages in environments rich in microbial pathogens.

The discovery of a multidimensional signature as described herein can be applied to a method of identifying peptides that exert previously unrecognized antimicrobial activity. As described herein, for example, the sweetener protein, brazzein, and the scorpion neurotoxin, charybdotoxin, were found to have previously unrecognized antimicrobial activity against bacteria and fungi. The present model also accurately predicted that the prototype metallothionein II, which fulfilled the primary sequence pattern, but lacked the 3-dimensional criteria of the antimicrobial signature, was devoid of antimicrobial activity. As described herein, the multidimensional signature model was further substantiated by successful prediction of the γ-core motif in tachyplesins of unknown 3-dimensional structure, but which had known antimicrobial activity, and fulfilled the primary structure criteria of the model. Together, these findings validate the predictive accuracy, utility and applicability of the multidimensional antimicrobial peptide signature model to the methods provided by the present invention.

As disclosed herein, the multidimensional signature is a unifying structural code for broad classes of host defense peptides. This discovery is supported, for example, in the exemplification that a major class of peptides can be retrieved from the protein database searches using the stereospecific sequence formulae consisting of protease inhibitors and related proteins derived from plants (FIG. 11B). The botanical and related literature indicate that several such peptides have been shown to be plant defensins (Sallenave, *Biochem. Soc. Trans.* 30:111 (2002); Wijaya et al., *Plant Sci* 159:243 (2000)). Moreover, the plant proteinase inhibitor superfamily includes thionin peptides containing the antimicrobial γ-core motif as disclosed herein (Table I; Melo et al., *Proteins* 48:311 (2002)). In addition, peptides originally identified as having cytokine bioactivities are now known to have direct antimicrobial activity. Examples include γ-chemokines such as human platelet factor-4 and platelet basic peptide (PF-4 and PBP; Tang et al., *Infect. Immun.* 70:6524 (2002); Yeaman, *Clin. Infect. Dis.* 25:951 (1997)), monokine induced by interferon-γ (MIG/CXCL9; Cole et al., *J. Immunol.* 167:623 (2001)), interferon-γ inducible protein-10 kDa (IP-10/CXCL10; Cole et al., *J. Immunol.* 167:623 (2001)), interferon-inducible T cell α chemoattractant (ITAC/CXCL11; Cole et al., *J. Immunol.* 167:623 (2001)), and the β-chemokine, RANTES (releasable upon activation normal T cell expressed/secreted; Tang et al., *Infect. Immun.* 70:6524 (2002); Yeaman, *Clin. Infect. Dis.* 25:951 (1997)). Importantly, each of these proteins contains an iteration of the multidimensional antimicrobial signature as provided by the present invention. Collectively, these observations demonstrate the link between the multidimensional antimicrobial signature, and functional correlates in multifunctional host defense peptides (Yeaman, *Clin. Infect. Dis.* 25:951 (1997); Ganz, *Science* 298:977 (2002)). The skilled person will appreciate that the multidimensional antimicrobial signature can be found in additional peptides, and that the presence of this signature is associated with antimicrobial activity.

Multidimensional signatures of antimicrobial peptides exemplify how nature can diverge at the level of overall amino acid sequence, yet preserve essential primary sequence patterns and 3-dimensional determinants effective in host defense. Thus, critical structures of antimicrobial peptides from evolutionarily distant organisms such as microbes and plants are recapitulated in higher organisms, including humans. As disclosed herein, vertical and horizontal acquisition of genes, along with their recombination, yield mosaic iterations upon key structural determinants, such as the γ-core motif (Bevins et al., *Genomics* 31:95 (1996); Gudmundsson, et al., *Proc. Natl. Acad. Sci. USA* 92:7085 (1995)). Selective pressures favoring this remarkable degree of structural conservation can include genetic selection against structural variants, and convergent evolution of independent ancestral templates. It follows that the γ-core signature is incorporated into a variety of structural mosaics (eg., [γα$_1$], [γβ$_1$], or [γα$_1$β$_1$]) readily observed amongst disulfide-stabilized antimicrobial peptides along the phylogenetic spectrum. While future studies will resolve their precise phylogenetic lineage, the multidimensional signatures in antimicrobial peptides likely reflect fundamental host-pathogen interactions and their co-evolution.

Figure 16:
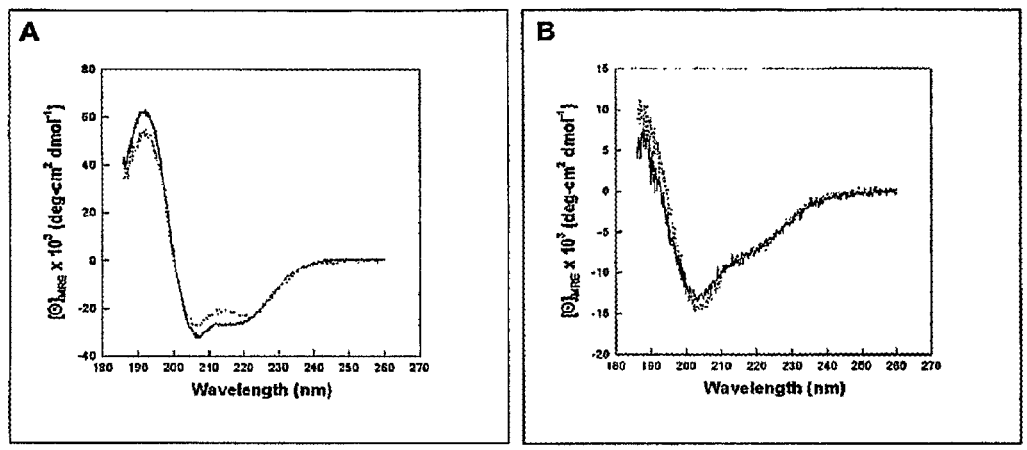
FIG. 16 shows spectroscopy for IL-8 structural domains. Spectra were determined for the IL-8γ and IL-8α peptides (0.1 mM) in sodium phosphate (10.0 mM, pH 5.5) or PIPES (10.0 mM, pH 7.5) buffer. [ . . . ], (IL-8α); [_____], (IL-8-$\gamma_{KC}$).
Figure 17:
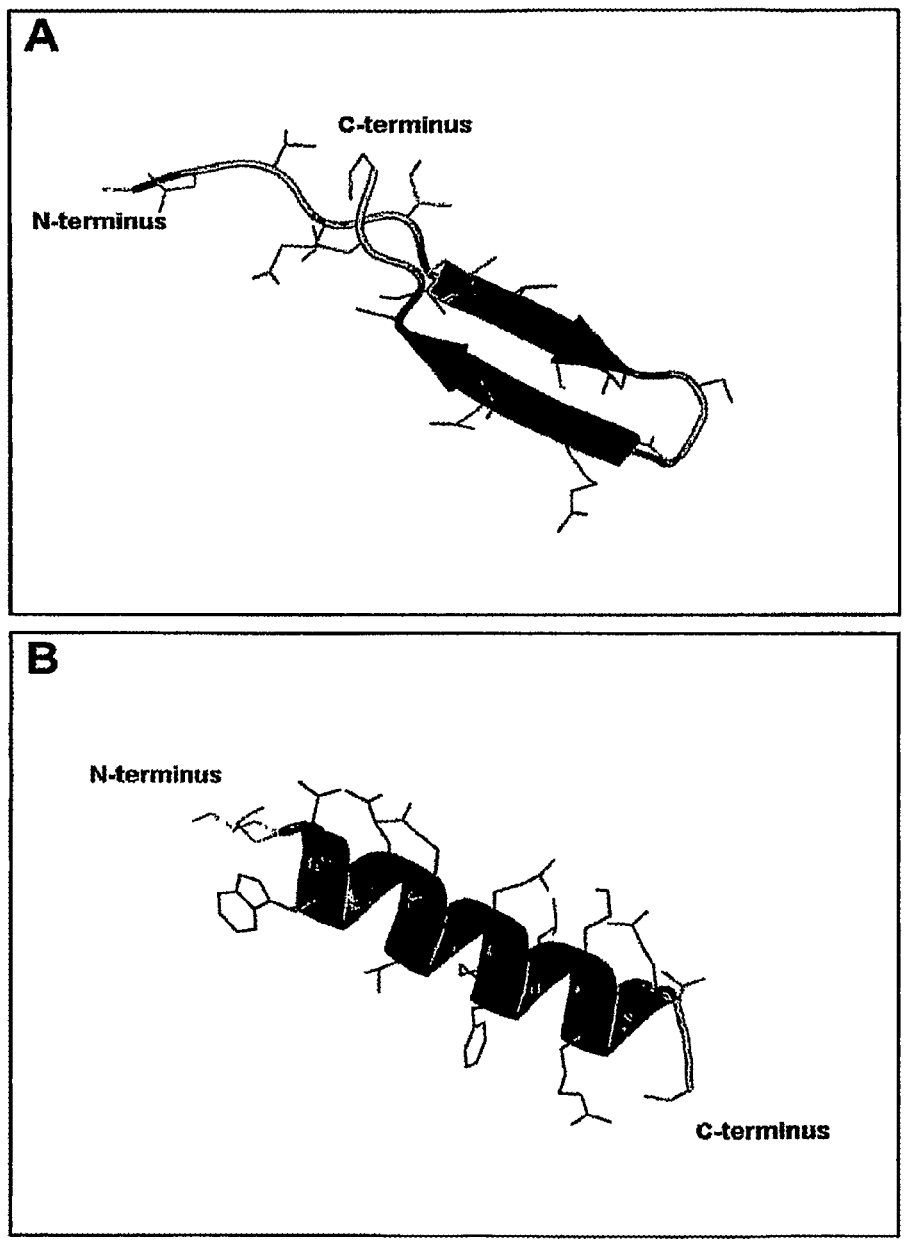
FIG. 17 shows computational modeling of IL-8 structural domains. Three-dimensional models of IL-8α (A) and IL-8γ (B) peptides were created using homology and energy-based methods. Model peptide alpha-carbon backbones were visualized using PyMOL (version 0.97; 2004).

The discovery and characterization of antimicrobial peptide signatures can also provide insights for development of new generation anti-infective agents. For example, most microbial pathogens are unable to acquire rapid or high-level resistance to antimicrobial peptides. Critical structure-activity relationships in these molecules can circumvent microbial resistance mechanisms, and interfere with essential microbial targets distinct from classical antibiotics (Yeaman and Yount, *Pharmacol. Rev.* 55:27 (2003)). Such modes of action exploit pathogen-specific structures intrinsically difficult to mutate, limiting the development of resistance through target or pathway modification. Thus, structural signatures in antimicrobial peptides can advance the discovery and development of improved anti-infective agents and strategies that are refractory to microbial resistance. Therefore, the invention provides a method of improving the antimicrobial activity of a protein by altering the multidimensional signature. Methods of protein design are well known in the art as described, for example, in *Concepts in Protein Engineering and Design: An Introduction*; Wrede and Schneider (Eds.), Walter de Gruyter, Inc. (pub.), 1994); Evolutionary Approaches to Protein Design, Vol. 55, Frances H. Arnold (Ed.), Edward M. Scolnick (Ed.), Elsevier Science & Technology Books, 2000; Molecular Design and Modeling: Concepts and Applications, Part A: Proteins, Peptides, and Enzymes: Volume 202: Molecular Design and Modelling Part A, John N. Abelson (Ed.), John J. Langone (Ed.), Melvin I. Simon (Ed.), Elsevier Science & Technology Books, 1991; and Protein Engineering and Design, Paul R. Carey (Ed.), Elsevier Science & Technology Books, 1996; all of which are incorporated herein by reference in their entirety.

While chemokines have not traditionally been ascribed with direct antimicrobial activities, evidence for such functions is mounting. As described above, peptides originally identified as having cytokine bioactivities, including chemokines platelet factor-4 (PF-4) platelet basic peptide (PBP) and its derivative CTAP-3 (Tang et al. (2002) *Infect Immun* 70, 6524-33; Yeaman et al. (1997) *Infect Immun* 65, 1023-31; Yount et al. (2004) *Antimicrob Agents Chemother* 48, 4395-404), as well as truncations thereof (Krijgsveld et al. (2000) *J Biol Chem* 275, 20374-81), are now known to have direct antimicrobial activity. Direct antimicrobial activity was subsequently reported for other chemokines (Cole et al. (2001) *J Immunol* 167, 623-7; Yang et al. (2003) *J Leukoc Biol* 74, 448-55). Hence, the term kinocidin (kino—action; cidin—microbicidal) has been applied to chemokines that also exert direct microbicidal activity (Yount & Yeaman (2004) *Proc Natl Acad Sci USA* 101, 7363-8; Yount et al. (2004) *Antimicrob Agents Chemother* 48, 4395-404, Yeaman, M. R. & Yount, N. (2005) *ASM News* 71, 21-27).

Despite immunological likeness with other kinocidins, prior investigations have not detected direct antimicrobial activity of IL-8. As described herein, primary sequence and conformation analyses specified IL-8 and kinocidin iterations of the γ-core signature present in broad classes of antimicrobial peptides (Yount & Yeaman (2004) *Proc Natl Acad Sci USA* 101). Based on these structural parallels, IL-8 was discovered to have direct antimicrobial activity. Multiple lines of investigation described herein confirmed that IL-8 exerts significant, context-specific antimicrobial activity, with potent efficacy against *Candida albicans*. Moreover, the invention provides a synthetic congener corresponding to the α-helical domain of IL-8 that exerts antimicrobial activity equivalent to or exceeding that of native IL-8.

As disclosed herein, IL-8 and other kinocidins share key properties with classical antimicrobial peptides. For example, kinocidins exhibit global as well as local amphipathic domains, and have pI values of 8.5 or greater, indicating net positive charge at neutral pH (Table III). However, distribution of charge within kinocidins is not uniform; typically, cationic charge is associated with the C-terminal α-helix, and termini of the IL-8γ core. Molecular modeling has suggested these regions form electropositive facets of varying size in distinct kinocidins (Yang et al. (2003) *J Leukoc Biol* 74, 448-55). It is notable that, while study kinocidins share such cationic properties, neither net charge pI directly correlated with antimicrobial activity. For example, although IL-8 was one of the least cationic kinocidins studied (pI=9.0), it had greater efficacy than many of its more positively charged counterparts.

Recognition that charge alone does not account for antimicrobial activity emphasizes the importance of 3-D structure for kinocidin function. Notably, the strongly anti-fungal kinocidin IL-8 bears a striking structural resemblance to classical antifungal CS-αβ antimicrobial peptides of plants and insects (FIG. 13; Yount & Yeaman (2004) *Proc Natl Acad Sci USA* 101). Kinocidins including IL-8 share a common topology comprised of a $\gamma_{KC}$ core and α-helix. Likewise, CS-αβ family antimicrobial peptides also contain a $\gamma_{AP}$ core and α-helix (Yang et al. (2003) *J Leukoc Biol* 74, 448-55). However, as kinocidins are larger (8-14 kDa) than many classical antimicrobial peptides (<5 kDa), it follows that global physicochemical properties do not strictly correlate with antimicrobial efficacy. Rather, it is more likely that discrete domains likely confer microbicidal versus chemotactic activities for kinocidins or chemotactic antimicrobial peptides (Yeaman & Yount (2005) *ASM News* 71, 21-27).

The fact that the C-terminal IL-8α peptide recapitulated the microbicidal efficacy and spectrum of native IL-8 substantiates the hypothesis that kinocidin antimicrobial effects can be mediated by specific or even autonomous structural domains. Inspection of the IL-8α domain revealed a highly structured helix, with physiochemical features likely attributable to its direct antimicrobial efficacy. Moreover, the current structure analyses concur with independent NMR studies (Clore et al. (1990) *Biochemistry* 29, 1689-96) of the IL-8 α-helix domain. In addition, as its helical conformation is stable at pH 5.5 and 7.5, pH-specific antimicrobial efficacy of IL-8α relies on parameters other than conformation (FIG. 16). Superimposed upon the 19-residue IL-8α domain are cationic charge and amphipathicity (FIG. 17). Its estimated pI of 10 and net charge of +2 (at pH 7) indicate a degree of cationic potential greater than that of corresponding domains in other study kinocidins except lymphotactin. Furthermore, its amphipathicity (6.70; Table 3) is also relatively high, as hydrophobic moments >3.0 are considered significant in terms of hydrophobic versus hydrophilic amino acid segregation. Such characteristics parallel those in well-characterized helical antimicrobial peptides (Wieprecht et al. (1997) *Biochemistry* 36, 6124-32; Uematsu & Matsuzaki. (2000) *Biophys J* 79, 2075-83).

Analyses of the physicochemical properties reveal that kinocidin molecules share key properties with classical antimicrobial peptides. For example, kinocidins exhibit global as well as local amphipathic domains, and have pI values of 8.5 or greater, indicating net positive charge at neutral pH (Table III). However, distribution of charge within kinocidins is not uniform; typically, cationic charge is associated with the C-terminal α-helix, and termini of the IL-8γ core. Molecular modeling has suggested these regions form electropositive facets of varying size in distinct kinocidins (Yang et al. (2003) *J Leukoc Biol* 74, 448-55).

The current results demonstrate direct antimicrobial activities of these and other kinocidins against bacteria in solid-phase and solution-phase assays, including striking fungicidal activity versus *C. albicans*. The surprising discovery of IL-8 antimicrobial efficacy may be due to a number of factors, including organism and/or strain differences, as well as buffer composition and pH. Prior studies using a radial diffusion assay measured activity against different organisms (*Escherichia coli, Listeria monocytogenes*), and did not assess activity at pH 5.5 (11). In the one prior study using a solution-phase assay, activity of IL-8 was evaluated against *E. coli* and *S. aureus* using a phosphate-based buffer system at pH 7.4 (Yang et al. (2003) *J Leukoc Biol* 74, 448-55). Results from these latter experiments corroborate the present finding that native IL-8 lacks activity against *S. typhimurium* or *S. aureus* in solution phase at pH 7.5.

The current investigations demonstrated that IL-8 exerted significant microbicidal efficacy at concentrations descending to the high nM range. While such concentrations reflect relatively strong microbicidal efficacy, it could be argued that even μg/ml levels of activity have limited physiologic relevance. However, several considerations support the concept that the antimicrobial effects of kinocidins including IL-8 observed in vitro are relevant to host defense in vivo. In normal human plasma, IL-8 is present at a very low baseline level in the range of picograms/ml (30). However, in contexts of infection, circulating IL-8 levels rise rapidly and dramatically as much as 1000-fold, yielding concentrations of 30-50 ng/ml (Moller et al. (2005) *J Infect Dis* 191, 768-75). In the current report, IL-8 was active in the 5000-1000 ng/ml range, 100-fold greater than the highest measured concentrations in plasma. Yet, the potential for IL-8 and other kinocidins to reach efficacious concentrations in local contexts of infection is supported by considerable evidence. For example, recent studies by Qiu et al. show that the chemokine CCL22/MDC reaches μg/g levels in lung granulomae (Qiu et al. (2001) *Am J Pathol* 158, 1503-15). Additionally, as kinocidins adhere readily to pathogens, measurements of their free concentration diluted in media or sera almost certainly underestimate their local intensification (Mezzano et al. (1992) *Nephron* 61, 58-63). Also, the systemic administration of α-helical antimicrobial peptides do not preclude their concentration specifically at sites of infection (Nibbering et al. (2004) *J Nucl Med* 45, 321-6), perhaps by affinity of the cationic peptide for electronegative bacterial cell membranes. Such events likely achieve local concentrations of IL-8 and other kinocidins sufficient for microbicidal potency and chemotactic navigation.

In many contexts of infection or inflammation, pH of interstitial fluids, abscess exudates, and serum is significantly lower than that of plasma. Furthermore, recurring host-defense strategies include mild acidification of mucosal epithelia and the neutrophil phagolysosome. Thus, assessment of IL-8 and subdomain antimicrobial efficacy at pH 7.5 versus 5.5 was designed to reflect such microenvironments. The fact that kinocidins, including IL-8 and the IL-8α antimicrobial domain, exert enhanced antimicrobial efficacy at pH 5.5 is consistent with these concepts. Thus, beyond providing a chemical barrier, such pH modulation may contribute to mucosal surfaces that are inhospitable to microbial colonization. A parallel line of reasoning also supports the concept that kinocidins mutually potentiate the antimicrobial mechanisms of leukocytes. Kinocidins are known to interact with leukocytes via chemokine motifs, and with microorganisms via charge-mediated properties (Yang et al. (2003) *J Leukoc Biol* 74, 448-55). Thus, pathogens pre-decorated with kinocidins or antimicrobial domains thereof are believed to be more efficiently killed when internalized into the acidic phagolysosome of professional phagocytes (5). Additional support for this concept is exemplified by studies demonstrating significant quantities of the kinocidin PBP in the phagolysosomes of activated macrophages (34). In these ways, kinocidins are likely evolved to function in specific contexts to optimize antimicrobial defenses without concomitant host toxicity.

Peptides useful as antifungal or antibacterial agents are those which are at least 5 or more, 6 or more, 7 or more, 8 or more, 9 or more, 10 or more, 11 or more, 12 or more, 13 or more, 14 or more, 15 or more amino acids in length and which comprise at least a portion of the alpha-helical structure sufficient for antimicrobial activity, and substitutions thereof. An example of a permissible substitutions is alanine for cysteine.

The peptides of the present invention can be chemically synthesized. Thus polypeptides can be prepared by solid phase peptide synthesis, for example as described by Merrifield. The synthesis is typically carried out with amino acids that are protected at the alpha-amino terminus. Trifunctional amino acids with labile side-chains are also protected with suitable groups to prevent undesired chemical reactions from occurring during the assembly of the polypeptides. The alpha-amino protecting group is selectively removed to allow subsequent reaction to take place at the amino-terminus. The conditions for the removal of the alpha-amino protecting group do not remove the side-chain protecting groups.

The alpha-amino protecting groups are well known to those skilled in the art and include acyl type protecting groups (e.g., formyl, trifluoroacetyl, acetyl), aryl type protecting groups (e.g., biotinyl), aromatic urethane type protecting groups [e.g., benzyloxycarbonyl (Cbz), substituted benzyloxycarbonyl and 9-fluorenylmethyloxy-carbonyl (Fmoc)], aliphatic urethane protecting groups [e.g., t-butyloxycarbonyl (tBoc), isopropyloxycarbonyl, cyclohexloxycarbonyl] and alkyl type protecting groups (e.g., benzyl, triphenylmethyl). The preferred protecting groups are tBoc and Fmoc.

The side-chain protecting groups selected must remain intact during coupling and not be removed during the deprotection of the amino-terminus protecting group or during coupling conditions. The side-chain protecting groups are also removable upon the completion of synthesis using reaction conditions that will not alter the finished polypeptide. In tBoc chemistry, the side-chain protecting groups for trifunctional amino acids are mostly benzyl based. In Fmoc chemistry, they are mostly tert-butyl or trityl based.

In addition, the peptides can also be prepared by recombinant DNA technologies wherein host cells are transformed with proper recombinant plasmids containing the nucleotide sequence encoding the particular peptide. The peptides of the present invention can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are well known in the art and can be found in standard references as Sambrook et al., *Molecular Cloning: A Laboratory Manual*, Third Ed., Cold Spring Harbor Laboratory, New York (2001) and Ansubel et al., *Current Protocols in Molecular Biology*, John Wiley and Sons, Baltimore, Md. (1999), both of which are incorporated herein by reference.

In general, a DNA sequence encoding a peptide of the present invention is operably linked to other genetic elements required for its expression, generally including a transcription promoter and terminator within an expression vector. The vector typically contains one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are available through commercial suppliers.

The peptides of the present invention can be formulated into compositions in pharmaceutically acceptable carriers for administration to individuals. For oral administration, the peptides can be formulated into a solid preparation such as tablets, pills, granules, powder, capsules and the like, or a liquid preparation such as solutions, suspensions, emulsions and the like. The pharmaceutical preparations for oral administration comprising one or more peptides of the present invention may also contain one or more of the following customary excipients: fillers and extenders including starches, lactose, sucrose, glucose, mannitol and silica; binders including carboxymethylcellulose, alginates, gelatine and polyvinylpyrrolidone; humectants including glycerine; disintegrating agents, including agar-agar, calcium carbonate and sodium carbonate; solution retarders, including paraffin; absorption accelerators including quaternary ammonium compound; wetting agents including cetyl alcohol or glycerine monostearate; adsorbents including kaolin and bentonite; lubricants including talc, calcium stearate and magnesium stearate and solid polyethylene glycols; colorants; flavorings; and sweeteners.

When the preparation is used for parental administration, the preparation is made in an injection formula. For the preparation of an injection formula, the solutions and emulsions can be in a sterile form which is isotonic with blood. The suspensions can contain in addition to the active peptide or peptides, preservatives, stabilizers, solubilizers, wetting agents, salts for changing the osmotic pressure or buffers.

The peptides of the present invention are useful as antifungal or antibacterial agents.

The invention provides methods of using kinocidin peptide constructs such as IL-8α for treating a subject suffering from infection (including fungal, bacterial, or other microbial infection), especially mammalian subjects such as humans, but also including farm animals such as cows, sheep, pigs, horses, goats and/or poultry (e.g., chickens, turkeys, ducks and/or geese), companion animals such as dogs and/or cats, exotic and/or zoo animals, and/or laboratory animals including mice, rats, rabbits, guinea pigs, and/or hamsters. Immunocompromised or immunosuppressed subjects, e.g., subjects suffering from cancer, subjects undergoing radiation therapy and/or cytotoxic chemotherapy, subjects being treated with immunosuppressive drugs, and/or subjects suffering from natural or acquired immune deficiencies such as AIDS, may be treated according to this aspect of the invention. Treatment of infection of plants is also contemplated.

"Treatment" as used herein encompasses both prophylactic and/or therapeutic treatment, and may be accompanied by concurrent administration of other antimicrobial agents, including any of the agents discussed herein.

Fungal infection that may be treated according to the invention may be caused by a variety of fungal species including *Candida* (including *C. albicans, C. tropicalis, C. parapsilosis, C. stellatoidea, C. krusei, C. parakrusei, C. lusitanae, C. pseudotropicalis, C. guilliermondi, C. dubliniensis, C. famata* or *C. glabrata*), *Aspergillus* (including *A. fumigatus, A. flavus, A. niger, A. nidulans, A. terreus, A. sydowi, A. flavatus,* or *A. glaucus*), *Cryptococcus, Histoplasma, Coccidioides, Paracoccidioides, Blastomyces, Basidiobolus, Conidiobolus, Rhizopus, Rhizomucor, Mucor, Absidia, Mortierella, Cunninghamella, Saksenaea, Pseudallescheria, Paecilomyces, Fusarium, Trichophyton, Trichosporon, Microsporum, Epidermophyton, Scytalidium, Malassezia, Actinomycetes, Sporothrix, Penicillium, Saccharomyces* or *Pneumocystis*.

Other infections that may be treated using a peptide construct according to the invention may be caused by gram-negative bacterial species that include *Acidaminococcus, Acinetobacter, Aeromonas, Alcaligenes, Bacteroides, Bordetella, Branhamella, Brucella, Burkholderia, Calymmatobacterium, Campylobacter, Cardiobacterium, Chromobacterium, Citrobacter, Edwardsiella, Enterobacter, Escherichia, Flavobacterium, Francisella, Fusobacterium, Haemophilus, Klebsiella, Legionella, Moraxella, Morganella, Neisseria, Pasturella, Plesiomonas, Porphyromonas, Prevotella, Proteus, Providencia, Pseudomonas, Salmonella, Serratia, Shigella, Stentrophomonas, Streptobacillus, Treponema, Veillonella, Vibrio,* or *Yersinia* species; *Chlamydia*; or gram-positive bacterial species that include *Staphylococcus, Streptococcus, Micrococcus, Peptococcus, Peptostreptococcus, Enterococcus, Bacillus, Clostridium, Lactobacillus, Listeria, Erysipelothrix, Propionibacterium, Eubacterium, Nocardia, Actinomyces,* or *Corynebacterium* species as well as *Mycoplasma, Ureaplasma,* or *Mycobacteria*.

Other infections include infections by protozoa including *Plasmodia, Toxoplasma, Leishmania, Trypanosoma, Giardia, Entamoeba, Acanthamoeba, Nagleria, Hartmanella, Balantidium, Babesia, Cryptosporidium, Isospora, Microsporidium, Trichomonas* or *Pneumocystis* species; or infections by other parasites include helminths.

Other therapeutic uses of kinocidin peptide constructs such as IL-8α according to the invention include methods of treating conditions associated with endotoxin, such as exposure to gram-negative bacterial endotoxin in circulation, endotoxemia, bacterial and/or endotoxin-related shock and one or more conditions associated therewith, including a systemic inflammatory response, cytokine overstimulation, complement activation, disseminated intravascular coagulation, increased vascular permeability, anemia, thrombocytopenia, leukopenia, pulmonary edema, adult respiratory distress syndrome, renal insufficiency and failure, hypotension, fever, tachycardia, tachypnea, and metabolic acidosis. Thus, not only gram-negative bacterial infection but also conditions which are associated with exposure to gram-negative bacterial endotoxin (infection-related conditions) may be ameliorated through endotoxin-binding or endotoxin-neutralizing activities of kinocidin peptide constructs such as IL-8α.

Therapeutic compositions of the peptide construct may include a pharmaceutically acceptable diluent, adjuvant, or carrier. The peptide construct may be administered without or in conjunction with known surfactants, other chemotherapeutic agents or additional known antimicrobial agents.

Compositions, including therapeutic compositions, of the peptide construct of the invention may be administered systemically or topically. Systemic routes of administration include oral, intravenous, intramuscular or subcutaneous injection (including into depots for long-term release), intraocular or retrobulbar, intrathecal, intraperitoneal (e.g. by intraperitoneal lavage), intrapulmonary (using powdered drug, or an aerosolized or nebulized drug solution), or transdermal. Topical routes include administration in the form of rinses, washes, salves, creams, jellies, drops or ointments (including opthalmic and otic preparations), suppositories, such as vaginal suppositories, or irrigation fluids (for, e.g., irrigation of wounds).

Suitable dosages include doses ranging from 1 mg/kg to 100 mg/kg per day and doses ranging from 0.1 mg/kg to 20 mg/kg per day. When given parenterally, compositions are generally injected in one or more doses ranging from 1 mg/kg to 100 mg/kg per day, preferably at doses ranging from 0.1 mg/kg to 20 mg/kg per day, and more preferably at doses ranging from 1 to 20 mg/kg/day. As described herein for compositions with IL-8α, parenteral doses of 0.5 to 5 mg/kg/day are preferred according to the present invention. The treatment may continue by continuous infusion or intermittent injection or infusion, or a combination thereof, at the same, reduced or increased dose per day for as long as determined by the treating physician. An antimicrobial composition can be effective at blood serum concentrations as low as 1 µg/ml. When given topically, compositions are generally applied in unit doses ranging from 1 mg/mL to 1 gm/mL, and preferably in doses ranging from 1 mg/mL to 100 mg/mL. Decontaminating doses are applied including, for example, for fluids or surfaces or to decontaminate or sterilize surgical or other medical equipment or implantable devices, including, for example prosthetic joints or in indwelling invasive devices. Those skilled in the art can readily optimize effective dosages and administration regimens for therapeutic, including decontaminating, compositions as determined by good medical practice and the clinical condition of the individual subject.

"Concurrent administration," or "co-administration," as used herein includes administration of one or more agents, in conjunction or combination, together, or before or after each other. The agents maybe administered by the same or by different routes. If administered via the same route, the agents may be given simultaneously or sequentially, as long as they are given in a manner sufficient to allow all agents to achieve effective concentrations at the site of action. For example, a peptide construct may be administered intravenously while the second agent(s) is(are) administered intravenously, intramuscularly, subcutaneously, orally or intraperitoneally. A peptide construct and a second agent(s) may be given sequentially in the same intravenous line or may be given in different intravenous lines. Alternatively, a peptide construct may be administered in a special form for gastric or aerosol delivery, while the second agent(s) is(are) administered, e.g., orally.

Concurrent administration of the peptide construct of the invention, such as IL-8α, for adjunctive therapy with one or more other antimicrobial agents (particularly antifungal agents) is expected to improve the therapeutic effectiveness of the antimicrobial agents. This may occur through reducing the concentration of antimicrobial agent required to eradicate or inhibit target cell growth, e.g., replication. Because the use of some antimicrobial agents is limited by their systemic toxicity, lowering the concentration of antimicrobial agent required for therapeutic effectiveness reduces toxicity and allows wider use of the agent. For example, concurrent administration of the peptide construct, such as IL-8α, and another antifungal agent may produce a more rapid or complete fungicidal or fungistatic effect than could be achieved with either agent alone. Administration of the peptide construct, such as IL-8α, may reverse the resistance of fungi to antifungal agents or may convert a fungistatic agent into a fungicidal agent. Similar results may be observed upon concurrent administration of the peptide construct, such as IL-8α, with other antimicrobial agents, including antibacterial and/or anti-endotoxin agents.

Therapeutic effectiveness in vivo is based on a successful clinical outcome, and does not require that the antimicrobial agent or agents kill 100% of the organisms involved in the infection. Success depends on achieving a level of antimicrobial activity at the site of infection that is sufficient to inhibit growth or replication of the pathogenic organism in a manner that tips the balance in favor of the host. When host defenses are maximally effective, the antimicrobial effect required may be minimal. Reducing organism load by even one log (a factor of 10) may permit the host's own defenses to control the infection. In addition, augmenting an early microbicidal/microbistatic effect can be more important than a long-term effect. These early events are a significant and critical part of therapeutic success, because they allow time for host defense mechanisms to activate.

In addition, the invention provides a method of killing or inhibiting growth of pathogenic organisms (particularly fungi) comprising contacting the organism with the peptide construct, such as IL-8α, optionally in conjunction with other antimicrobial agents. This method can be practiced in vivo, ex vivo, or in a variety of in vitro uses such as to decontaminate fluids or surfaces or to sterilize surgical or other medical equipment or implantable devices, including prostheses or intrauterine devices. These methods can also be used for in situ decontamination and/or sterilization of indwelling invasive devices such as intravenous lines and catheters, which are often foci of infection.

A further aspect of the invention involves use of the peptide construct, such as IL-8α, for the manufacture of a medicament for treatment of microbial infection (e.g., fungal or bacterial infection) or a medicament for concurrent administration with another agent for treatment of microbial infection. The medicament may optionally comprise a pharmaceutically acceptable diluent, adjuvant or carrier and also may include, in addition to the kinocidin peptide construct, other chemotherapeutic agents.

Known antifungal agents which can be co-administered or combined with the kinocidin peptide construct according to the invention include polyene derivatives, such as amphotericin B (including lipid or liposomal formulations thereof) or the structurally related compounds nystatin or pimaricin; flucytosine (5-fluorocytosine); azole derivatives (including ketoconazole, clotrimazole, miconazole, econazole, butoconazole, oxiconazole, sulconazole, tioconazole, terconazole, fluconazole, itraconazole, voriconazole [Pfizer], posaconazole [SCH56592, Schering-Plough]) or ravuconazole [Bristol-Myers Squibb]; allylamines-thiocarbamates (including tolnaftate, naftifine or terbinafine); griseofulvin; ciclopirox; haloprogin; echinocandins (including caspofungin [MK-0991, Merck], FK463 [Fujisawa], cilofungin [Eli Lilly] or VER-002 [Versicor]); nikkomycins; or sordarins.

The polyene derivatives, which include amphotericin B or the structurally related compounds nystatin or pimaricin, are broad-spectrum antifungals that bind to ergosterol, a component of fungal cell membranes, and thereby disrupt the membranes. Amphotericin B is usually effective for systemic mycoses, but its administration is limited by toxic effects that include fever, kidney damage, or other accompanying side effects such as anemia, low blood pressure, headache, nausea, vomiting or phlebitis. The unrelated antifungal agent flucytosine (5-fluorocytosine), an orally absorbed drug, is frequently used as an adjunct to amphotericin B treatment for some forms of candidiasis or cryptococcal meningitis. Its adverse effects include bone marrow depression, including with leukopenia or thrombocytopenia.

Known antibacterial agents which can be co-administered or combined with the peptide construct according to the invention include antibiotics, which are natural chemical substances of relatively low molecular weight produced by various species of microorganisms, such as bacteria (including *Bacillus* species), actinomycetes (including *Streptomyces*) or fungi, that inhibit growth of or destroy other microorganisms. Substances of similar structure and mode of action may be synthesized chemically, or natural compounds may be modified to produce semi-synthetic antibiotics. These biosynthetic and semi-synthetic derivatives are also effective as antibiotics. The major classes of antibiotics include (1) the β-lactams, including the penicillins, cephalosporins or monobactams, including those with β-lactamase inhibitors; (2) the aminoglycosides, e.g., gentamicin, tobramycin, netilmycin, or amikacin; (3) the tetracyclines; (4) the sulfonamides and/or trimethoprim; (5) the quinolones or fluoroquinolones, e.g., ciprofloxacin, norfloxacin, ofloxacin, moxifloxacin, trovafloxacin, grepafloxacin, levofloxacin or gatifloxacin (6) vancomycin; (7) the macrolides, which include for example, erythromycin, azithromycin, or clarithromycin; or (8) other antibiotics, e.g., the polymyxins, chloramphenicol, rifampin, the lincosamides, or the oxazolidinones.

Some drugs, for example, aminoglycosides, have a small therapeutic window. For example, 2 to 4 μg/ml of gentamicin or tobramycin may be required for inhibition of bacterial growth, but peak concentrations in plasma above 6 to 10 μg/ml may result in ototoxicity or nephrotoxicity. These agents are more difficult to administer because the ratio of toxic to therapeutic concentrations is very low. Antimicrobial agents that have toxic effects on the kidneys and that are also eliminated primarily by the kidneys, such as the aminoglycosides or vancomycin, require particular caution because reduced elimination can lead to increased plasma concentrations, which in turn may cause increased toxicity. Doses of antimicrobial agents that are eliminated by the kidneys must be reduced in patients with impaired renal function. Similarly, dosages of drugs that are metabolized or excreted by the liver, such as erythromycin, chloramphenicol, or clindamycin, must be reduced in patients with decreased hepatic function. In situations where an antimicrobial agent causes toxic effects, the kinocidin peptide construct, such as IL-8α, can act to reduce the amount of this antimicrobial agent needed to provide the desired clinical effect.

The susceptibility of a bacterial species to an antibiotic is generally determined by any art recognized microbiological method. A rapid but crude procedure uses commercially available filter paper disks that have been impregnated with a specific quantity of the antibiotic drug. These disks are placed on the surface of agar plates that have been streaked with a culture of the organism being tested, and the plates are observed for zones of growth inhibition. A more accurate technique, the broth dilution susceptibility test, involves preparing test tubes containing serial dilutions of the drug in liquid culture media, then inoculating the organism being tested into the tubes. The lowest concentration of drug that inhibits growth of the bacteria after a suitable period of incubation is reported as the minimum inhibitory concentration.

The resistance or susceptibility of an organism to an antibiotic is determined on the basis of clinical outcome, i.e., whether administration of that antibiotic to a subject infected by that organism will successfully cure the subject. While an organism may literally be susceptible to a high concentration of an antibiotic in vitro, the organism may in fact be resistant to that antibiotic at physiologically realistic concentrations. If the concentration of drug required to inhibit growth of or kill the organism is greater than the concentration that can safely be achieved without toxicity to the subject, the microorganism is considered to be resistant to the antibiotic. To facilitate the identification of antibiotic resistance or susceptibility using in vitro test results, the National Committee for Clinical Laboratory Standards (NCCLS) has formulated standards for antibiotic susceptibility that correlate clinical outcome to in vitro determinations of the minimum inhibitory concentration of antibiotic.

Other aspects and advantages of the present invention will be understood upon consideration of the following illustrative examples.

It is understood that modifications which do not substantially affect the activity of the various embodiments of this invention are also included within the definition of the invention provided herein. Accordingly, the following examples are intended to illustrate but not limit the present invention.

Example I

Identification of Multidimensional Signatures of Antimicrobial Peptides

This Example shows identification of a disulfide-stabilized core motif that is integral to the 3-dimensional signature of cysteine-containing antimicrobial peptides.

The relatedness amongst primary structures was examined in prototypic cysteine-containing antimicrobial peptide sequences representing taxa spanning an evolutionary distance of 2.6 billion years (BY; estimated date of phylogenetic divergence of fungi and plants from higher organisms; Nei et al., *Proc. Natl. Acad. Sci. USA*. 98:2497 (2001)). A prototype from each class of non-cyclic, disulfide-containing antimicrobial peptides was represented in these analyses [Antimicrobial peptides were selected from the National Center for Biotechnology Information (NCBI) Entrez Protein (www.ncbi.nlm.nih.gov:80/entrez/) or Antimicrobial Sequences (www.bbcm.univ.trieste.it/~tossi/) databases.]

The specific criteria for selection of peptides analyzed included: 1) eukaryotic origin; 2) published antimicrobial activity; 3) non-enzymatic mechanism(s) of action; 4) mature protein sequence; and 5) less than 75 amino acids in length. Peptides for which structures have been determined were used in structural analyses. [Peptides were selected from the National Center for Biotechnology Information (NCBI) structure (www.ncbi.nlm.nih.gov:80/entrez/) and Protein Data Bank (PDB) (www.rcsb.org/pdb/) resources.] The resulting study set included antimicrobial peptides encompassing a broad distribution in source (i.e., biological kingdoms ranging from microorganisms to man), amino acid sequence, and conformation class (FIG. 1). Amino acid sequence data were used for these analyses, as not all nucleotide sequences have been characterized, and saturation of nucleotide sequence data occurs within non-mitochondrial sequences over evolutionary timescales.

FIG. 1 shows conventional antimicrobial peptide structure classification and distribution. The relationship amongst structure and predominance is summarized for the commonly recognized antimicrobial peptide classes. Concatenation represents the proportionate distribution of peptides encompassing a given structural class, as calculated from the Antimicrobial Sequences Database. Antimicrobial peptides were selected from the National Center for Biotechnology Information (NCBI) Entrez Protein (www.ncbi.nlm.nih.gov:80/entrez/) or Antimicrobial Sequences (www.bbcm.univ.triestelt/~tossi/) databases. The numbers of peptides classified in each group are indicated in brackets for each class. Of the more than 750 peptides present in the database at the onset of the study, the balance of those not indicated are comprised of peptides representing unusual or other classifications, including macrocyclic, proline-rich, tryptophan-rich or indolicidin-like peptides, and large polypeptides greater than 75 amino acids in length.

Representatives included antimicrobial peptides from taxa encompassing broad biological diversity spanning an evolutionary distance of 2.6 billion years (estimated divergence of fungi and plants from higher organisms; [Nei et al, *Proc. Natl. Acad. Sci. USA* 98:2497 (2001).]). This dataset included prototypes of all major classes of disulfide-containing antimicrobial peptides, including distinct conformation groups such as defensin, cysteine-stabilized αβ, ranabox and β-hairpin.

Conventional MSA (N to C terminal; dextromeric) revealed no clear consensus patterns amongst primary sequences of the antimicrobial peptide study set. However, visual inspection revealed an absolutely conserved GXC motif, oriented in reverse in some peptides. We hypothesized that conventional MSA failed to recognize this inverted consensus pattern. Therefore, peptides containing inverted GXC motifs were aligned in their C to N terminal (levomeric) orientation. This stereospecific MSA revealed a novel and striking sequence pattern common to all disulfide-containing antimicrobial peptide classes (FIG. 2B). The consensus patterns, defined herein as the enantiomeric sequence signature, adhere to the formulae:

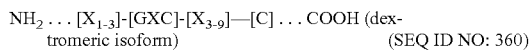
NH$_2$ ... [X$_{1-3}$]-[GXC]-[X$_{3-9}$]—[C] ... COOH (dextromeric isoform)　　　　　　　　　(SEQ ID NO: 360)

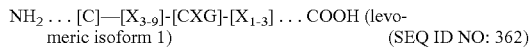
NH$_2$ ... [C]—[X$_{3-9}$]-[CXG]-[X$_{1-3}$] ... COOH (levomeric isoform 1)　　　　　　　　　(SEQ ID NO: 362)

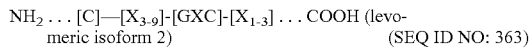
NH$_2$ ... [C]—[X$_{3-9}$]-[GXC]-[X$_{1-3}$] ... COOH (levomeric isoform 2)　　　　　　　　　(SEQ ID NO: 363)

These consensus patterns transcend defensin-specific motifs identified previously (White et al., *Curr. Opin. Struct. Biol.* 5:521 (1995); Yount et al., *J. Biol. Chem.* 274:26249 (1999). Specific characteristics of the enantiomeric sequence signatures include: i) a length of 8-16 amino acid residues; and ii) conserved GXC or CXG motifs within the sequence isoforms. Interestingly, levomeric isoform 2 peptides retain a dextromeric GXC motif within the levomeric sequence signature (FIG. 2B).

Identification of the conserved enantiomeric signature suggested that a corresponding motif would also be present in the 3-dimensional structures of disulfide-stabilized antimicrobial peptides. Conformation alignments revealed a core motif that was absolutely conserved across all classes of disulfide-stabilized antimicrobial peptides (FIG. 3A-H; Table 1). This 3-dimensional archetype, termed herein as the γ-core motif, is comprised of two anti-parallel β-sheets, interposed by a short turn region (FIGS. 4 and 5). All three isoforms of the enantiomeric sequence signature conform to the γ-core motif, reflecting their 3-dimensional convergence (FIG. 5). Additional features that characterize the γ-core include: 1) net cationic charge (+0.5 to +7) with basic residues typically polarized along its axis; 2) periodic charge and hydrophobicity yielding amphipathic stereogeometry; and 3) participation in 1-4 disulfide bonds. This motif may comprise the entire peptide, or link to adjacent structural domains.

Relative to the γ-core, disulfide-stabilized antimicrobial peptides of evolutionarily distant organisms exhibited a striking convergence in conformation, that was essentially isomeric, or at a minimum, highly homologous (FIG. 3). This 3-dimensional convergence encompassed overall conformations, or localized to specific domains in comparative peptides. For example, the structures of Ah-AMP-1 (horsechestnut tree, *Aesculus*) and drosomycin (fruit fly, *Drosophila*) are essentially superimposable over their entire backbone trajectories (FIG. 3C). Alternatively, protegrin-1 (domestic pig, *Sus*) and Ah-AMP-1 share conformational homology corresponding to their γ-core motifs (FIG. 3A). As anticipated, magainin aligned to the α-helical motif in Ah-AMP-1 (FIG. 3G), verifying the specificity of conformational alignments.

To confirm the significance of 3-dimensional convergence in the antimicrobial peptide signature, comparisons between representative cysteine-containing antimicrobial and non-antimicrobial peptides of equivalent molecular weight were performed and analyzed. Outcomes emphasize that non-antimicrobial peptides fail to achieve the multidimensional signature of antimicrobial peptides (FIG. 3I-L). Mean quantitative RMSD confirmed the statistical significance of the differences between antimicrobial and non-antimicrobial structures (Table II).

TABLE II

Quantitative analysis of 3-dimensional convergence amongst prototypic antimicrobial peptide structures.

|  | AAs | RMSD (Å) | Identity (%) | Align/Gap |
|---|---|---|---|---|
| Antimicrobial Peptides |  |  |  |  |
| Ah-AMP-1 (*Aesculus*; Tree; 1BK8; Wieprecht et al. (1997) *Biochemistry* 36, 6124-32) | 50 | 0.0 | 100 | 50/0 |
| Sapecin (*Sarcophaga*; Fly; 1L4V; Uematsu, N. & Matsuzaki K. (2000) *Biophys J* 79, 2075-83 ) | 40 | 0.9 | 25.0 | 38/0 |

TABLE II-continued

Quantitative analysis of 3-dimensional convergence amongst prototypic antimicrobial peptide structures.

| | AAs | RMSD (Å) | Identity (%) | Align/Gap |
|---|---|---|---|---|
| Protegrin-1 (Sus: Pig; 1PG1; Fahrner et al., Chem. Biol. 3: 543 (1996)) | 19 | 1.2 | 18.8 | 16/0 |
| Drosomycin (Drosophila; Fruit Fly; 1MYN; Landon et al., Protein Sci. 6: 1878 (1997)) | 44 | 1.4 | 29.3 | 41/6 |
| Defensin (Raphanus; Radish; 1AYJ; Fant et al., J. Mol. Biol. 279: 257 (1998)) | 51 | 1.3 | 47.6 | 49/0 |
| Thionin (Triticalis; Wheat; 1GPS; Bruix et al., Biochemistry 32: 715 (1993)) | 47 | 1.8 | 26.1 | 46/3 |
| MGD-1 (Mytilus; Mussel; 1FJN; Yang et al., Biochemistry 39: 14436 (2000)) | 39 | 2.0 | 26.5 | 34/1 |
| Thanatin (Podisus; Soldier Bug; 8TFV; Mandard et al., Eur. J. Biochem. 256: 404 (1998)) | 21 | 2.2 | 12.5 | 16/0 |
| HNP-3 (Homo; Human; 1DFN; Hill et al., Science 251: 1481 (1991)) | 34 | 3.2 | 8.3 | 24/17 |
| MBD-8 (Mus: Mouse; 1E4R; Bauer et al., Protein Sci. 10: 2470 (2001)) | 35 | 3.4 | 0.0 | 24/13 |
| AFP-1 (Aspergillus; Fungus; 1AFP; Campos-Olivas et al., Biochemistry 34: 3009 (1995)) | 51 | 4.8 | 6.2 | 32/7 |
| Mean ± SD | | 2.2 ± 1.2* | | |
| Non-Antimicroblal Peptides | | | | |
| TGF-α (Homo; Human; 3TGF; Harvey et al., Eur. J. Biochem. 198: 555 (1991)) | 50 | 4.7 | 3.1 | 32/7 |
| Metallothionein (Saccharomyces; Yeast; 1AOO; Peterson et al., FEBS Lett. 379: 85 (1996)) | 40 | 5.3 | 18.8 | 32/16 |
| Allergen-5 (Ambrosia; Ragweed; 2BBG; Metzler et al., Biochemistry 31: 5117 (1992)) | 40 | 6.5 | 18.8 | 32/7 |
| Ferredoxin (Clostridium; Bacteria; 2FDN; Dauter et al., Biochemistry 36: 16065 (1997)) | 55 | 7.4 | 5.0 | 40/6 |
| Mean ± SD | | 6.0 ± 1.2* | | |

Briefly, three-dimensional alignments of representative antimicrobial and control non-antimicrobial peptide structures were analyzed by pairwise comparison with Ah-AMP-1 (Aesculus; horsechestnut tree; 1BK8) using the combinatorial extension method (Shindyalov and Bourne, Protein Eng. 11:739 (1998)). Control peptides were selected from a cohort of 54 appropriate comparators based on disulfide content, sequence length, and molecular weight equivalence to Ah-AMP-1. Representative results are shown. The comparative length of each mature peptide is indicated as the number of amino acids (AAs). Root Mean Square Deviation (RMSD) values were determined for distances between α-carbon atoms over the length of the alignment. Percent identity is the percentage of sequence identity between the two peptides compared. The align/gap value indicates the number of residues considered for the alignment, and the number of gaps inserted. Relative gap penalties were integrated into the analysis. Mean RMSD values from antimicrobial versus non-antimicrobial peptides were significantly different (*) as determined by two tailed T-test (P<0.01). Information for each structure is formatted as follows: peptide name, (source genus; common name; Protein Data Bank [PDB] accession code; reference).

A highly conserved, disulfide-stabilized core motif was discovered to be integral to the 3-dimensional signature of cysteine-containing antimicrobial peptides. This feature is termed herein as the gamma-core motif (γ-core; FIG. 5). This structural motif is comprised of two anti-parallel β-sheets interposed by a short turn region. Notably, as shown in FIG. 4, the sequence patterns corresponding to the γ-core signature extends across the entire range of antimicrobial peptide families. Exemplary peptides included within the groups are: gomesin ([1KFP], Acanthoscurria, spider, (γ-Group); Mandard et al., Eur. J. Biochem. 269:1190 (2002)); protegrin-1 ([1PG1], Sus, domestic pig, (γ-Group)); thanatin ([8TFV], Podisus, soldier bug, (γ-Group)); α-defensin (HNP-3, [1DFN]; Homo, human, (β-γ-Group); β-defensin (MBD-8, [1E4R], Mus, mouse, (β-γ-Group)); fungal peptide (AFP-1, [1AFP], Aspergillus, fungus, (β-γ-αGroup); insect-defensin (sapecin, [1L4V], Sarcophaga, flesh fly, (γ-α-Group)); crustacean CS-αβ peptide (MGD-1, [1FJN], Mytilus, mussel, (γ-α-Group)); insect CS-αβ peptide (drosomycin, [1MYN], Drosophila, fruit fly, (γ-α-Group)); and plant CS-αβ peptide (Ah-AMP-1, [1BK8] Aesculus, horsechestnut tree, (β-γ-αGroup). Other peptide data are formatted as in FIG. 3. See Table II for additional references. The conserved GXC (dextromeric) or CXG (levomeric) sequence patterns (FIG. 2B) are integrated into one β-sheet in this motif, reflecting conformational symmetry amongst antimicrobial peptides containing this signature (FIG. 5, respectively). Additional features that distinguish the γ-core include: 1) hydrophobic bias toward the C-terminal aspect; and 2) cationic charge positioned at the inflection point and termini of the β-sheet domains, polarizing charge along the longitudinal axis of the γ-core.

Example II

Validation of the Multidimensional Antimicrobial Peptide Signature Model

The multidimensional signature model for antimicrobial peptides integrates a stereospecific (dextromeric or levomeric) sequence pattern with the 3-dimensional gamma-core ("γ-core"). Therefore, this model predicted that peptides fulfilling these prerequisites would exert antimicrobial activity, even though such activity may not yet have been determined.

Multiple and complementary approaches were used to test the model in this regard: 1) prediction of antimicrobial activity in peptides fulfilling the sequence and conformation criteria of the multidimensional signature, but not yet recognized to have antimicrobial activity; 2) predicted failure of antimicrobial activity in peptides exhibiting primary sequence criteria, but lacking the 3-dimensional γ-core signature of the model; and 3) prediction of a γ-core motif in disulfide-containing peptides with known antimicrobial activity, and which fulfilled primary sequence criteria, but had unknown structure.

To test the hypothesis that the primary sequence patterns of the multidimensional signature are relevant to all classes of disulfide-containing antimicrobial peptides, Swiss-Prot forward and reverse databases (Gattiker et al., *Appl. Bioinformatics* 1:107 (2002)) were queried with the enantiomeric sequence formulae. Representatives of all major disulfide-containing antimicrobial peptide classes were retrieved (Table III). Searches also retrieved members of other peptide subclasses: i) neurotoxins, particularly charybdotoxin class of the family Buthidae (scorpion); ii) protease inhibitor or related peptides (eg., brazzein) from plants; iii) ferredoxins; and iv) metallothioneins. Prototypes with known 3-dimensional structures, but no known antimicrobial activity, were analyzed for the presence of the γ-core signature. Of these, the peptides brazzein and charybdotoxin were selected to test for antimicrobial activity based on two criteria: i) their quantitative RMSD values reflected greatest homology to the comparator γ-core motif; and ii) they represented diverse non-mammalian (plant or scorpion) host sources and distinct structure classes not previously known to have antimicrobial activity. Thus, brazzein and charybdotoxin exemplified peptides that fulfilled the enantiomeric sequence and γ-core criteria required for the multidimensional signature. These peptides were predicted to have direct antimicrobial activity. In contrast, prototype metallothioneins and ferredoxins did not contain γ-core motifs (FIG. 3; Table II). Thus, metallothionein II was selected as an example comparator predicted to lack antimicrobial activity.

These peptides were tested for antimicrobial activity against a panel of Gram-positive (*Staphylococcus aureus, Bacillus subtilis*) and Gram-negative (*Escherichia coli*) bacteria, and the fungus *Candida albicans*, using a well-established and sensitive in vitro assay [Antimicrobial activity was assessed using a well-established solid-phase diffusion method. Assays included well-characterized organisms: *Staphylococcus aureus* (ATCC 27217, Gram-positive); *Bacillus subtilis* (ATCC 6633, Gram-positive); *Escherichia coli* (strain ML-35, Gram-negative); and *Candida albicans* (ATCC 36082, fungus). In brief, organisms were cultured to logarithmic phase and inoculated at a density of $10^6$ colony forming units/ml in buffered molecular grade agarose at the indicated pH. Five μg of peptide resuspended in sterile deionized water were introduced into wells formed in the underlay, and incubated for 3 h at 37° C. Nutrient-containing overlay medium was then applied, and assays incubated at 37° C. or 30° C. for bacteria or fungi, respectively. Defensin HNP-1 was tested in parallel as a standard control. After 24 h, zones of complete or partial inhibition were measured. All assays were repeated independently a minimum of two times. Tang et al., *Infect. Immun.* 70:6524 (2002) for detailed methodology.].

Figure 7:
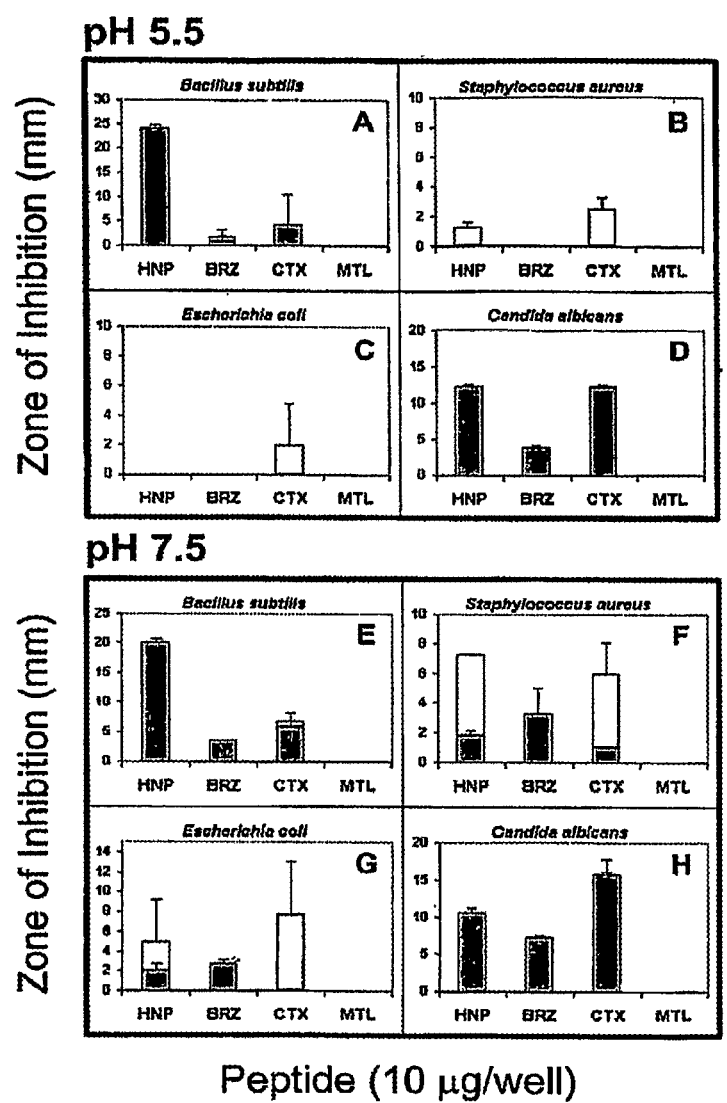
FIG. 7 shows experimental validation of the predictive accuracy of the multidimensional signature model. Standard radial diffusion assays were conducted using 10 µg of specified peptide: defensin HNP-1 (HNP); brazzein (BRZ); charybdotoxin (CTX); or metallothionein II (MTL). Recombinant brazzein reflecting the published 3-dimensional structure (1BRZ) as determined by nuclear magnetic resonance spectroscopy was kindly provided by Drs. J. L. Markley and F. M. Assadi-Porter, the University of Wisconsin 25. Charybdotoxin, metallothionein II, and defensin HNP-1 were obtained from commercial sources. Antimicrobial activity was assessed using a well-established solid-phase diffusion method as described by Tang et al., *Infect. Immun.* 70: 6524-6533 (2002). Assays included well characterized organisms: *Staphylococcus aureus* (ATCC 27217, Gram-positive coccus); *Bacillus subtilis* (ATCC 6633, Gram-positive *bacillus*); *Escherichia coli* (strain ML-35, Gram-negative *bacillus*); and *Candida albicans* (ATCC 36082, fungus). In brief, organisms were cultured to logarithmic phase and inoculated ($10^6$ colony forming units/ml) into buffered molecular-biology grade agarose at the indicated pH. Peptides resuspended in sterile deionized water were introduced into wells formed in the underlay, and incubated for 3 h at 37° C. Nutrient-containing overlay medium was then applied, and assays incubated at 37° C. or 30° C. for bacteria or fungi, respectively. After 24 h, zones of complete or partial inhibition were measured. All assays were repeated independently a minimum of two times at pH 5.5 (panels A-D) or pH 7.5 (panels E-H) to assess the influences of pH on peptide antimicrobial activities versus microorganisms. Histograms express mean (±standard deviation) zones of complete (blue) or incomplete (yellow) inhibition of growth. These data establish the direct antimicrobial activities of brazzein and charybdotoxin. Metallothionein II lacked antimicrobial activity under any condition assayed. Note differences in scale.

As predicted by the signature model, brazzein and charybdotoxin exerted direct antimicrobial activity against bacteria and *C. albicans* (FIG. 7). Notably, these peptides exhibited pH-specific antimicrobial activities, which in some conditions exceeded that of HNP-1. These results demonstrate for the first time to our knowledge the direct antimicrobial activities of brazzein and charybdotoxin. In contrast, metallothionein II failed to exert antimicrobial activity against any organism tested under any condition, as predicted by the model.

An alternative approach was also used to validate the multidimensional signature model. Tachyplesins are known cysteine-containing antimicrobial peptides from the horseshoe crab, *Tachypleus*. Two tachyplesins were retrieved from protein database searches employing the levomeric sequence formula (Table III). The model predicted that, because they have known antimicrobial activity, and fulfill the primary sequence criteria, tachyplesins would contain a γ-core motif. The 3-dimensional structure of tachyplesin I became available subsequent to development of the model (Laederach et al., *Biochem.* 41:12359 (2002)), and as predicted, exhibits a γ-core motif integral to the multidimensional signature of

TABLE III

Recognition of diverse classes of antimicrobial peptides by the enantiomeric sequence formulae. Forward or reverse Swiss-Prot Databases (release 42.4; Nov. 14, 2003; 138,347 entries) were probed with formulae containing the dextromeric or levomeric motifs of the antimicrobial peptide signature using PROSITE (Gattiker et al., *Appl. Bioinformatics* 1: 107 (2002)). Data indicate the proportionate distribution of a non-redundant cohort of retrieval sets; in some cases, peptides were retrieved by more than one formula isoform. Note that search results include members of the lantibiotic superfamily of antimicrobial peptides that lack conventional disulfide bridges, but have alternate thioether stabilization.

| Antimicrobial Peptide Class | Phylogeny | Sequence Isoform | | | Proportion | |
|---|---|---|---|---|---|---|
| | | Dextro | Levo - 1 | Levo - 2 | Total | % Total |
| α-defensin | Chordata | 24 | 42 | 6 | 72 | 15.3 |
| β-defensin | Chordata | 52 | 65 | 31 | 148 | 31.4 |
| θ-defensin | Chordata | 1 | 1 | 0 | 2 | 0.4 |
| Insect defensin/CS-αβ | Insectae | 21 | 23 | 12 | 56 | 11.9 |
| Plant defensin/CS-αβ | Plantae | 51 | 67 | 20 | 138 | 29.3 |
| Invertebrate defensin/CS-αβ | Mollusca | 3 | 4 | 4 | 11 | 2.3 |
| Protegrins/Gomesins | Chordata/Arthropoda | 0 | 0 | 6 | 6 | 1.3 |
| Tachyplesins/Polyphemusins | Arthropoda | 6 | 5 | 2 | 13 | 2.8 |
| Thanatin | Arthropoda | 0 | 1 | 0 | 1 | 0.2 |
| Mytilins/Big-Defensin | Mollusca | 3 | 3 | 2 | 8 | 1.7 |
| AFP-1 | Ascomycota | 1 | 0 | 0 | 1 | 0.2 |
| Lantibiotics/Microcins | Proteobacteria | 3 | 3 | 9 | 15 | 3.2 |
| | | 165 | 214 | 92 | 471 | | disulfide-containing antimicrobial peptides (FIG. 6). Confirmation of the 3-dimensional γ-core structure from antimicrobial activity and primary sequence pattern offers a robust and complementary validation of the multidimensional signature model.

Figure 8:
Figure 9:
FIG. 9 shows conservation of the multidimensional signature in disulfide-containing antimicrobial peptides. This triple alignment demonstrates the dramatic 3-dimensional conservation in antimicrobial peptides from phylogenetically diverse species spanning 2.6 billion years of evolution: fruit fly (*Drosophila*; /1MYN]), mussel (*Mytilus*; /1FJN]) and horsechestnut tree (*Aesculus*; /1BK8]). The striking degree of 3-dimensional preservation reflects a unifying structural code amongst these broad classes of disulfide containing host defense effector molecules. Alignment was carried out using the Vector Alignment Search Tool (VAST) available through the National Center for Biotechnology Information (NCBI). Secondary structure is indicated by the CN3D coloration schema: sheet, gold; helix, green; turn/extended, blue.
Figure 10A:
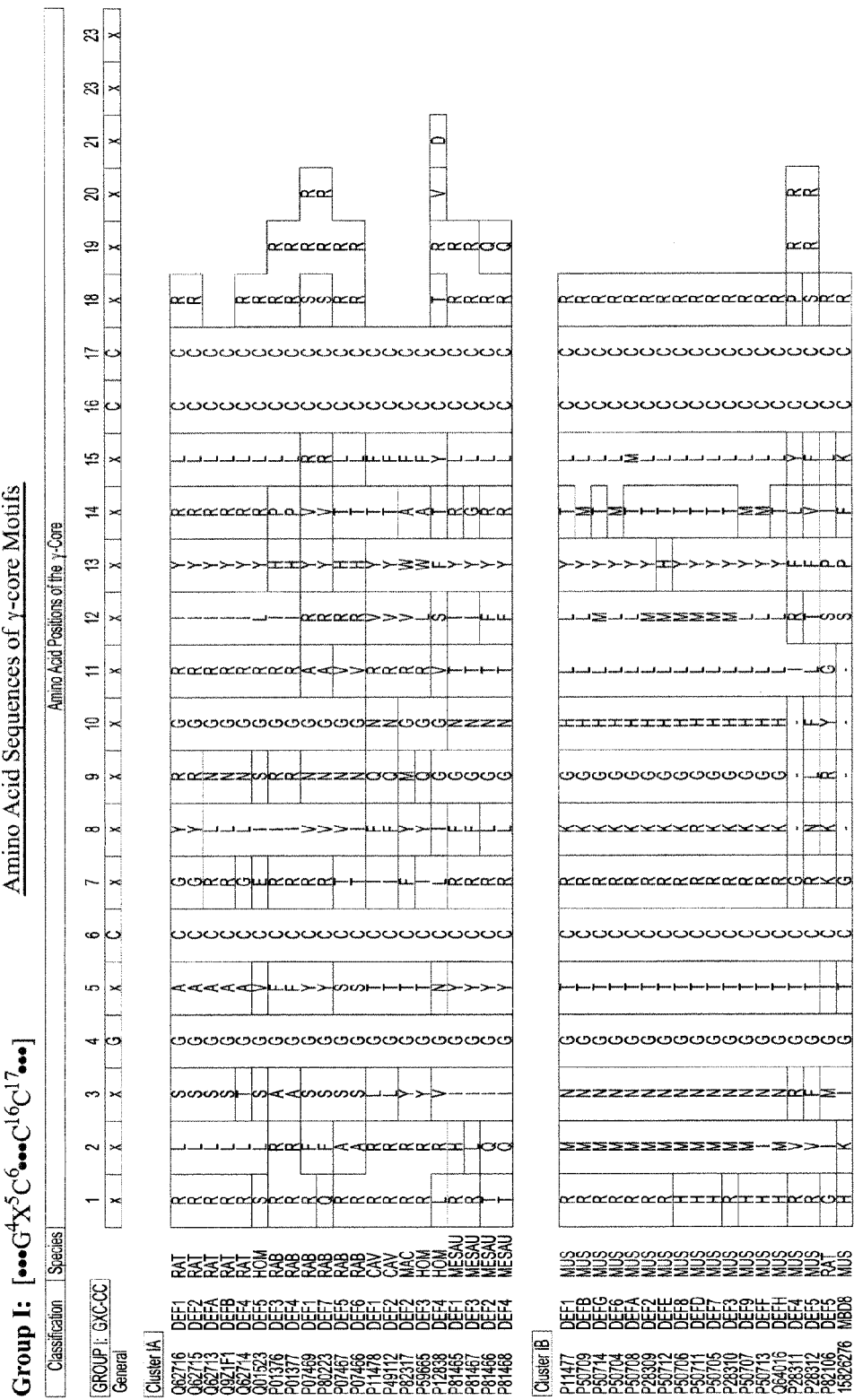
FIG. 10A depicts amino acid sequences of SEQ ID NOS: 93-132, in order from top to bottom.
Figure 10B:
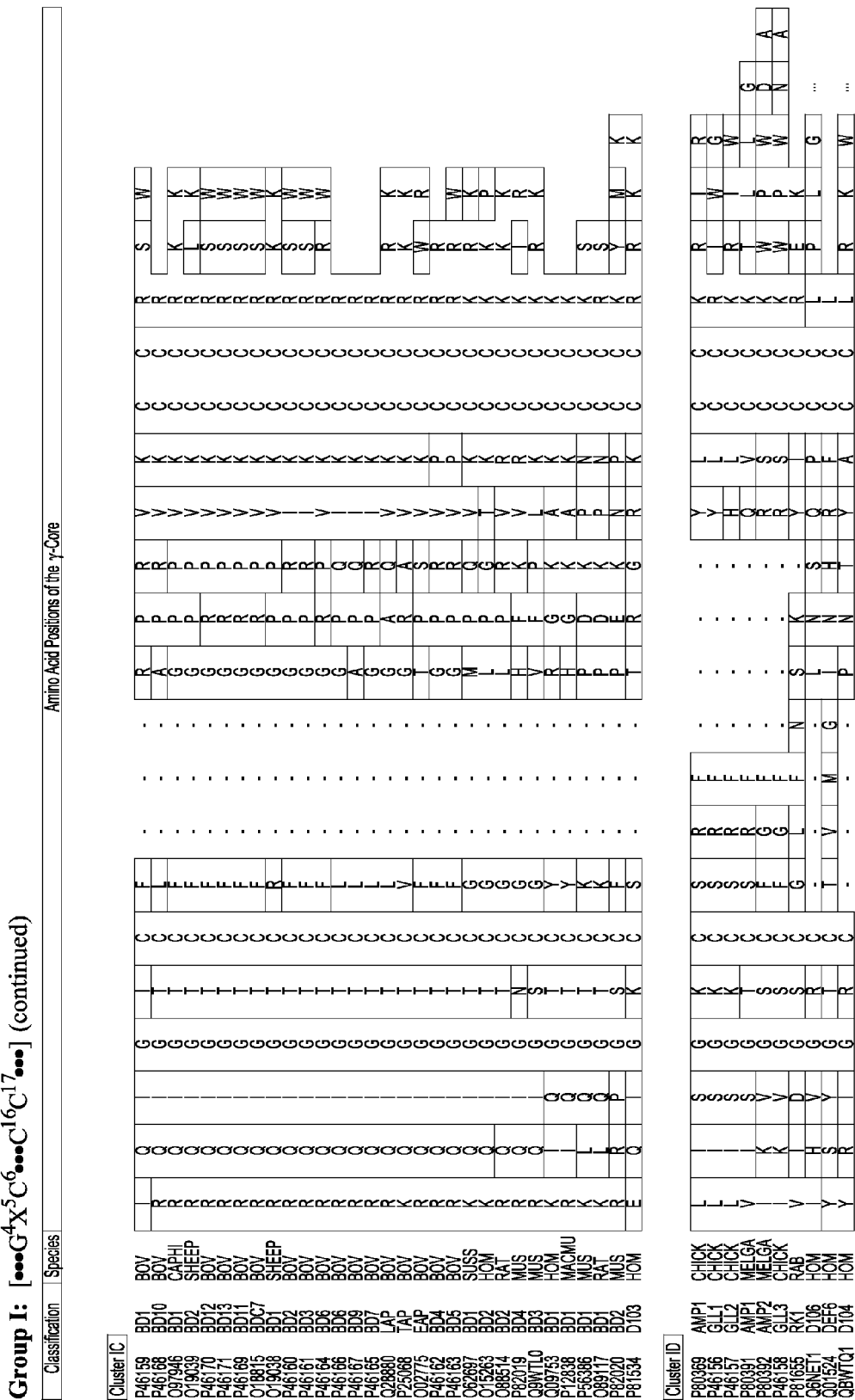
FIG. 10B depicts amino acid sequences of SEQ ID NOS: 133-173, in order from top to bottom.
Figure 10E:
FIG. 10E depicts amino acid sequences of SEQ ID NOS: 239-255, in order from top to bottom.
Figure 13:
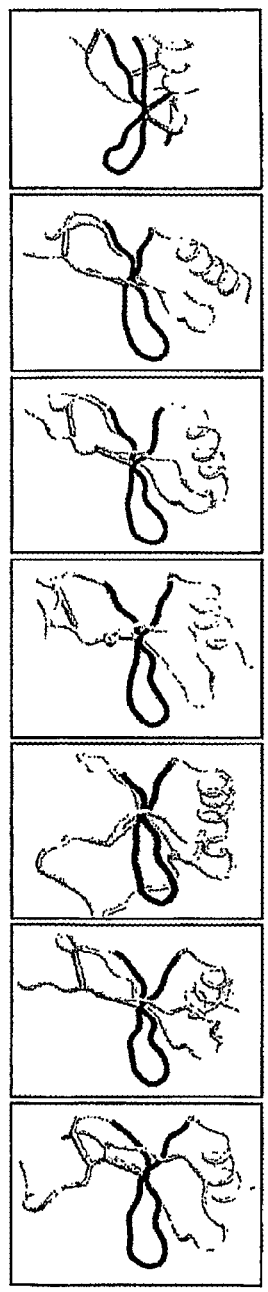
FIG. 13 demonstrates conservation of the γ-core domain within kinocidins ($\gamma_{KC}$ core). Recurring iterations of the $\gamma_{KC}$ core motif (red) are indicated with corresponding sequences ($GX_3C$) denoted in red or gold text. A comparator antimicrobial peptide (Ah-AMP-1) is also shown to illustrate structural similarities between the $\gamma_{KC}$ motif and that present in antimicrobial peptides ($\gamma_{AP}$). Proteins were visualized using protein explorer (Martz, E. (2002) Trends Biochem Sci 27, 107-9). Amino acid sequences of SEQ ID NOS: 352-358 are depicted.

The phylogenetic relationships among antimicrobial peptides containing the multidimensional signature were also examined. Study peptides sorted in a continuum of increasing structural complexity relative to the γ-core motif, rather than evolutionary relatedness of the source organisms (FIG. 8 A). This phylogenetic pattern is consistent with conservation of the γ-core motif amongst cysteine-containing antimicrobial peptides across biological kingdoms.

Example III

Validation of the Multidimensional Antimicrobial Peptide Signature Model

This example demonstrates the discovery of iterations of the γ-core motif in kinocidins and validation of the antimicrobial signature model in human IL-8.

A bioinformatics approach was used to specify and compare phylogeny and homology among kinocidin iterations of the γ-core motif previously identified in proteins with known or predicted antimicrobial function (Yount, N. Y. & Yeaman, M. R. (2004) *Proc Natl Acad Sci USA* 101, 7363-8). The kinocidin γ-core ($\gamma_{KC}$ core) signature is an iteration of the antimicrobial peptide γ-core ($\gamma_{AP}$), conforming to an antiparallel β-hairpin comprised of a 13-17 amino acid pattern with a central hydrophobic region typically flanked by basic residues. The $\gamma_{KC}$ core motif can be characterized by the following consensus sequence formula:

NH2 ... [X8-11]-[GX3C]-[X2]-[P] ... COOH    (SEQ ID NO: 364)

Figure 12:
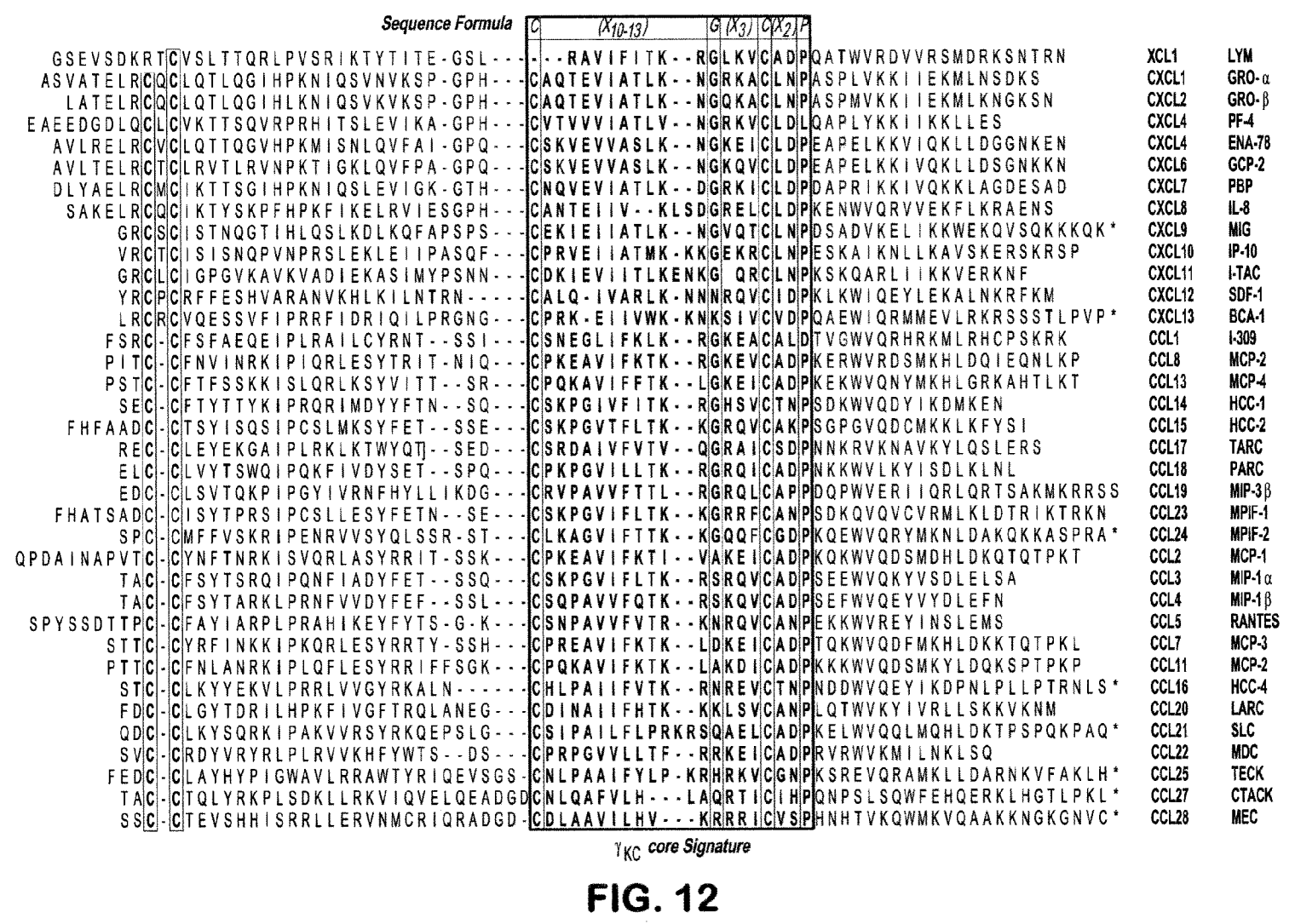

Sequence and 3-D analyses of more than 30 human CXC and CC kinocidins demonstrated that the $\gamma_{KC}$ core corresponds to the most highly conserved domain within the mature portion of these proteins (FIG. 12). Notably, the cysteine array and glycine residues hallmark of the $\gamma_{AP}$ core are also conserved in the $\gamma_{KC}$ motif. In kinocidins, the GXC consensus of the $\gamma_{AP}$ core is adapted such that a $GX_3C$ pattern is often observed. While the initial glycine of the GX3C pattern of kinocidins is conserved (>60%), the requirement for a glycine in this position is not absolute, with uncharged hydrophilic residues (A or N) as most common substitutions. A proline residue at its C-terminal aspect is another highly conserved feature (>95%) of the $\gamma_{KC}$ motif. This residue is located immediately prior to, and likely initiates the ensuing α-helical domain (FIG. 12).

Human IL-8 contains the sequence NH2 ... CANTEIIVKLSDGRELCLDP ... COOH (SEQ ID NO: 40), representing the $\gamma_{KC}$ core consensus formula, and shares specific physicochemical patterns of amphipathicity, charge distribution, and proline positioning with known kinocidins (FIG. 12). Based on the extensive structural homologies to kinocidins, IL-8 was predicted to have direct antimicrobial efficacy.

To confirm that IL-8 exerts direct antimicrobial efficacy, antimicrobial assays using a panel of prototypic pathogens were conducted as described in the following paragraphs.

Briefly, the antimicrobial assays were performed against a panel of prototype human pathogens as previously detailed (Yoshimura, T., Matsushima, K., Tanaka, S., Robinson, E. A., Appella, E., Oppenheim, J. J. & Leonard, E. J. (1987) *Proc Natl Acad Sci USA* 84, 9233-7): *Staphylococcus aureus* (ATCC 27217; Gram-positive bacterium); *Salmonella typhimurium* (5996s; Gram-negative bacterium); and the fungus *Candida albicans* (ATCC 36082). Defensin HNP-1 was included in each assay as an internal control, and all assays were conducted a minimum of two independent times. Results of independent assays were analyzed using Wilcoxon Rank Sum analysis with Bonferroni correction for multiple comparisons.

For the Solid-Phase Assay, mid-logarithmic phase organisms were prepared, introduced into buffered agarose (PIPES [10 mM, pH 7.5] or MES [2.0 mM, pH 5.5]) to achieve final inocula of $10^6$ CFU/ml, and poured into plates. Peptides (0.5 nmol/well [50 nmol/ml]) were added to wells in the seeded matrix, and incubated for 3 h at 37° C. Nutrient overlay medium was applied, and assays incubated at 37° C. or 30° C. for bacteria or fungi, respectively. After 24 h, zones of inhibition were measured, and results recorded as zones of complete or partial inhibition. This assay reflects microbiostatic (inhibition) and/or microbiocidal (killing) activities, but does not distinguish these effects.

Figure 14:
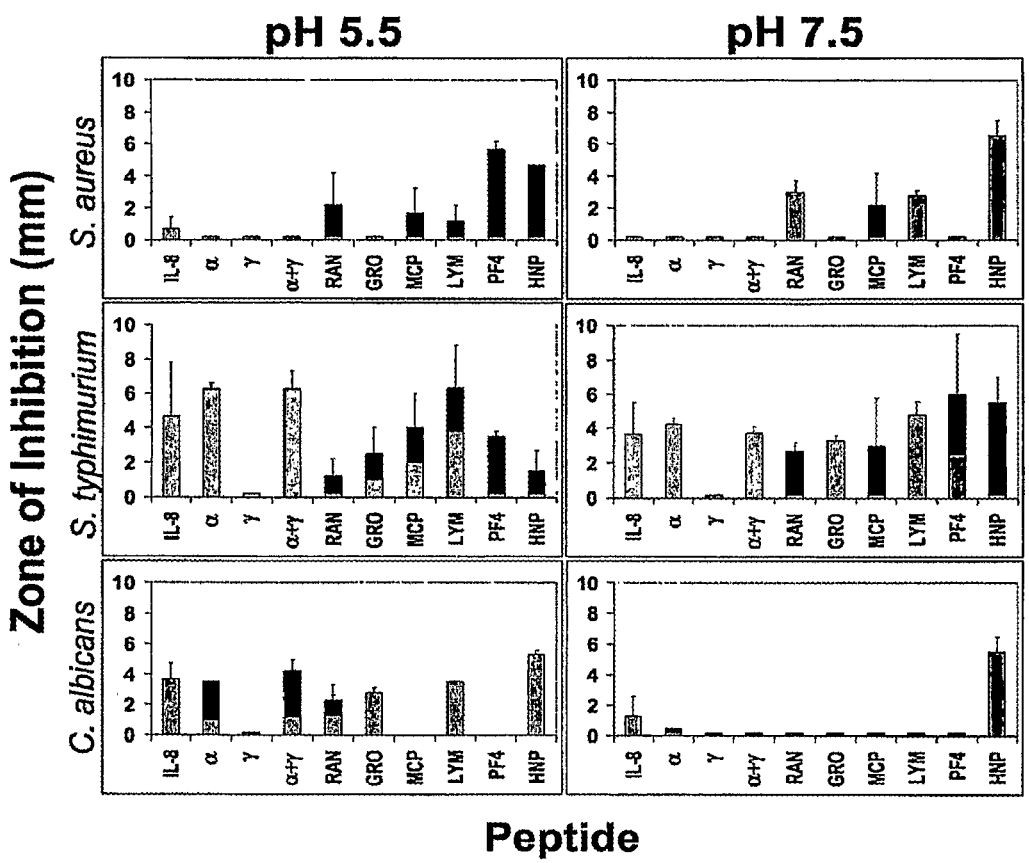
FIG. 14 shows solid-phase antimicrobial activity of human kinocidins and IL-8 subdomains IL-8α and IL-8γ. Peptides (0.5 nmol) were introduced into wells in agarose plates buffered with MES (2.0 mM, pH 5.5) or PIPES (10.0 mM, pH 7.5). Antimicrobial activity was assessed as the zone of complete (blue) or partial (red) inhibition around the well. Abbreviations are: Native IL-8 (IL-8); IL-8α, (α); IL-8γ, (γ); IL-8α+IL-8γ (α+γ); RANTES, (RAN); GRO-α, (GRO); MCP-1, (MCP); lymphotactin, (LYM); platelet factor-4, (PF-4); and HNP-1, (HNP). Histograms are means±SEM (minimum n=2).

As predicted by biophysical and structural congruence with other kinocidins, IL-8 exerted antimicrobial activity against bacteria and fungi in the solid-phase assay at pH 5.5 and 7.5. In many cases, antimicrobial spectra and efficacy of IL-8 were greater than other study kinocidins (FIG. 14). IL-8 was equivalent to lymphotactin, but more efficacious than any other test kinocidin against *S. typhimurium*. Against *S. aureus*, IL-8 (pH 5.5) had modest activity, with RANTES (pH 7.5), and lymphotactin (pH 7.5) being more efficacious. Significantly, IL-8 possessed striking antifungal activity versus *C. albicans*, greater than any other kinocidin at pH 5.5, and the only kinocidin with anti-candidal activity at pH 7.5. Excepting *S. aureus*, IL-8 displayed comparable antimicrobial efficacy to the classical antimicrobial peptide HNP-1 under the conditions tested. In addition to IL-8, the these results also demonstrate a direct antimicrobial efficacy for the kinocidin MCP-1. Interestingly, while MCP-1 exerted significant activity against Gram-positive and -negative bacteria, it had no measurable antifungal activity (FIG. 14).

Recombinant human chemokines [IL-8, RANTES, GRO-α, MCP-1, PF-4, and lymphotactin (Biosource International, Camarillo, Calif.)] and human neutrophil defensin-1 [HNP-1 (Peptides International, Louisville, Ky.)] were obtained commercially. Structural domains of IL-8 were generated by F-moc solid-phase synthesis: γ-core (ANTEIIVKLSDGRELCLDP; IL-8γ (SEQ ID NO: 42)), and α-helix (KENWVQRVVEKFLKRAENS; IL-8α (SEQ ID NO: 1)). Peptides were purified by RP-HPLC as previously described ((Tang, Y. Q., Yeaman, M. R. & Selsted, M. E. (2002) *Infect Immun* 70, 6524-33); >95% purity), and authenticated by amino acid analysis (Molecular Structure Facility, University of California, Davis) and MALDI-TOF spectrometry (UCLA Spectrometry Facility). Experimentally determined masses were within standard confidence intervals (<±0.1% of calculated molecular weight).

To characterize IL-8's antimicrobial activity in more detail, a quantitative solution-phase assay was carried out at pH 5.5 and 7.5. Organisms were prepared and adjusted to $10^6$ CFU/ml in PIPES or MES buffer as above but lacking agarose, and dispensed ($5 \times 10^4$ CFU per 50 µl aliquot). Peptide (concentration range, 20-0.00125 nmol/ml) was introduced into the assay medium, and incubated for 1 hour at 37° C.

Figure 15:
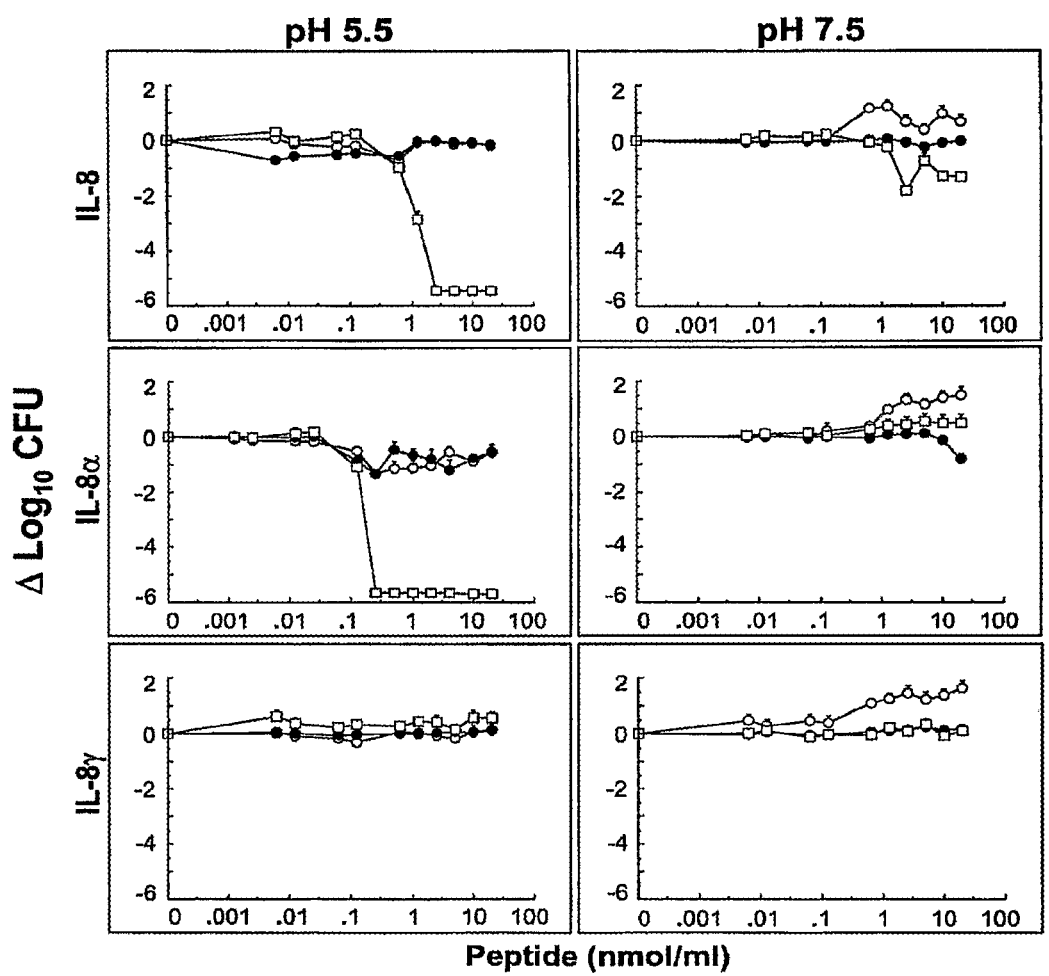
FIG. 15 shows solution-phase microbicidal activity of native IL-8 and subdomains IL-8α and IL-8-γ. One million CFU of the indicated microorganism per milliliter were incubated with peptide (0.00125-20.0 nmol/ml) in either MES (2.0 mM, pH 5.5) or PIPES (10.0 mM, pH 7.5) for one hour at 37° C. Surviving CFU were enumerated and are described as change in the initial log 10 CFU. ○, *S. aureus* ATCC 27217; ●, *S. typhimurium* strain 5990s; □, *C. albicans* ATCC 36082. Data are means±SD (minimum n=2).

After incubation, media were serially diluted and plated in triplicate for enumeration. IL-8 was highly fungicidal for *C. albicans*, achieving a five-log reduction in surviving CFU with 2.5 nmol/ml (20 µg/ml) peptide at pH 5.5 within 1 hour (FIG. 15). IL-8 was also fungicidal for *C. albicans* at pH 7.5, with a 2-log reduction in surviving CFU over 1 hour at a concentration of 2.5 nmol/ml. Interestingly, IL-8 did not exert microbicidal activity against *S. typhimurium* or *S. aureus* in this assay, indicating that its efficacies versus these organisms in solid-phase assay were due to bacteriostatic effects.

Synthetic IL-8γ and IL-8α peptides were used to probe for molecular determinants of IL-8 antimicrobial activity. IL-8α displayed a spectrum of efficacy virtually indistinguishable from that of the native molecule (FIG. 14). IL-8γ had no detectable antimicrobial efficacy at either pH 5.5 or 7.5. When assayed in combination, the pattern of antimicrobial activity was identical to that of IL-8α alone, indicating that IL-8γ did not impede the antimicrobial efficacy of IL-8α.

In the solution-phase assay, as little as 0.125 nmol/ml (1.0 µg/ml) of IL-8α achieved a five-log reduction in surviving *C. albicans* at pH 5.5 in 1 hour exposure (FIG. 15). By mass, the autonomous IL-8α domain conferred a 10-fold greater activity than native IL-8 against this organism. The pH specific efficacy patterns of IL-8α also mirrored those of full-length (FIG. 15). Consistent with results of the solid-phase assay, IL-8γ had no measurable activity in the solution-phase assay.

To assess the physiological relevance of the observed in vitro (solid and solution-phase) antimicrobial activity for IL-8 and IL-8α, we assessed the efficacy of IL-8α in the ex vivo biomatrix assay. This assay has been developed to assess antimicrobial polypeptide efficacy in complex human blood matrices. Antimicrobial activity of IL-8α in human whole blood and homologous plasma and serum fractions was assessed (Yeaman, M. R., Gank, K. D., Bayer, A. S., and Brass, E. P. (2002) *Antimicrob Agents Chemother* 46, 3883-3891). For biomatrix studies, the well-characterized *Escherichia coli* strain ML-35 was used as the target organism (Lehrer, R. I., Barton, A., Daher, K. A., Harwig, S. S., Ganz, T., and Selsted, M. E. (1989) *J Clin Invest* 84, 553-561). This strain is resistant to serum, ideal for use in assessing peptide antimicrobial activity in blood and blood-derived matrices (Yeaman, M. R., Gank, K. D., Bayer, A. S., and Brass, E. P. (2002) *Antimicrob Agents Chemother* 46, 3883-3891). Organisms were cultured to mid-logarithmic phase in brain-heart infusion broth (Difco Laboratories, Detroit, Mich.) at 37° C., washed, and resuspended in PBS (Irvine Scientific; pH 7.2). Inocula were quantified spectrophotometrically and validated by quantitative culture. Biomatrices were distributed in 85-µl aliquots into 96-well microtiter plates (Corning Glass Works, Corning, N.Y.) Peptide (5 µl; concentration range 1.0-50.0 µg/ml) was added either simultaneously with the microorganism (10 µl; $10^5$ CFU/ml), or after a 120 min pre-incubation period in the biomatrix. The mixtures were incubated with constant agitation for 2 h at 37° C. After incubation, aliquots were diluted and quantitatively cultured in triplicate onto blood agar. Surviving organisms were enumerated as CFU/ml. Experiments were performed a minimum of two independent times on different days and with different blood donor sources.

Importantly, IL-8α demonstrated significant efficacy against *E. coli*, causing decreases of up to log 5 CFU/ml at 10 µg/ml peptide. Greatest efficacy was seen in whole blood and serum in co-incubation studies, with less activity in plasma fractions or after 2 hour preincubation. To gain insights into these antimicrobial profiles, the structures of IL-8γ and IL-8α were investigated using biophysical and computational methods.

Secondary structures of IL-8 peptide domains were assessed by circular dichroism (CD) as previously noted (Sheppard et al. (2004) *J Biol Chem* 279, 30480-30489). Spectra were recorded with an AVIV 62DS spectropolarimeter (Aviv Biomedical Inc.). In brief, the purified peptides were solubilized (50 µg/ml in 50 mM NH4HC03; pH 5.5 or 7.5) and scanned using a 0.1-mm light path from 260 to 185 nm (rate, 10 nm/min; sample interval, 0.2 nm; 25° C.). A mean of 8 buffer-subtracted spectra were deconvoluted into helix, β-sheet, turn, and extended structures using Selcon (Sreerama et al. (1999) *Protein Sci* 8, 370-380) and Dichroweb (Lobley et al., (2002) *Bioinformatics* 18, 211-212); cryst.bbk.ac.uk/cdweb) as indicated (Sheppard et al. (2004) *J Biol Chem* 279, 30480-30489; Surewicz and Mantsch (1988) *Biochim Biophys Acta* 952, 115-130; Goormaghtigh et al. (1999) *Biochim Biophys Acta* 1422, 105-185).

Protein structure data were obtained from the National Center for Biotechnology Information (NCBI; PubMed Database), and visualized using Protein Explorer (Martz, E. (2002) *Trends Biochem Sci* 27, 107-109). Structural alignments were carried out using combinatorial extension, and significance of homology assessed by root mean square deviation analysis, as previously described (Yount and Yeaman (2004) *Proc Natl Acad Sci USA* 101, 7363-7368; Shindyalov and Bourne (1998) *Protein Eng* 11, 739-747).

3CD spectrometry indicated that IL-8γ and IL-8α recapitulated structures of corresponding regions in full-length IL-8 (FIG. 16). IL-8γ exhibited spectra consistent with a β-sheet structure, suggesting it spontaneously adopts a fold similar to that in native IL-8. Likewise, IL-8α displayed classic double dichroic minima at 208 and 218 nm, hallmark of α-helices, and concordant with the corresponding region in IL-8. These data suggest the forces responsible for secondary structures of these domains function independently from cysteine-stabilization or other constraints acting within the native molecule. Moreover, each structure was stable at pH 5.5 and pH 7.2 (FIG. 16).

To complement spectrometric studies, 3-D models of IL-8γ and IL-8α were created using homology and energy-based methods. Three-dimensional models of IL-8 domains were created using complementary methods (Yount et al. (2004) *Antimicrob Agents Chemother* 48, 4395-404). Homology [SWISSMODEL, BLAST2P; (Godzik et al. (1992) *J Mol Biol* 227, 227-38; Jaroszewski et al. (1998) *Protein Sci* 7, 1431-40], dynamic alignment (SIM) (Huang, X., and Miller, W. (1991) *Adv. Appl. Math.* 12, 337-367) and refined match (ProModII) algorithms were used to identify modeling templates. In a parallel strategy, IL-8 amino acid sequences were converted to putative solution conformations by threading methods (Matchmaker [Godzik et al. (1992) *J Mol Biol* 227, 227-238]; Gene-Fold [Jaroszewski et al. (1998) *Protein Sci* 7, 1431-1440]) implemented with SYBYL software (Tripos Associates, St. Louis, Mo.). Target conformers were refined using AMBER95 force field and molecular dynamics (Cornell et al. (1995) *J Am Chem Soc* 117, 5179-5197). In alternative approaches, molecular dynamics were executed without 0.4 kJ constraint penalties for canonical Ramachandran φ and Ψ angles.

The template utilized for target peptide modeling was human IL-8 (PDB code, 1IL8). As expected, each peptide retained secondary structure corresponding to homologous domains within the native molecule (FIG. 17). The IL-8γ core motif displayed an anti-parallel β-sheet motif, while the preferential conformation for IL-8α was a highly stable α-helical motif comprised of four turns. These structure assignments are strongly supported by favorable empirical energy functions, equivalent to those of the IL-8 template.

TABLE III

Comparative physicochemical properties of human kinocidins and α-helical domains thereof.

| Classification Schema | | | Native Molecule | | | | α-Helical Domain | | | | |
|---|---|---|---|---|---|---|---|---|---|---|---|
| Class | Ligand ID | Name | AA | M | Q | pI | $AA_\alpha$ | $Q_\alpha$ | $M_\alpha$ | $pI_\alpha$ | $H_\alpha$ |
| CXC | CXCL8 | IL-8 | 71 | 8299 | +4 | 9.0 | 17 | +2 | 2103 | 10.0 | 6.70 |
| CXC | CXCL4 | PF-4 | 70 | 7769 | +3 | 8.8 | 13 | +3 | 1573 | 9.8 | 6.12 |
| CXC | CXCL1 | GRO-α | 72 | 7751 | +6 | 9.5 | 16 | +2 | 1843 | 9.6 | 4.71 |
| CC | CCL2 | MCP-1 | 76 | 8685 | +6 | 9.4 | 19 | 0 | 2287 | 6.8 | 5.35 |
| CC | CCL5 | RANTES | 68 | 7851 | +5 | 9.2 | 13 | 0 | 1655 | 6.1 | 6.71 |
| C | CL1 | Lymphotactin | 92 | 10173 | +9 | 10.6 | 14 | +2 | 1735 | 10.7 | 3.73 |

Physicochemical parameters are abbreviated for the native or α-helical domain (α),: AA—amino acids; M—average mass (Da); Q—calculated charge at pH 7.0; pI—estimated isoelectric point (Bjellqvist et al., (1994) *Electrophoresis* 15, 529-39); H—hydrophobic moment (Zidovetzki et al. (2003) *Biophys Chem* 100, 555-75).

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. An antimicrobial peptide consisting of the amino acid sequence KENWVQRVVEKFLKRAENS (SEQ ID NO: 1).

2. A method for treating an infectious disease or condition in a subject in need of such treatment comprising administering to the subject an effective amount of the antimicrobial peptide of claim 1.

3. The method of claim 2, wherein said method further comprises administering a second antimicrobial agent.

4. The method of claim 3, wherein said second antimicrobial agent is an antifungal agent.

5. The method of claim 4, wherein said antifungal agent is a polyene derivative, an azole derivative, an allylaminesthiocarbamate, an echinocandin, a nikkomycin, or a sordarin.

6. The method of claim 4, wherein said antifungal agent is selected from the group consisting of amphotericin B, nystatin, pimaricin, flucytosine, ketoconazole, clotrimazole, miconazole, econazole, butoconazole, oxiconazole, sulconazole, tioconazole, terconazole, fluconazole, itraconazole, voriconazole, posaconazole, ravuconazole tolnaftate, naftifine, terbinafine, griseofulvin, ciclopirox, haloprogin, caspofungin, FK463, cilofungin, and VER-002.

7. The method of claim 3, wherein said second antimicrobial agent is an antibiotic.

8. The method of claim 7, wherein said antibiotic is a β-lactam, a penicillin, a cephalosporin, a monobactam, a β-lactam with a β-lactamase inhibitor, an aminoglycoside, an tetracycline, a quinolone, a fluoroquinolone, a macrolide, a polymyxin, a lincosamide, or an oxazolidinone.

9. The method of claim 7, wherein said antibiotic is selected from the group consisting of gentamicin, tobramycin, netilmycin, amikacin, ciprofloxacin, norfloxacin, ofloxacin, moxifloxacin, trovafloxacin, grepafloxacin, levofloxacin, gatifloxacin, vancomycin, erythromycin, azithromycin, clarithromycin, chloramphenicol, and rifampin.

10. The method of claim 2, wherein said infectious disease or condition is caused by a fungal species, a gram-negative bacterial species, a gram-positive bacterial species, a protozoa, or a parasite.

11. The method of claim 10, wherein said fungal species is a *Candida* species, an *Aspergillus* species, a *Cryptococcus* species, a *Histoplasma* species, a *Coccidioides* species, a *Paracoccidioides* species, a *Blastomyces* species, a *Basidiobolus* species, a *Conidiobolus* species, a *Rhizopus* species, a *Rhizomucor* species, a *Mucor* species, an *Absidia* species, a *Mortierella* species, a *Cunninghamella* species, a *Saksenaea* species, a *Pseudallescheria* species, a *Paecilomyces* species, a *Fusarium* species, a *Trichophyton* species, a *Trichosporon* species, a *Microsporum* species, an *Epidermophyton* species, a *Scytalidium* species, a *Malassezia* species, an *Actinomycetes* species, a *Sporothrix* species, a *Penicillium* species, a *Saccharomyces* species, or a *Pneumocystis* species.

12. The method of claim 11, wherein said *Candida* species is selected from the group consisting of *C. albicans, C. tropicalis, C. parapsilosis, C. stellatoidea, C. krusei, C. parakrusei, C. lusitanae, C. pseudotropicalis, C. guilliermondi, C. dubliniensis, C. famata,* and *C. glabrata.*

13. The method of claim 11, wherein said *Aspergillus* species is selected from the group consisting of *A. fumigatus, A. flavus, A. niger, A. nidulans, A. terreus, A. sydowi, A. flavatus,* and *A. glaucus.*

14. The method of claim 10, wherein said gram-negative bacterial species is an *Acidaminococcus* species, an *Acinetobacter* species, an *Aeromonas* species, an *Alcaligenes* species, a *Bacteroides* species, a *Bordetella* species, a *Branhamella* species, a *Brucella* species, a *Burkholderia* species, a *Calymmatobacterium* species, a *Campylobacter* species, a *Cardiobacterium* species, a *Chromobacterium* species, a *Citrobacter* species, an *Edwardsiella* species, an *Enterobacter* species, an *Escherichia* species, a *Flavobacterium* species, a *Francisella* species, a *Fusobacterium* species, a *Haemophilus* species, a *Klebsiella* species, a *Legionella* species, a *Moraxella* species, a *Morganella* species, a *Neisseria* species, a *Pasturella* species, a *Plesiomonas* species, a *Porphyromonas* species, a *Prevotella* species, a *Proteus* species, a *Providencia* species, a *Pseudomonas* species, a *Salmonella* species, a *Serratia* species, a *Shigella* species, a *Stentrophomonas* species, a *Streptobacillus* species, a *Treponema* species, a *Veillonella* species, a *Vibrio* species, an *Yersinia* species, or a *Chlamydia* species.

15. The method of claim 10, wherein said gram-positive bacterial species is a *Staphylococcus* species, a *Streptococcus* species, a *Micrococcus* species, a *Peptococcus* species, a *Peptostreptococcus* species, an *Enterococcus* species, a *Bacillus* species, a *Clostridium* species, a *Lactobacillus* species, a *Listeria* species, an *Erysipelothrix* species, a *Propionibacterium* species, an *Eubacterium* species, a *Nocardia* species, an *Actinomyces* species, a *Corynebacterium* species, a *Mycoplasma* species, an *Ureaplasma* species, or a *Mycobacteria* species.

16. The method of claim 10, wherein said protozoa is a *Plasmodia* species, a *Toxoplasma* species, a *Leishmania* species, a *Trypanosoma* species, a *Giardia* species, a *Entamoeba* species, a *Acanthamoeba* species, a *Nagleria* species, a *Hartmanella* species, a *Balantidium* species, a *Babesia* species, a *Cryptosporidium* species, a *Isospora* species, a *Microsporidium* species, a *Trichomonas* species, or a *Pneumocystis* species.

17. The method of claim 10, wherein said parasite is a helminth parasite.

18. The method of claim 2, wherein said subject is a mammal.

19. The method of claim 18, wherein said mammal is a human.

20. The method of claim 2, wherein said subject is immunocompromised or immunosuppressed.

* * * * *

```
                        SEQUENCE LISTING

<160> NUMBER OF SEQ ID NOS: 364

<210> SEQ ID NO 1
<211> LENGTH: 19
<212> TYPE: PRT
<213> ORGANISM: Artificial Sequence
<220> FEATURE:
<223> OTHER INFORMATION: Synthetic peptide

<400> SEQUENCE: 1

Lys Glu Asn Trp Val Gln Arg Val Val Glu Lys Phe Leu Lys Arg Ala
1               5                   10                  15

Glu Asn Ser

<210> SEQ ID NO 2
<211> LENGTH: 15
<212> TYPE: PRT
<213> ORGANISM: Artificial Sequence
<220> FEATURE:
<223> OTHER INFORMATION: Synthetic peptide

<400> SEQUENCE: 2

Gln Ala Pro Leu Tyr Lys Lys Ile Ile Lys Lys Leu Leu Glu Ser
1               5                   10                  15

<210> SEQ ID NO 3
<211> LENGTH: 19
<212> TYPE: PRT
<213> ORGANISM: Artificial Sequence
<220> FEATURE:
<223> OTHER INFORMATION: Synthetic peptide

<400> SEQUENCE: 3

Ala Ser Pro Ile Val Lys Lys Ile Ile Glu Lys Met Leu Asn Ser Asp
1               5                   10                  15
```

Lys Ser Asn

<210> SEQ ID NO 4
<211> LENGTH: 18
<212> TYPE: PRT
<213> ORGANISM: Artificial Sequence
<220> FEATURE:
<223> OTHER INFORMATION: Synthetic peptide

<400> SEQUENCE: 4

Asp Ala Pro Arg Ile Lys Lys Ile Val Gln Lys Lys Leu Ala Gly Asp
1               5                   10                  15

Glu Ser

<210> SEQ ID NO 5
<211> LENGTH: 19
<212> TYPE: PRT
<213> ORGANISM: Artificial Sequence
<220> FEATURE:
<223> OTHER INFORMATION: Synthetic peptide

<400> SEQUENCE: 5

Ala Ser Pro Met Val Lys Lys Ile Ile Glu Lys Met Leu Lys Asn Gly
1               5                   10                  15

Lys Ser Asn

<210> SEQ ID NO 6
<211> LENGTH: 19
<212> TYPE: PRT
<213> ORGANISM: Artificial Sequence
<220> FEATURE:
<223> OTHER INFORMATION: Synthetic peptide

<400> SEQUENCE: 6

Ala Ser Pro Met Val Gln Lys Ile Ile Glu Lys Ile Leu Asn Lys Gly
1               5                   10                  15

Ser Thr Asn

<210> SEQ ID NO 7
<211> LENGTH: 20
<212> TYPE: PRT
<213> ORGANISM: Artificial Sequence
<220> FEATURE:
<223> OTHER INFORMATION: Synthetic peptide

<400> SEQUENCE: 7

Glu Ala Pro Phe Leu Lys Lys Val Ile Gln Lys Ile Leu Asp Gly Gly
1               5                   10                  15

Asn Lys Glu Asn
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic peptide

<400> SEQUENCE: 8

Glu Ala Pro Phe Leu Lys Lys Val Ile Gln Lys Ile Leu Asp Ser Gly
1               5                   10                  15

Asn Lys Lys Asn
            20

<210> SEQ ID NO 9
<211> LENGTH: 20
<212> TYPE: PRT
<213> ORGANISM: Artificial Sequence
<220> FEATURE:
<223> OTHER INFORMATION: Synthetic peptide

<400> SEQUENCE: 9

Asp Ala Pro Arg Ile Lys Lys Ile Val Gln Lys Lys Leu Ala Gly Asp
1               5                   10                  15

Glu Ser Ala Asp
            20

<210> SEQ ID NO 10
<211> LENGTH: 21
<212> TYPE: PRT
<213> ORGANISM: Artificial Sequence
<220> FEATURE:
<223> OTHER INFORMATION: Synthetic peptide

<400> SEQUENCE: 10

Glu Ser Lys Ala Ile Lys Asn Leu Leu Lys Ala Val Ser Lys Glu Arg
1               5                   10                  15

Ser Lys Arg Ser Pro
            20

<210> SEQ ID NO 11
<211> LENGTH: 17
<212> TYPE: PRT
<213> ORGANISM: Artificial Sequence
<220> FEATURE:
<223> OTHER INFORMATION: Synthetic peptide

<400> SEQUENCE: 11

Lys Ser Lys Gln Ala Arg Leu Ile Ile Lys Lys Val Glu Arg Lys Asn
1               5                   10                  15

Phe

<210> SEQ ID NO 12
<211> LENGTH: 19
<212> TYPE: PRT
<213> ORGANISM: Artificial Sequence
<220> FEATURE:
<223> OTHER INFORMATION: Synthetic peptide

<400> SEQUENCE: 12

Lys Leu Lys Trp Ile Gln Glu Tyr Leu Glu Lys Ala Leu Asn Lys Arg
1               5                   10                  15

Phe Lys Met

<210> SEQ ID NO 13
<211> LENGTH: 30
<212> TYPE: PRT
<213> ORGANISM: Artificial Sequence
<220> FEATURE:
<223> OTHER INFORMATION: Synthetic peptide

<400> SEQUENCE: 13

Gln Ala Glu Trp Ile Gln Arg Met Met Glu Val Leu Arg Lys Arg Ser
1               5                   10                  15

Ser Ser Thr Leu Pro Val Pro Val Phe Lys Arg Lys Ile Pro
            20                  25                  30

<210> SEQ ID NO 14

```
<211> LENGTH: 24
<212> TYPE: PRT
<213> ORGANISM: Artificial Sequence
<220> FEATURE:
<223> OTHER INFORMATION: Synthetic peptide

<400> SEQUENCE: 14

Lys Leu Gln Ser Thr Lys Arg Phe Ile Lys Trp Tyr Asn Ala Trp Asn
1               5                   10                  15

Glu Lys Arg Arg Val Tyr Glu Glu
            20

<210> SEQ ID NO 15
<211> LENGTH: 20
<212> TYPE: PRT
<213> ORGANISM: Artificial Sequence
<220> FEATURE:
<223> OTHER INFORMATION: Synthetic peptide

<400> SEQUENCE: 15

Thr Val Gly Trp Val Gln Arg His Arg Lys Met Leu Arg His Cys Pro
1               5                   10                  15

Ser Lys Arg Lys
            20

<210> SEQ ID NO 16
<211> LENGTH: 21
<212> TYPE: PRT
<213> ORGANISM: Artificial Sequence
<220> FEATURE:
<223> OTHER INFORMATION: Synthetic peptide

<400> SEQUENCE: 16

Lys Gln Lys Trp Val Gln Asp Ser Met Asp His Leu Asp Lys Gln Thr
1               5                   10                  15

Gln Thr Pro Lys Thr
            20

<210> SEQ ID NO 17
<211> LENGTH: 16
<212> TYPE: PRT
<213> ORGANISM: Artificial Sequence
<220> FEATURE:
<223> OTHER INFORMATION: Synthetic peptide

<400> SEQUENCE: 17

Ser Glu Glu Trp Val Gln Lys Tyr Val Ser Asp Leu Glu Leu Ser Ala
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic peptide

<400> SEQUENCE: 18

Ser Glu Ser Trp Val Gln Glu Tyr Val Tyr Asp Leu Glu Leu Asn
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide
```

```
<400> SEQUENCE: 19

Glu Lys Lys Trp Val Arg Glu Tyr Ile Asn Ser Leu Glu Met Ser
1               5                   10                  15

<210> SEQ ID NO 20
<211> LENGTH: 21
<212> TYPE: PRT
<213> ORGANISM: Artificial Sequence
<220> FEATURE:
<223> OTHER INFORMATION: Synthetic peptide

<400> SEQUENCE: 20

Thr Gln Lys Trp Val Gln Asp Phe Met Lys His Leu Asp Lys Lys Thr
1               5                   10                  15

Gln Thr Pro Lys Leu
            20

<210> SEQ ID NO 21
<211> LENGTH: 21
<212> TYPE: PRT
<213> ORGANISM: Artificial Sequence
<220> FEATURE:
<223> OTHER INFORMATION: Synthetic peptide

<400> SEQUENCE: 21

Lys Glu Arg Trp Val Arg Asp Ser Met Lys His Leu Asp Gln Ile Phe
1               5                   10                  15

Gln Asn Leu Lys Pro
            20

<210> SEQ ID NO 22
<211> LENGTH: 21
<212> TYPE: PRT
<213> ORGANISM: Artificial Sequence
<220> FEATURE:
<223> OTHER INFORMATION: Synthetic peptide

<400> SEQUENCE: 22

Lys Lys Lys Trp Val Gln Asp Ser Met Lys Tyr Leu Asp Gln Lys Ser
1               5                   10                  15

Pro Thr Pro Lys Pro
            20

<210> SEQ ID NO 23
<211> LENGTH: 21
<212> TYPE: PRT
<213> ORGANISM: Artificial Sequence
<220> FEATURE:
<223> OTHER INFORMATION: Synthetic peptide

<400> SEQUENCE: 23

Lys Glu Lys Trp Val Gln Asn Tyr Met Lys His Leu Gly Arg Lys Ala
1               5                   10                  15

His Thr Leu Lys Thr
            20

<210> SEQ ID NO 24
<211> LENGTH: 15
<212> TYPE: PRT
<213> ORGANISM: Artificial Sequence
<220> FEATURE:
<223> OTHER INFORMATION: Synthetic peptide

<400> SEQUENCE: 24

Ser Asp Lys Trp Val Gln Asp Tyr Ile Lys Asp Met Lys Glu Asn
```

<210> SEQ ID NO 25
<211> LENGTH: 17
<212> TYPE: PRT
<213> ORGANISM: Artificial Sequence
<220> FEATURE:
<223> OTHER INFORMATION: Synthetic peptide

<400> SEQUENCE: 25

Ser Gly Pro Gly Val Gln Asp Cys Met Lys Lys Leu Lys Pro Tyr Ser
1               5                   10                  15

Ile

<210> SEQ ID NO 26
<211> LENGTH: 28
<212> TYPE: PRT
<213> ORGANISM: Artificial Sequence
<220> FEATURE:
<223> OTHER INFORMATION: Synthetic peptide

<400> SEQUENCE: 26

Asn Asp Asp Trp Val Gln Glu Tyr Ile Lys Asp Pro Asn Leu Pro Leu
1               5                   10                  15

Leu Pro Thr Arg Asn Leu Ser Thr Val Lys Ile Ile
            20                  25

<210> SEQ ID NO 27
<211> LENGTH: 18
<212> TYPE: PRT
<213> ORGANISM: Artificial Sequence
<220> FEATURE:
<223> OTHER INFORMATION: Synthetic peptide

<400> SEQUENCE: 27

Asn Asn Lys Arg Val Lys Asn Ala Val Lys Tyr Leu Gln Ser Leu Glu
1               5                   10                  15

Arg Ser

<210> SEQ ID NO 28
<211> LENGTH: 16
<212> TYPE: PRT
<213> ORGANISM: Artificial Sequence
<220> FEATURE:
<223> OTHER INFORMATION: Synthetic peptide

<400> SEQUENCE: 28

Asn Lys Lys Trp Val Gln Lys Tyr Ile Ser Asp Leu Lys Leu Asn Ala
1               5                   10                  15

<210> SEQ ID NO 29
<211> LENGTH: 24
<212> TYPE: PRT
<213> ORGANISM: Artificial Sequence
<220> FEATURE:
<223> OTHER INFORMATION: Synthetic peptide

<400> SEQUENCE: 29

Asp Gln Pro Trp Val Glu Arg Ile Ile Gln Arg Leu Gln Arg Thr Ser
1               5                   10                  15

Ala Lys Met Lys Arg Arg Ser Ser
            20

<210> SEQ ID NO 30
<211> LENGTH: 19

```
<212> TYPE: PRT
<213> ORGANISM: Artificial Sequence
<220> FEATURE:
<223> OTHER INFORMATION: Synthetic peptide

<400> SEQUENCE: 30

Lys Gln Thr Trp Val Lys Tyr Ile Val Arg Leu Leu Ser Lys Val
1               5                   10                  15

Lys Asn Met

<210> SEQ ID NO 31
<211> LENGTH: 24
<212> TYPE: PRT
<213> ORGANISM: Artificial Sequence
<220> FEATURE:
<223> OTHER INFORMATION: Synthetic peptide

<400> SEQUENCE: 31

Lys Glu Leu Trp Val Gln Gln Leu Met Gln His Leu Asp Lys Thr Pro
1               5                   10                  15

Ser Pro Gln Lys Pro Ala Gln Gly
            20

<210> SEQ ID NO 32
<211> LENGTH: 14
<212> TYPE: PRT
<213> ORGANISM: Artificial Sequence
<220> FEATURE:
<223> OTHER INFORMATION: Synthetic peptide

<400> SEQUENCE: 32

Arg Val Pro Trp Val Lys Met Ile Leu Asn Lys Leu Ser Gln
1               5                   10

<210> SEQ ID NO 33
<211> LENGTH: 23
<212> TYPE: PRT
<213> ORGANISM: Artificial Sequence
<220> FEATURE:
<223> OTHER INFORMATION: Synthetic peptide

<400> SEQUENCE: 33

Ser Asp Lys Gln Val Gln Val Cys Val Arg Met Leu Lys Leu Asp Thr
1               5                   10                  15

Arg Ile Lys Thr Arg Lys Asn
            20

<210> SEQ ID NO 34
<211> LENGTH: 24
<212> TYPE: PRT
<213> ORGANISM: Artificial Sequence
<220> FEATURE:
<223> OTHER INFORMATION: Synthetic peptide

<400> SEQUENCE: 34

Lys Gln Glu Trp Val Gln Arg Tyr Met Lys Asn Leu Asp Ala Lys Gln
1               5                   10                  15

Lys Lys Ala Ser Pro Arg Ala Arg
            20

<210> SEQ ID NO 35
<211> LENGTH: 17
<212> TYPE: PRT
<213> ORGANISM: Artificial Sequence
<220> FEATURE:
<223> OTHER INFORMATION: Synthetic peptide
```

```
<400> SEQUENCE: 35

Lys Ser Arg Glu Val Gln Arg Ala Met Lys Leu Leu Asp Ala Arg Asn
1               5                   10                  15

Lys

<210> SEQ ID NO 36
<211> LENGTH: 32
<212> TYPE: PRT
<213> ORGANISM: Artificial Sequence
<220> FEATURE:
<223> OTHER INFORMATION: Synthetic peptide

<400> SEQUENCE: 36

Gln Asn Pro Ser Leu Ser Gln Trp Phe Glu His Gln Glu Arg Lys Leu
1               5                   10                  15

His Gly Thr Leu Pro Lys Leu Asn Phe Gly Met Leu Arg Lys Met Gly
            20                  25                  30

<210> SEQ ID NO 37
<211> LENGTH: 21
<212> TYPE: PRT
<213> ORGANISM: Artificial Sequence
<220> FEATURE:
<223> OTHER INFORMATION: Synthetic peptide

<400> SEQUENCE: 37

His Asn His Thr Val Lys Gln Trp Met Lys Val Gln Ala Ala Lys Lys
1               5                   10                  15

Asn Gly Lys Gly Asn
            20

<210> SEQ ID NO 38
<211> LENGTH: 21
<212> TYPE: PRT
<213> ORGANISM: Artificial Sequence
<220> FEATURE:
<223> OTHER INFORMATION: Synthetic peptide

<400> SEQUENCE: 38

Gln Ala Thr Trp Val Arg Asp Val Val Arg Ser Met Asp Arg Lys Ser
1               5                   10                  15

Asn Thr Arg Asn Asn
            20

<210> SEQ ID NO 39
<211> LENGTH: 22
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(14)
<223> OTHER INFORMATION: region may encompass between 10 and 13 variable
      amino acids
<220> FEATURE:
<221> NAME/KEY: MOD_RES
<222> LOCATION: (16)..(18)
<223> OTHER INFORMATION: region may encompass between 2 and 3 variable
      amino acids
<220> FEATURE:
<221> NAME/KEY: MOD_RES
<222> LOCATION: (20)..(21)
<223> OTHER INFORMATION: variable amino acid

<400> SEQUENCE: 39
```

```
Cys Xaa Xaa Xaa Xaa Xaa Xaa Xaa Xaa Xaa Xaa Xaa Xaa Gly Xaa
1               5                   10                  15

Xaa Xaa Cys Xaa Xaa Pro
            20

<210> SEQ ID NO 40
<211> LENGTH: 20
<212> TYPE: PRT
<213> ORGANISM: Artificial Sequence
<220> FEATURE:
<223> OTHER INFORMATION: Synthetic peptide

<400> SEQUENCE: 40

Cys Ala Asn Thr Glu Ile Ile Val Lys Leu Ser Asp Gly Arg Glu Leu
1               5                   10                  15

Cys Leu Asp Pro
            20

<210> SEQ ID NO 41
<211> LENGTH: 22
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(5)
<223> OTHER INFORMATION: variable amino acid
<220> FEATURE:
<221> NAME/KEY: MOD_RES
<222> LOCATION: (6)..(8)
<223> OTHER INFORMATION: variable hydrophobic amino acid residue
<220> FEATURE:
<221> NAME/KEY: MOD_RES
<222> LOCATION: (9)..(10)
<223> OTHER INFORMATION: region may encompass between 0 and 2 variable
      amino acids
<220> FEATURE:
<221> NAME/KEY: MOD_RES
<222> LOCATION: (12)..(14)
<223> OTHER INFORMATION: region may encompass between 1 and 3 variable
      amino acids
<220> FEATURE:
<221> NAME/KEY: MOD_RES
<222> LOCATION: (16)..(16)
<223> OTHER INFORMATION: Lys or Arg
<220> FEATURE:
<221> NAME/KEY: MOD_RES
<222> LOCATION: (17)..(17)
<223> OTHER INFORMATION: variable charged or polar amino acid residue
<220> FEATURE:
<221> NAME/KEY: MOD_RES
<222> LOCATION: (18)..(18)
<223> OTHER INFORMATION: variable hydrophobic amino acid residue
<220> FEATURE:
<221> NAME/KEY: MOD_RES
<222> LOCATION: (20)..(20)
<223> OTHER INFORMATION: variable hydrophobic amino acid residue
<220> FEATURE:
<221> NAME/KEY: MOD_RES
<222> LOCATION: (21)..(21)
<223> OTHER INFORMATION: Asp or Asn

<400> SEQUENCE: 41

Cys Xaa Xaa Xaa Xaa Xaa Xaa Xaa Xaa Xaa Lys Xaa Xaa Xaa Gly Xaa
1               5                   10                  15

Xaa Xaa Cys Xaa Xaa Pro
            20

<210> SEQ ID NO 42
<211> LENGTH: 19
<212> TYPE: PRT
```

```
<213> ORGANISM: Artificial Sequence
<220> FEATURE:
<223> OTHER INFORMATION: Synthetic peptide

<400> SEQUENCE: 42

Ala Asn Thr Glu Ile Ile Val Lys Leu Ser Asp Gly Arg Glu Leu Cys
1               5                   10                  15

Leu Asp Pro

<210> SEQ ID NO 43
<211> LENGTH: 19
<212> TYPE: PRT
<213> ORGANISM: Sus sp.
<220> FEATURE:
<221> NAME/KEY: MOD_RES
<222> LOCATION: (19)..(19)
<223> OTHER INFORMATION: variable amino acid

<400> SEQUENCE: 43

Arg Gly Gly Arg Leu Cys Tyr Cys Arg Arg Phe Cys Val Cys Val
1               5                   10                  15

Gly Arg Xaa

<210> SEQ ID NO 44
<211> LENGTH: 19
<212> TYPE: PRT
<213> ORGANISM: Acanthoscurria sp.
<220> FEATURE:
<221> NAME/KEY: MOD_RES
<222> LOCATION: (1)..(1)
<223> OTHER INFORMATION: variable amino acid
<220> FEATURE:
<221> NAME/KEY: MOD_RES
<222> LOCATION: (19)..(19)
<223> OTHER INFORMATION: variable amino acid

<400> SEQUENCE: 44

Xaa Cys Arg Arg Leu Cys Tyr Lys Gln Arg Cys Val Thr Tyr Cys Arg
1               5                   10                  15

Gly Arg Xaa

<210> SEQ ID NO 45
<211> LENGTH: 44
<212> TYPE: PRT
<213> ORGANISM: Drosophila sp.

<400> SEQUENCE: 45

Asp Cys Leu Ser Gly Arg Tyr Lys Gly Pro Cys Ala Val Trp Asp Asn
1               5                   10                  15

Glu Thr Cys Arg Arg Val Cys Lys Glu Glu Gly Arg Ser Ser Gly His
                20                  25                  30

Cys Ser Pro Ser Leu Lys Cys Trp Cys Glu Gly Cys
            35                  40

<210> SEQ ID NO 46
<211> LENGTH: 39
<212> TYPE: PRT
<213> ORGANISM: Mytilus sp.

<400> SEQUENCE: 46

Gly Phe Gly Cys Pro Asn Asn Tyr Gln Cys His Arg His Cys Lys Ser
1               5                   10                  15

Ile Pro Gly Arg Cys Gly Gly Tyr Cys Gly Gly Trp His Arg Leu Arg
                20                  25                  30
```

Cys Thr Cys Tyr Arg Cys Gly
            35

<210> SEQ ID NO 47
<211> LENGTH: 17
<212> TYPE: PRT
<213> ORGANISM: Tachypleus sp.

<400> SEQUENCE: 47

Lys Trp Cys Phe Arg Val Cys Tyr Arg Gly Ile Cys Tyr Arg Arg Cys
1               5                   10                  15

Arg

<210> SEQ ID NO 48
<211> LENGTH: 34
<212> TYPE: PRT
<213> ORGANISM: Mytilus sp.

<400> SEQUENCE: 48

Gly Cys Ala Ser Arg Cys Lys Ala Lys Cys Ala Gly Arg Arg Cys Lys
1               5                   10                  15

Gly Trp Ala Ser Ala Ser Phe Arg Gly Arg Cys Tyr Cys Lys Cys Phe
            20                  25                  30

Arg Cys

<210> SEQ ID NO 49
<211> LENGTH: 40
<212> TYPE: PRT
<213> ORGANISM: Protophormia sp.

<400> SEQUENCE: 49

Ala Thr Cys Asp Leu Leu Ser Gly Thr Gly Ile Asn His Ser Ala Cys
1               5                   10                  15

Ala Ala His Cys Leu Leu Arg Gly Asn Arg Gly Gly Tyr Cys Asn Gly
            20                  25                  30

Lys Ala Val Cys Val Cys Arg Asn
        35                  40

<210> SEQ ID NO 50
<211> LENGTH: 30
<212> TYPE: PRT
<213> ORGANISM: Homo sapiens

<400> SEQUENCE: 50

Asp Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 51
<211> LENGTH: 50
<212> TYPE: PRT
<213> ORGANISM: Aesculus sp.

<400> SEQUENCE: 51

Leu Cys Asn Glu Arg Pro Ser Gln Thr Trp Ser Gly Asn Cys Gly Asn
1               5                   10                  15

Thr Ala His Cys Asp Lys Gln Cys Gln Asp Trp Glu Lys Ala Ser His
            20                  25                  30

Gly Ala Cys His Lys Arg Glu Asn His Trp Lys Cys Phe Cys Tyr Phe
            35                  40                  45

-continued

```
Asn Cys
    50

<210> SEQ ID NO 52
<211> LENGTH: 50
<212> TYPE: PRT
<213> ORGANISM: Aspergillus sp.

<400> SEQUENCE: 52

Thr Tyr Asn Gly Lys Cys Tyr Lys Lys Asp Asn Ile Cys Lys Tyr Lys
1               5                   10                  15

Ala Gln Ser Gly Lys Thr Ala Ile Cys Lys Cys Tyr Val Lys Lys Cys
            20                  25                  30

Pro Arg Asp Gly Ala Lys Cys Glu Phe Asp Ser Tyr Lys Gly Lys Cys
        35                  40                  45

Tyr Cys
    50

<210> SEQ ID NO 53
<211> LENGTH: 35
<212> TYPE: PRT
<213> ORGANISM: Mus sp.
<220> FEATURE:
<221> NAME/KEY: MOD_RES
<222> LOCATION: (1)..(1)
<223> OTHER INFORMATION: variable amino acid

<400> SEQUENCE: 53

Xaa Glu Pro Val Ser Cys Ile Arg Asn Gly Gly Ile Cys Gln Tyr Arg
1               5                   10                  15

Cys Ile Gly Leu Arg His Lys Ile Gly Thr Cys Gly Ser Pro Phe Lys
            20                  25                  30

Cys Cys Lys
        35

<210> SEQ ID NO 54
<211> LENGTH: 21
<212> TYPE: PRT
<213> ORGANISM: Podisus sp.

<400> SEQUENCE: 54

Gly Ser Lys Lys Pro Val Pro Ile Ile Tyr Cys Asn Arg Arg Thr Gly
1               5                   10                  15

Lys Cys Gln Arg Met
            20

<210> SEQ ID NO 55
<211> LENGTH: 33
<212> TYPE: PRT
<213> ORGANISM: Rana sp.

<400> SEQUENCE: 55

Ser Leu Phe Ser Leu Ile Lys Ala Gly Ala Lys Phe Leu Gly Lys Asn
1               5                   10                  15

Leu Leu Lys Gln Gly Ala Cys Tyr Ala Ala Cys Lys Ala Ser Lys Gln
            20                  25                  30

Cys

<210> SEQ ID NO 56
<211> LENGTH: 30
<212> TYPE: PRT
<213> ORGANISM: Homo sapiens
```

```
<400> SEQUENCE: 56

Asp Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 57
<211> LENGTH: 34
<212> TYPE: PRT
<213> ORGANISM: Mus sp.

<400> SEQUENCE: 57

Glu Pro Val Ser Cys Ile Arg Asn Gly Gly Ile Cys Gln Tyr Arg Cys
1               5                   10                  15

Ile Gly Leu Arg His Lys Ile Gly Thr Cys Gly Ser Pro Phe Lys Cys
            20                  25                  30

Cys Lys

<210> SEQ ID NO 58
<211> LENGTH: 40
<212> TYPE: PRT
<213> ORGANISM: Protophormia sp.

<400> SEQUENCE: 58

Ala Thr Cys Asp Leu Leu Ser Gly Thr Gly Ile Asn His Ser Ala Cys
1               5                   10                  15

Ala Ala His Cys Leu Leu Arg Gly Asn Arg Gly Gly Tyr Cys Asn Gly
            20                  25                  30

Lys Gly Val Cys Val Cys Arg Asn
        35                  40

<210> SEQ ID NO 59
<211> LENGTH: 44
<212> TYPE: PRT
<213> ORGANISM: Drosophila sp.

<400> SEQUENCE: 59

Asp Cys Leu Ser Gly Arg Tyr Lys Gly Pro Cys Ala Val Trp Asp Asn
1               5                   10                  15

Glu Thr Cys Arg Arg Val Cys Lys Glu Glu Gly Arg Ser Ser Gly His
            20                  25                  30

Cys Ser Pro Ser Leu Lys Cys Trp Cys Glu Gly Cys
        35                  40

<210> SEQ ID NO 60
<211> LENGTH: 49
<212> TYPE: PRT
<213> ORGANISM: Aesculus sp.

<400> SEQUENCE: 60

Cys Asn Glu Arg Pro Ser Gln Thr Trp Ser Gly Asn Cys Gly Asn Thr
1               5                   10                  15

Ala His Cys Asp Lys Gln Cys Gln Asp Trp Glu Lys Ala Ser His Gly
            20                  25                  30

Ala Cys His Lys Arg Glu Asn His Trp Lys Cys Phe Cys Tyr Phe Asn
        35                  40                  45

Cys

<210> SEQ ID NO 61
<211> LENGTH: 39
```

<212> TYPE: PRT
<213> ORGANISM: Mytilus sp.

<400> SEQUENCE: 61

Gly Phe Gly Cys Pro Asn Asn Tyr Gln Cys His Arg His Cys Lys Ser
1               5                   10                  15

Ile Pro Gly Arg Cys Gly Gly Tyr Cys Gly Gly Trp His Arg Leu Arg
                20                  25                  30

Cys Thr Cys Tyr Arg Cys Gly
            35

<210> SEQ ID NO 62
<211> LENGTH: 18
<212> TYPE: PRT
<213> ORGANISM: Sus sp.

<400> SEQUENCE: 62

Arg Gly Val Cys Val Cys Phe Arg Arg Cys Tyr Cys Leu Arg Gly
1               5                   10                  15

Gly Arg

<210> SEQ ID NO 63
<211> LENGTH: 34
<212> TYPE: PRT
<213> ORGANISM: Mytilus sp.

<400> SEQUENCE: 63

Cys Arg Phe Cys Lys Cys Tyr Cys Arg Gly Arg Phe Ser Ala Ser Ala
1               5                   10                  15

Trp Gly Lys Cys Arg Arg Gly Ala Cys Lys Ala Lys Cys Arg Ser Ala
                20                  25                  30

Cys Gly

<210> SEQ ID NO 64
<211> LENGTH: 33
<212> TYPE: PRT
<213> ORGANISM: Rana sp.

<400> SEQUENCE: 64

Ser Leu Phe Ser Leu Ile Lys Ala Gly Ala Lys Phe Leu Gly Lys Asn
1               5                   10                  15

Leu Leu Lys Gln Gly Ala Cys Tyr Ala Ala Cys Lys Ala Ser Lys Gln
                20                  25                  30

Cys

<210> SEQ ID NO 65
<211> LENGTH: 17
<212> TYPE: PRT
<213> ORGANISM: Acanthoscurria sp.

<400> SEQUENCE: 65

Arg Gly Arg Cys Tyr Thr Val Cys Arg Gln Lys Tyr Cys Leu Arg Arg
1               5                   10                  15

Cys

<210> SEQ ID NO 66
<211> LENGTH: 21
<212> TYPE: PRT
<213> ORGANISM: Podisus sp.

<400> SEQUENCE: 66

```
Met Arg Gln Cys Lys Gly Thr Arg Arg Asn Cys Tyr Ile Ile Pro Val
1               5                   10                  15

Pro Lys Lys Ser Gly
            20

<210> SEQ ID NO 67
<211> LENGTH: 17
<212> TYPE: PRT
<213> ORGANISM: Tachypleus sp.

<400> SEQUENCE: 67

Arg Cys Arg Arg Tyr Cys Ile Gly Arg Tyr Cys Val Arg Phe Cys Trp
1               5                   10                  15

Lys

<210> SEQ ID NO 68
<211> LENGTH: 25
<212> TYPE: PRT
<213> ORGANISM: Aspergillus sp.

<400> SEQUENCE: 68

Cys Tyr Cys Lys Gly Lys Tyr Ser Asp Phe Glu Cys Lys Ala Gly Asp
1               5                   10                  15

Arg Pro Cys Lys Lys Val Tyr Cys Lys
            20                  25

<210> SEQ ID NO 69
<211> LENGTH: 18
<212> TYPE: PRT
<213> ORGANISM: Sus sp.

<400> SEQUENCE: 69

Arg Gly Val Cys Val Cys Phe Arg Arg Cys Tyr Cys Leu Arg Gly
1               5                   10                  15

Gly Arg

<210> SEQ ID NO 70
<211> LENGTH: 17
<212> TYPE: PRT
<213> ORGANISM: Acanthoscurria sp.

<400> SEQUENCE: 70

Arg Gly Arg Cys Tyr Thr Val Cys Arg Gln Lys Tyr Cys Leu Arg Arg
1               5                   10                  15

Cys

<210> SEQ ID NO 71
<211> LENGTH: 17
<212> TYPE: PRT
<213> ORGANISM: Tachypleus sp.

<400> SEQUENCE: 71

Arg Cys Arg Arg Tyr Cys Ile Gly Arg Tyr Cys Val Arg Phe Cys Trp
1               5                   10                  15

Lys

<210> SEQ ID NO 72
<211> LENGTH: 14
<212> TYPE: PRT
<213> ORGANISM: Macaca sp.

<400> SEQUENCE: 72
```

```
Cys Ile Cys Arg Cys Val Gly Arg Arg Cys Leu Cys Arg Cys
1               5                   10

<210> SEQ ID NO 73
<211> LENGTH: 12
<212> TYPE: PRT
<213> ORGANISM: Podisus sp.

<400> SEQUENCE: 73

Arg Gln Cys Lys Gly Thr Arg Arg Asn Cys Tyr Ile
1               5                   10

<210> SEQ ID NO 74
<211> LENGTH: 17
<212> TYPE: PRT
<213> ORGANISM: Homo sapiens

<400> SEQUENCE: 74

Cys Ile Phe Cys Cys Gly Cys Cys His Arg Ser Lys Cys Gly Met Cys
1               5                   10                  15

Cys

<210> SEQ ID NO 75
<211> LENGTH: 15
<212> TYPE: PRT
<213> ORGANISM: Sarcophaga sp.

<400> SEQUENCE: 75

Arg Gly Gly Tyr Cys Asn Gly Lys Ala Val Cys Val Cys Arg Asn
1               5                   10                  15

<210> SEQ ID NO 76
<211> LENGTH: 15
<212> TYPE: PRT
<213> ORGANISM: Protophormia sp.

<400> SEQUENCE: 76

Arg Gly Gly Tyr Cys Asn Gly Lys Gly Val Cys Val Cys Arg Asn
1               5                   10                  15

<210> SEQ ID NO 77
<211> LENGTH: 17
<212> TYPE: PRT
<213> ORGANISM: Heliothis sp.

<400> SEQUENCE: 77

Lys Gly Gly His Cys Gly Ser Phe Ala Asn Val Asn Cys Trp Cys Glu
1               5                   10                  15

Thr

<210> SEQ ID NO 78
<211> LENGTH: 16
<212> TYPE: PRT
<213> ORGANISM: Drosophila sp.

<400> SEQUENCE: 78

Ser Ser Gly His Cys Ser Pro Ser Leu Lys Cys Trp Cys Glu Gly Cys
1               5                   10                  15

<210> SEQ ID NO 79
<211> LENGTH: 20
<212> TYPE: PRT
<213> ORGANISM: Mytilus sp.

<400> SEQUENCE: 79
```

-continued

Arg Cys Gly Gly Tyr Cys Gly Gly Trp His Arg Leu Arg Cys Thr Cys
1               5                   10                  15

Tyr Arg Cys Gly
            20

<210> SEQ ID NO 80
<211> LENGTH: 14
<212> TYPE: PRT
<213> ORGANISM: Leiurus sp.

<400> SEQUENCE: 80

Ser Arg Gly Lys Cys Met Asn Lys Lys Cys Arg Cys Tyr Ser
1               5                   10

<210> SEQ ID NO 81
<211> LENGTH: 16
<212> TYPE: PRT
<213> ORGANISM: Homo sapiens

<400> SEQUENCE: 81

Arg Tyr Gly Thr Cys Ile Tyr Gln Gly Arg Leu Trp Ala Phe Cys Cys
1               5                   10                  15

<210> SEQ ID NO 82
<211> LENGTH: 20
<212> TYPE: PRT
<213> ORGANISM: Oryctolagus sp.

<400> SEQUENCE: 82

Glu Val Ile Asp Gly Ser Cys Gly Leu Phe Asn Ser Lys Tyr Ile Cys
1               5                   10                  15

Cys Arg Glu Lys
            20

<210> SEQ ID NO 83
<211> LENGTH: 18
<212> TYPE: PRT
<213> ORGANISM: Bos sp.

<400> SEQUENCE: 83

Met Arg Gln Ile Gly Thr Cys Phe Gly Arg Pro Val Lys Cys Cys Arg
1               5                   10                  15

Ser Trp

<210> SEQ ID NO 84
<211> LENGTH: 15
<212> TYPE: PRT
<213> ORGANISM: Homo sapiens

<400> SEQUENCE: 84

Lys Ile Gln Gly Thr Cys Tyr Arg Gly Lys Ala Lys Cys Cys Lys
1               5                   10                  15

<210> SEQ ID NO 85
<211> LENGTH: 19
<212> TYPE: PRT
<213> ORGANISM: Homo sapiens

<400> SEQUENCE: 85

Arg Tyr Lys Gln Ile Gly Thr Cys Gly Leu Pro Gly Thr Lys Cys Cys
1               5                   10                  15

Lys Lys Pro

```
<210> SEQ ID NO 86
<211> LENGTH: 14
<212> TYPE: PRT
<213> ORGANISM: Mus sp.

<400> SEQUENCE: 86

His Lys Ile Gly Thr Cys Gly Ser Pro Phe Lys Cys Cys Lys
1               5                   10

<210> SEQ ID NO 87
<211> LENGTH: 20
<212> TYPE: PRT
<213> ORGANISM: Aesculus sp.

<400> SEQUENCE: 87

Ser His Gly Ala Cys His Lys Arg Glu Asn His Trp Lys Cys Phe Cys
1               5                   10                  15

Tyr Phe Asn Cys
            20

<210> SEQ ID NO 88
<211> LENGTH: 20
<212> TYPE: PRT
<213> ORGANISM: Raphanus sp.

<400> SEQUENCE: 88

Arg His Gly Ser Cys Asn Tyr Val Phe Pro Ala His Lys Cys Ile Cys
1               5                   10                  15

Tyr Phe Pro Cys
            20

<210> SEQ ID NO 89
<211> LENGTH: 16
<212> TYPE: PRT
<213> ORGANISM: Pisum sp.

<400> SEQUENCE: 89

Ile Ser Gly Thr Cys His Asn Trp Lys Cys Phe Cys Thr Gln Asn Cys
1               5                   10                  15

<210> SEQ ID NO 90
<211> LENGTH: 18
<212> TYPE: PRT
<213> ORGANISM: Hordeum sp.

<400> SEQUENCE: 90

Gly Gly Gly Asn Cys Asp Gly Pro Leu Arg Arg Cys Lys Cys Met Arg
1               5                   10                  15

Arg Cys

<210> SEQ ID NO 91
<211> LENGTH: 18
<212> TYPE: PRT
<213> ORGANISM: Triticum sp.

<400> SEQUENCE: 91

Gly Gly Gly Asn Cys Asp Gly Pro Phe Arg Arg Cys Lys Cys Ile Arg
1               5                   10                  15

Gln Cys

<210> SEQ ID NO 92
<211> LENGTH: 19
<212> TYPE: PRT
```

<213> ORGANISM: Pentadiplandra sp.

<400> SEQUENCE: 92

Arg Ser Gly Glu Cys Phe Tyr Asp Glu Lys Arg Asn Leu Gln Cys Ile
1               5                   10                  15

Cys Asp Tyr

<210> SEQ ID NO 93
<211> LENGTH: 23
<212> TYPE: PRT
<213> ORGANISM: Artificial Sequence
<220> FEATURE:
<223> OTHER INFORMATION: Synthetic peptide
      consensus peptide
<220> FEATURE:
<221> NAME/KEY: MOD_RES
<222> LOCATION: (1)..(3)
<223> OTHER INFORMATION: variable amino acid
<220> FEATURE:
<221> NAME/KEY: MOD_RES
<222> LOCATION: (5)..(5)
<223> OTHER INFORMATION: variable amino acid
<220> FEATURE:
<221> NAME/KEY: MOD_RES
<222> LOCATION: (7)..(15)
<223> OTHER INFORMATION: variable amino acid
<220> FEATURE:
<221> NAME/KEY: MOD_RES
<222> LOCATION: (18)..(23)
<223> OTHER INFORMATION: variable amino acid

<400> SEQUENCE: 93

Xaa Xaa Xaa Gly Xaa Cys Xaa Xaa Xaa Xaa Xaa Xaa Xaa Xaa Cys
1               5                   10                  15

Cys Xaa Xaa Xaa Xaa Xaa Xaa
            20

<210> SEQ ID NO 94
<211> LENGTH: 18
<212> TYPE: PRT
<213> ORGANISM: Rattus sp.

<400> SEQUENCE: 94

Arg Leu Ser Gly Ala Cys Gly Tyr Arg Gly Arg Ile Tyr Arg Leu Cys
1               5                   10                  15

Cys Arg

<210> SEQ ID NO 95
<211> LENGTH: 18
<212> TYPE: PRT
<213> ORGANISM: Rattus sp.

<400> SEQUENCE: 95

Arg Leu Ser Gly Ala Cys Gly Tyr Arg Gly Arg Ile Tyr Arg Leu Cys
1               5                   10                  15

Cys Arg

<210> SEQ ID NO 96
<211> LENGTH: 17
<212> TYPE: PRT
<213> ORGANISM: Rattus sp.

<400> SEQUENCE: 96

Arg Leu Ser Gly Ala Cys Arg Leu Asn Gly Arg Ile Tyr Arg Leu Cys
1               5                   10                  15

Cys

<210> SEQ ID NO 97
<211> LENGTH: 17
<212> TYPE: PRT
<213> ORGANISM: Rattus sp.

<400> SEQUENCE: 97

Arg Leu Ser Gly Ala Cys Arg Leu Asn Gly Arg Ile Tyr Arg Leu Cys
1               5                   10                  15

Cys

<210> SEQ ID NO 98
<211> LENGTH: 18
<212> TYPE: PRT
<213> ORGANISM: Rattus sp.

<400> SEQUENCE: 98

Arg Leu Thr Gly Ala Cys Gly Leu Asn Gly Arg Ile Tyr Arg Leu Cys
1               5                   10                  15

Cys Arg

<210> SEQ ID NO 99
<211> LENGTH: 18
<212> TYPE: PRT
<213> ORGANISM: Homo sapiens

<400> SEQUENCE: 99

Ser Leu Ser Gly Val Cys Glu Ile Ser Gly Arg Leu Tyr Arg Leu Cys
1               5                   10                  15

Cys Arg

<210> SEQ ID NO 100
<211> LENGTH: 19
<212> TYPE: PRT
<213> ORGANISM: Oryctolagus sp.

<400> SEQUENCE: 100

Arg Arg Ala Gly Phe Cys Arg Ile Arg Gly Arg Ile His Pro Leu Cys
1               5                   10                  15

Cys Arg Arg

<210> SEQ ID NO 101
<211> LENGTH: 19
<212> TYPE: PRT
<213> ORGANISM: Oryctolagus sp.

<400> SEQUENCE: 101

Arg Arg Ala Gly Phe Cys Arg Ile Arg Gly Arg Ile His Pro Leu Cys
1               5                   10                  15

Cys Arg Arg

<210> SEQ ID NO 102
<211> LENGTH: 20
<212> TYPE: PRT
<213> ORGANISM: Oryctolagus sp.

<400> SEQUENCE: 102

Arg Phe Ser Gly Tyr Cys Arg Val Asn Gly Ala Arg Tyr Val Arg Cys
1               5                   10                  15

Cys Ser Arg Arg
            20

```
<210> SEQ ID NO 103
<211> LENGTH: 20
<212> TYPE: PRT
<213> ORGANISM: Oryctolagus sp.

<400> SEQUENCE: 103

Gln Phe Ser Gly Tyr Cys Arg Val Asn Gly Ala Arg Tyr Val Arg Cys
1               5                   10                  15

Cys Ser Arg Arg
            20

<210> SEQ ID NO 104
<211> LENGTH: 19
<212> TYPE: PRT
<213> ORGANISM: Oryctolagus sp.

<400> SEQUENCE: 104

Arg Ala Ser Gly Ser Cys Thr Val Asn Gly Val Arg His Thr Leu Cys
1               5                   10                  15

Cys Arg Arg

<210> SEQ ID NO 105
<211> LENGTH: 19
<212> TYPE: PRT
<213> ORGANISM: Oryctolagus sp.

<400> SEQUENCE: 105

Arg Ala Ser Gly Ser Cys Thr Ile Asn Gly Val Arg His Thr Leu Cys
1               5                   10                  15

Cys Arg Arg

<210> SEQ ID NO 106
<211> LENGTH: 17
<212> TYPE: PRT
<213> ORGANISM: Cavia sp.

<400> SEQUENCE: 106

Arg Arg Leu Gly Thr Cys Ile Phe Gln Asn Arg Val Tyr Thr Phe Cys
1               5                   10                  15

Cys

<210> SEQ ID NO 107
<211> LENGTH: 17
<212> TYPE: PRT
<213> ORGANISM: Cavia sp.

<400> SEQUENCE: 107

Arg Arg Leu Gly Thr Cys Ile Phe Gln Asn Arg Val Tyr Thr Phe Cys
1               5                   10                  15

Cys

<210> SEQ ID NO 108
<211> LENGTH: 17
<212> TYPE: PRT
<213> ORGANISM: Macaca sp.

<400> SEQUENCE: 108

Arg Arg Tyr Gly Thr Cys Phe Tyr Met Gly Arg Val Trp Ala Phe Cys
1               5                   10                  15

Cys
```

```
<210> SEQ ID NO 109
<211> LENGTH: 17
<212> TYPE: PRT
<213> ORGANISM: Homo sapiens

<400> SEQUENCE: 109

Arg Arg Tyr Gly Thr Cys Ile Tyr Gln Gly Arg Leu Trp Ala Phe Cys
1               5                   10                  15

Cys

<210> SEQ ID NO 110
<211> LENGTH: 21
<212> TYPE: PRT
<213> ORGANISM: Homo sapiens

<400> SEQUENCE: 110

Leu Arg Val Gly Asn Cys Leu Ile Gly Gly Val Ser Phe Thr Tyr Cys
1               5                   10                  15

Cys Thr Arg Val Asp
            20

<210> SEQ ID NO 111
<211> LENGTH: 19
<212> TYPE: PRT
<213> ORGANISM: Mesocricetus auratus

<400> SEQUENCE: 111

Arg His Ile Gly Tyr Cys Arg Phe Gly Asn Thr Ile Tyr Arg Leu Cys
1               5                   10                  15

Cys Arg Arg

<210> SEQ ID NO 112
<211> LENGTH: 19
<212> TYPE: PRT
<213> ORGANISM: Mesocricetus auratus

<400> SEQUENCE: 112

Arg Leu Ile Gly Tyr Cys Arg Phe Gly Asn Thr Ile Tyr Gly Leu Cys
1               5                   10                  15

Cys Arg Arg

<210> SEQ ID NO 113
<211> LENGTH: 19
<212> TYPE: PRT
<213> ORGANISM: Mesocricetus auratus

<400> SEQUENCE: 113

Thr Gln Ile Gly Tyr Cys Arg Leu Gly Asn Thr Phe Tyr Arg Leu Cys
1               5                   10                  15

Cys Arg Gln

<210> SEQ ID NO 114
<211> LENGTH: 19
<212> TYPE: PRT
<213> ORGANISM: Mesocricetus auratus

<400> SEQUENCE: 114

Thr Gln Ile Gly Tyr Cys Arg Leu Gly Asn Thr Phe Tyr Arg Leu Cys
1               5                   10                  15

Cys Arg Gln

<210> SEQ ID NO 115
```

<211> LENGTH: 18
<212> TYPE: PRT
<213> ORGANISM: Mus sp.

<400> SEQUENCE: 115

Arg Met Asn Gly Thr Cys Arg Lys Gly His Leu Leu Tyr Thr Leu Cys
1               5                   10                  15

Cys Arg

<210> SEQ ID NO 116
<211> LENGTH: 18
<212> TYPE: PRT
<213> ORGANISM: Mus sp.

<400> SEQUENCE: 116

Arg Met Asn Gly Thr Cys Arg Lys Gly His Leu Leu Tyr Met Leu Cys
1               5                   10                  15

Cys Arg

<210> SEQ ID NO 117
<211> LENGTH: 18
<212> TYPE: PRT
<213> ORGANISM: Mus sp.

<400> SEQUENCE: 117

Arg Met Asn Gly Thr Cys Arg Lys Gly His Leu Met Tyr Thr Leu Cys
1               5                   10                  15

Cys Arg

<210> SEQ ID NO 118
<211> LENGTH: 18
<212> TYPE: PRT
<213> ORGANISM: Mus sp.

<400> SEQUENCE: 118

Arg Met Asn Gly Thr Cys Arg Lys Gly His Leu Leu Tyr Met Leu Cys
1               5                   10                  15

Cys Arg

<210> SEQ ID NO 119
<211> LENGTH: 18
<212> TYPE: PRT
<213> ORGANISM: Mus sp.

<400> SEQUENCE: 119

Arg Met Asn Gly Thr Cys Arg Lys Gly His Leu Leu Tyr Thr Met Cys
1               5                   10                  15

Cys Arg

<210> SEQ ID NO 120
<211> LENGTH: 18
<212> TYPE: PRT
<213> ORGANISM: Mus sp.

<400> SEQUENCE: 120

Arg Met Asn Gly Thr Cys Arg Lys Gly His Leu Met Tyr Thr Leu Cys
1               5                   10                  15

Cys Arg

<210> SEQ ID NO 121
<211> LENGTH: 18
<212> TYPE: PRT

<213> ORGANISM: Mus sp.

<400> SEQUENCE: 121

Arg Met Asn Gly Thr Cys Arg Lys Gly His Leu Met His Thr Leu Cys
1               5                   10                  15

Cys Arg

<210> SEQ ID NO 122
<211> LENGTH: 18
<212> TYPE: PRT
<213> ORGANISM: Mus sp.

<400> SEQUENCE: 122

His Met Asn Gly Thr Cys Arg Lys Gly His Leu Met Tyr Thr Leu Cys
1               5                   10                  15

Cys Arg

<210> SEQ ID NO 123
<211> LENGTH: 18
<212> TYPE: PRT
<213> ORGANISM: Mus sp.

<400> SEQUENCE: 123

His Met Asn Gly Thr Cys Arg Arg Gly His Leu Met Tyr Thr Leu Cys
1               5                   10                  15

Cys Arg

<210> SEQ ID NO 124
<211> LENGTH: 18
<212> TYPE: PRT
<213> ORGANISM: Mus sp.

<400> SEQUENCE: 124

His Met Asn Gly Thr Cys Arg Lys Gly His Leu Met Tyr Thr Leu Cys
1               5                   10                  15

Cys Arg

<210> SEQ ID NO 125
<211> LENGTH: 18
<212> TYPE: PRT
<213> ORGANISM: Mus sp.

<400> SEQUENCE: 125

Arg Met Asn Gly Thr Cys Arg Lys Gly His Leu Met Tyr Thr Leu Cys
1               5                   10                  15

Cys Arg

<210> SEQ ID NO 126
<211> LENGTH: 18
<212> TYPE: PRT
<213> ORGANISM: Mus sp.

<400> SEQUENCE: 126

His Met Asn Gly Thr Cys Arg Lys Gly His Leu Leu Tyr Met Leu Cys
1               5                   10                  15

Cys Arg

<210> SEQ ID NO 127
<211> LENGTH: 18
<212> TYPE: PRT
<213> ORGANISM: Mus sp.

```
<400> SEQUENCE: 127

His Ile Asn Gly Thr Cys Arg Lys Gly His Leu Leu Tyr Met Leu Cys
1               5                   10                  15

Cys Arg

<210> SEQ ID NO 128
<211> LENGTH: 18
<212> TYPE: PRT
<213> ORGANISM: Mus sp.

<400> SEQUENCE: 128

His Met Asn Gly Thr Cys Arg Lys Gly His Leu Leu Tyr Thr Leu Cys
1               5                   10                  15

Cys Arg

<210> SEQ ID NO 129
<211> LENGTH: 17
<212> TYPE: PRT
<213> ORGANISM: Mus sp.

<400> SEQUENCE: 129

Arg Val Arg Gly Thr Cys Gly Ile Arg Phe Leu Tyr Cys Cys Pro Arg
1               5                   10                  15

Arg

<210> SEQ ID NO 130
<211> LENGTH: 20
<212> TYPE: PRT
<213> ORGANISM: Mus sp.

<400> SEQUENCE: 130

Arg Val Phe Gly Thr Cys Arg Asn Leu Phe Leu Thr Phe Val Phe Cys
1               5                   10                  15

Cys Ser Arg Arg
            20

<210> SEQ ID NO 131
<211> LENGTH: 18
<212> TYPE: PRT
<213> ORGANISM: Rattus sp.

<400> SEQUENCE: 131

Gly Ile Met Gly Ile Cys Lys Lys Arg Tyr Gly Ser Pro Ile Leu Cys
1               5                   10                  15

Cys Arg

<210> SEQ ID NO 132
<211> LENGTH: 14
<212> TYPE: PRT
<213> ORGANISM: Mus sp.

<400> SEQUENCE: 132

His Lys Ile Gly Thr Cys Gly Ser Pro Phe Lys Cys Cys Arg
1               5                   10

<210> SEQ ID NO 133
<211> LENGTH: 17
<212> TYPE: PRT
<213> ORGANISM: Bos sp.

<400> SEQUENCE: 133

Ile Gln Ile Gly Ile Cys Phe Arg Pro Arg Val Lys Cys Cys Arg Ser
```

-continued

```
1               5                   10                  15

Trp

<210> SEQ ID NO 134
<211> LENGTH: 15
<212> TYPE: PRT
<213> ORGANISM: Bos sp.

<400> SEQUENCE: 134

Arg Gln Ile Gly Thr Cys Leu Ala Pro Arg Val Lys Cys Cys Arg
1               5                   10                  15

<210> SEQ ID NO 135
<211> LENGTH: 17
<212> TYPE: PRT
<213> ORGANISM: Capra hircus

<400> SEQUENCE: 135

Arg Gln Ile Gly Thr Cys Phe Gly Pro Pro Val Lys Cys Cys Arg Lys
1               5                   10                  15

Lys

<210> SEQ ID NO 136
<211> LENGTH: 17
<212> TYPE: PRT
<213> ORGANISM: Ovis sp.

<400> SEQUENCE: 136

Arg Gln Ile Gly Thr Cys Phe Gly Pro Pro Val Lys Cys Cys Arg Leu
1               5                   10                  15

Lys

<210> SEQ ID NO 137
<211> LENGTH: 17
<212> TYPE: PRT
<213> ORGANISM: Bos sp.

<400> SEQUENCE: 137

Arg Gln Ile Gly Thr Cys Phe Gly Arg Pro Val Lys Cys Cys Arg Ser
1               5                   10                  15

Trp

<210> SEQ ID NO 138
<211> LENGTH: 17
<212> TYPE: PRT
<213> ORGANISM: Bos sp.

<400> SEQUENCE: 138

Arg Gln Ile Gly Thr Cys Phe Gly Arg Pro Val Lys Cys Cys Arg Ser
1               5                   10                  15

Trp

<210> SEQ ID NO 139
<211> LENGTH: 17
<212> TYPE: PRT
<213> ORGANISM: Bos sp.

<400> SEQUENCE: 139

Arg Gln Ile Gly Thr Cys Phe Gly Arg Pro Val Lys Cys Cys Arg Ser
1               5                   10                  15

Trp
```

```
<210> SEQ ID NO 140
<211> LENGTH: 17
<212> TYPE: PRT
<213> ORGANISM: Bos sp.

<400> SEQUENCE: 140

Arg Gln Ile Gly Thr Cys Phe Gly Arg Pro Val Lys Cys Cys Arg Ser
1               5                   10                  15

Trp

<210> SEQ ID NO 141
<211> LENGTH: 17
<212> TYPE: PRT
<213> ORGANISM: Ovis sp.

<400> SEQUENCE: 141

Arg Gln Ile Gly Thr Cys Arg Gly Pro Pro Val Lys Cys Cys Arg Lys
1               5                   10                  15

Lys

<210> SEQ ID NO 142
<211> LENGTH: 17
<212> TYPE: PRT
<213> ORGANISM: Bos sp.

<400> SEQUENCE: 142

Arg Gln Ile Gly Thr Cys Phe Gly Pro Arg Ile Lys Cys Cys Arg Ser
1               5                   10                  15

Trp

<210> SEQ ID NO 143
<211> LENGTH: 17
<212> TYPE: PRT
<213> ORGANISM: Bos sp.

<400> SEQUENCE: 143

Arg Gln Ile Gly Thr Cys Phe Gly Pro Arg Ile Lys Cys Cys Arg Ser
1               5                   10                  15

Trp

<210> SEQ ID NO 144
<211> LENGTH: 17
<212> TYPE: PRT
<213> ORGANISM: Bos sp.

<400> SEQUENCE: 144

Arg Gln Ile Gly Thr Cys Phe Gly Arg Pro Val Lys Cys Cys Arg Arg
1               5                   10                  15

Trp

<210> SEQ ID NO 145
<211> LENGTH: 15
<212> TYPE: PRT
<213> ORGANISM: Bos sp.

<400> SEQUENCE: 145

Arg Gln Ile Gly Thr Cys Leu Gly Pro Gln Ile Lys Cys Cys Arg
1               5                   10                  15

<210> SEQ ID NO 146
<211> LENGTH: 15
<212> TYPE: PRT
```

```
<213> ORGANISM: Bos sp.

<400> SEQUENCE: 146

Arg Gln Ile Gly Thr Cys Leu Ala Pro Gln Ile Lys Cys Cys Arg
1               5                   10                  15

<210> SEQ ID NO 147
<211> LENGTH: 15
<212> TYPE: PRT
<213> ORGANISM: Bos sp.

<400> SEQUENCE: 147

Arg Gln Ile Gly Thr Cys Leu Gly Pro Arg Ile Lys Cys Cys Arg
1               5                   10                  15

<210> SEQ ID NO 148
<211> LENGTH: 17
<212> TYPE: PRT
<213> ORGANISM: Bos sp.

<400> SEQUENCE: 148

Arg Gln Ile Gly Thr Cys Leu Gly Ala Gln Val Lys Cys Cys Arg Arg
1               5                   10                  15

Lys

<210> SEQ ID NO 149
<211> LENGTH: 17
<212> TYPE: PRT
<213> ORGANISM: Bos sp.

<400> SEQUENCE: 149

Lys Gln Ile Gly Thr Cys Val Gly Arg Ala Val Lys Cys Cys Arg Lys
1               5                   10                  15

Lys

<210> SEQ ID NO 150
<211> LENGTH: 17
<212> TYPE: PRT
<213> ORGANISM: Bos sp.

<400> SEQUENCE: 150

Arg Gln Ile Gly Thr Cys Phe Thr Pro Ser Val Lys Cys Cys Arg Trp
1               5                   10                  15

Arg

<210> SEQ ID NO 151
<211> LENGTH: 16
<212> TYPE: PRT
<213> ORGANISM: Bos sp.

<400> SEQUENCE: 151

Arg Gln Ile Gly Thr Cys Phe Gly Pro Arg Val Pro Cys Cys Arg Arg
1               5                   10                  15

<210> SEQ ID NO 152
<211> LENGTH: 17
<212> TYPE: PRT
<213> ORGANISM: Bos sp.

<400> SEQUENCE: 152

Arg Gln Ile Gly Thr Cys Phe Gly Pro Arg Val Pro Cys Cys Arg Arg
1               5                   10                  15

Trp
```

<210> SEQ ID NO 153
<211> LENGTH: 17
<212> TYPE: PRT
<213> ORGANISM: Sus sp.

<400> SEQUENCE: 153

Lys Gln Ile Gly Thr Cys Gly Met Pro Gln Val Lys Cys Cys Lys Arg
1               5                   10                  15

Lys

<210> SEQ ID NO 154
<211> LENGTH: 17
<212> TYPE: PRT
<213> ORGANISM: Homo sapiens

<400> SEQUENCE: 154

Lys Gln Ile Gly Thr Cys Gly Leu Pro Gly Thr Lys Cys Cys Lys Lys
1               5                   10                  15

Pro

<210> SEQ ID NO 155
<211> LENGTH: 17
<212> TYPE: PRT
<213> ORGANISM: Rattus sp.

<400> SEQUENCE: 155

Arg Gln Ile Gly Thr Cys Gly Leu Pro Arg Val Arg Cys Cys Lys Lys
1               5                   10                  15

Lys

<210> SEQ ID NO 156
<211> LENGTH: 17
<212> TYPE: PRT
<213> ORGANISM: Mus sp.

<400> SEQUENCE: 156

Arg Gln Ile Gly Asn Cys Gly His Phe Lys Val Arg Cys Cys Lys Ile
1               5                   10                  15

Arg

<210> SEQ ID NO 157
<211> LENGTH: 17
<212> TYPE: PRT
<213> ORGANISM: Mus sp.

<400> SEQUENCE: 157

Arg Gln Ile Gly Ser Cys Gly Val Phe Pro Leu Lys Cys Cys Lys Arg
1               5                   10                  15

Lys

<210> SEQ ID NO 158
<211> LENGTH: 15
<212> TYPE: PRT
<213> ORGANISM: Homo sapiens

<400> SEQUENCE: 158

Lys Ile Gln Gly Thr Cys Tyr Arg Gly Lys Ala Lys Cys Cys Lys
1               5                   10                  15

<210> SEQ ID NO 159
<211> LENGTH: 15

<212> TYPE: PRT
<213> ORGANISM: Macaca mulatta

<400> SEQUENCE: 159

Arg Ile Gln Gly Thr Cys Tyr His Gly Lys Ala Lys Cys Cys Lys
1               5                   10                  15

<210> SEQ ID NO 160
<211> LENGTH: 16
<212> TYPE: PRT
<213> ORGANISM: Mus sp.

<400> SEQUENCE: 160

Lys Leu Gln Gly Thr Cys Lys Pro Asp Lys Pro Asn Cys Cys Lys Ser
1               5                   10                  15

<210> SEQ ID NO 161
<211> LENGTH: 16
<212> TYPE: PRT
<213> ORGANISM: Rattus sp.

<400> SEQUENCE: 161

Lys Leu Gln Gly Thr Cys Lys Pro Asp Lys Pro Asn Cys Cys Arg Ser
1               5                   10                  15

<210> SEQ ID NO 162
<211> LENGTH: 18
<212> TYPE: PRT
<213> ORGANISM: Mus sp.

<400> SEQUENCE: 162

Arg Arg Pro Gly Ser Cys Phe Pro Glu Lys Asn Pro Cys Cys Lys Tyr
1               5                   10                  15

Met Lys

<210> SEQ ID NO 163
<211> LENGTH: 18
<212> TYPE: PRT
<213> ORGANISM: Homo sapiens

<400> SEQUENCE: 163

Glu Gln Ile Gly Lys Cys Ser Thr Arg Gly Arg Lys Cys Cys Arg Arg
1               5                   10                  15

Lys Lys

<210> SEQ ID NO 164
<211> LENGTH: 17
<212> TYPE: PRT
<213> ORGANISM: Gallus sp.

<400> SEQUENCE: 164

Leu Ile Ser Gly Lys Cys Ser Arg Phe Tyr Leu Cys Cys Lys Arg Ile
1               5                   10                  15

Arg

<210> SEQ ID NO 165
<211> LENGTH: 17
<212> TYPE: PRT
<213> ORGANISM: Gallus sp.

<400> SEQUENCE: 165

Leu Ile Ser Gly Lys Cys Ser Arg Phe Tyr Leu Cys Cys Arg Ile Trp
1               5                   10                  15

Gly

<210> SEQ ID NO 166
<211> LENGTH: 17
<212> TYPE: PRT
<213> ORGANISM: Gallus sp.

<400> SEQUENCE: 166

Leu Ile Ser Gly Lys Cys Ser Arg Phe His Leu Cys Cys Lys Arg Ile
1               5                   10                  15

Trp

<210> SEQ ID NO 167
<211> LENGTH: 18
<212> TYPE: PRT
<213> ORGANISM: Meleagris gallopavo

<400> SEQUENCE: 167

Val Ile Ser Gly Thr Cys Ser Arg Phe Gln Val Cys Cys Lys Thr Leu
1               5                   10                  15

Leu Gly

<210> SEQ ID NO 168
<211> LENGTH: 19
<212> TYPE: PRT
<213> ORGANISM: Meleagris gallopavo

<400> SEQUENCE: 168

Ile Lys Val Gly Ser Cys Phe Gly Phe Arg Ser Cys Cys Lys Trp Pro
1               5                   10                  15

Trp Asp Ala

<210> SEQ ID NO 169
<211> LENGTH: 19
<212> TYPE: PRT
<213> ORGANISM: Gallus sp.

<400> SEQUENCE: 169

Ile Lys Val Gly Ser Cys Phe Gly Phe Arg Ser Cys Cys Lys Trp Pro
1               5                   10                  15

Trp Asn Ala

<210> SEQ ID NO 170
<211> LENGTH: 19
<212> TYPE: PRT
<213> ORGANISM: Oryctolagus sp.

<400> SEQUENCE: 170

Val Ile Asp Gly Ser Cys Gly Leu Phe Asn Ser Lys Tyr Ile Cys Cys
1               5                   10                  15

Arg Glu Lys

<210> SEQ ID NO 171
<211> LENGTH: 17
<212> TYPE: PRT
<213> ORGANISM: Homo sapiens

<400> SEQUENCE: 171

Ile His Val Gly Arg Cys Leu Asn Ser Gln Pro Cys Cys Leu Pro Leu
1               5                   10                  15

Gly

```
<210> SEQ ID NO 172
<211> LENGTH: 18
<212> TYPE: PRT
<213> ORGANISM: Homo sapiens

<400> SEQUENCE: 172

Tyr Ser Tyr Gly Thr Cys Thr Val Met Gly Ile Asn His Arg Phe Cys
1               5                   10                  15

Cys Leu

<210> SEQ ID NO 173
<211> LENGTH: 17
<212> TYPE: PRT
<213> ORGANISM: Homo sapiens

<400> SEQUENCE: 173

Tyr Arg Ile Gly Arg Cys Pro Asn Thr Tyr Ala Cys Cys Leu Arg Lys
1               5                   10                  15

Trp

<210> SEQ ID NO 174
<211> LENGTH: 22
<212> TYPE: PRT
<213> ORGANISM: Artificial Sequence
<220> FEATURE:
<223> OTHER INFORMATION: Synthetic peptide
      consensus peptide
<220> FEATURE:
<221> NAME/KEY: MOD_RES
<222> LOCATION: (1)..(3)
<223> OTHER INFORMATION: variable amino acid
<220> FEATURE:
<221> NAME/KEY: MOD_RES
<222> LOCATION: (5)..(5)
<223> OTHER INFORMATION: variable amino acid
<220> FEATURE:
<221> NAME/KEY: MOD_RES
<222> LOCATION: (7)..(14)
<223> OTHER INFORMATION: variable amino acid
<220> FEATURE:
<221> NAME/KEY: MOD_RES
<222> LOCATION: (16)..(16)
<223> OTHER INFORMATION: variable amino acid
<220> FEATURE:
<221> NAME/KEY: MOD_RES
<222> LOCATION: (18)..(22)
<223> OTHER INFORMATION: variable amino acid

<400> SEQUENCE: 174

Xaa Xaa Xaa Gly Xaa Cys Xaa Xaa Xaa Xaa Xaa Xaa Xaa Cys Xaa
1               5                   10                  15

Cys Xaa Xaa Xaa Xaa Xaa
            20

<210> SEQ ID NO 175
<211> LENGTH: 21
<212> TYPE: PRT
<213> ORGANISM: Arabidopsis thaliana

<400> SEQUENCE: 175

Ala Arg His Gly Ser Cys Asn Tyr Val Phe Pro Ala His Lys Cys Ile
1               5                   10                  15

Cys Tyr Phe Pro Cys
            20

<210> SEQ ID NO 176
<211> LENGTH: 21
```

```
<212> TYPE: PRT
<213> ORGANISM: Brassica napus

<400> SEQUENCE: 176

Ala Arg His Gly Ser Cys Asn Tyr Val Phe Pro Ala His Lys Cys Ile
1               5                   10                  15

Cys Tyr Phe Pro Cys
            20

<210> SEQ ID NO 177
<211> LENGTH: 21
<212> TYPE: PRT
<213> ORGANISM: Sinapis alba

<400> SEQUENCE: 177

Ala Arg His Gly Ser Cys Asn Tyr Val Phe Pro Ala His Lys Cys Ile
1               5                   10                  15

Cys Tyr Phe Pro Cys
            20

<210> SEQ ID NO 178
<211> LENGTH: 21
<212> TYPE: PRT
<213> ORGANISM: Raphanus sativus

<400> SEQUENCE: 178

Ala Arg His Gly Ser Cys Asn Tyr Val Phe Pro Ala His Lys Cys Ile
1               5                   10                  15

Cys Tyr Phe Pro Cys
            20

<210> SEQ ID NO 179
<211> LENGTH: 21
<212> TYPE: PRT
<213> ORGANISM: Raphanus sativus

<400> SEQUENCE: 179

Ala Arg His Gly Ser Cys Asn Tyr Val Phe Pro Ala His Lys Cys Ile
1               5                   10                  15

Cys Tyr Phe Pro Cys
            20

<210> SEQ ID NO 180
<211> LENGTH: 21
<212> TYPE: PRT
<213> ORGANISM: Sinapis alba

<400> SEQUENCE: 180

Ala Arg His Gly Ser Cys Asn Tyr Val Phe Pro Ala His Lys Cys Ile
1               5                   10                  15

Cys Tyr Phe Pro Cys
            20

<210> SEQ ID NO 181
<211> LENGTH: 21
<212> TYPE: PRT
<213> ORGANISM: Arabidopsis thaliana

<400> SEQUENCE: 181

Ala Lys His Gly Ser Cys Asn Tyr Val Phe Pro Ala His Lys Cys Ile
1               5                   10                  15

Cys Tyr Phe Pro Cys
            20
```

```
<210> SEQ ID NO 182
<211> LENGTH: 21
<212> TYPE: PRT
<213> ORGANISM: Arabidopsis thaliana

<400> SEQUENCE: 182

Ala Lys His Gly Ser Cys Asn Tyr Val Phe Pro Ala His Lys Cys Ile
1               5                   10                  15

Cys Tyr Val Pro Cys
            20

<210> SEQ ID NO 183
<211> LENGTH: 21
<212> TYPE: PRT
<213> ORGANISM: Arabidopsis thaliana

<400> SEQUENCE: 183

Ala Lys His Gly Ser Cys Asn Tyr Val Phe Pro Ala His Lys Cys Ile
1               5                   10                  15

Cys Tyr Val Pro Cys
            20

<210> SEQ ID NO 184
<211> LENGTH: 21
<212> TYPE: PRT
<213> ORGANISM: Brassica napus

<400> SEQUENCE: 184

Ala Gln His Gly Ser Cys Asn Tyr Val Phe Pro Ala His Lys Cys Ile
1               5                   10                  15

Cys Tyr Phe Pro Cys
            20

<210> SEQ ID NO 185
<211> LENGTH: 21
<212> TYPE: PRT
<213> ORGANISM: Raphanus sativus

<400> SEQUENCE: 185

Ala Gln His Gly Ser Cys Asn Tyr Val Phe Pro Ala His Lys Cys Ile
1               5                   10                  15

Cys Tyr Phe Pro Cys
            20

<210> SEQ ID NO 186
<211> LENGTH: 21
<212> TYPE: PRT
<213> ORGANISM: Raphanus sativus

<400> SEQUENCE: 186

Ala Arg His Gly Ser Cys Asn Tyr Val Phe Pro Tyr His Arg Cys Ile
1               5                   10                  15

Cys Tyr Phe Pro Cys
            20

<210> SEQ ID NO 187
<211> LENGTH: 21
<212> TYPE: PRT
<213> ORGANISM: Sinapis alba

<400> SEQUENCE: 187

Ser Arg His Gly Ser Cys Asn Ile Pro Phe Pro Ser Asn Lys Cys Ile
```

```
1               5                  10                 15
Cys Tyr Phe Pro Cys
            20
```

<210> SEQ ID NO 188
<211> LENGTH: 21
<212> TYPE: PRT
<213> ORGANISM: Aesculus hippocastanum

<400> SEQUENCE: 188

```
Ala Ser His Gly Ala Cys His Lys Arg Glu Asn His Trp Lys Cys Phe
1               5                  10                 15
Cys Tyr Phe Asn Cys
            20
```

<210> SEQ ID NO 189
<211> LENGTH: 19
<212> TYPE: PRT
<213> ORGANISM: Nicotiana paniculata

<400> SEQUENCE: 189

```
Phe Thr Asp Gly Lys Cys Ser Lys Ile Leu Arg Arg Cys Ile Cys Tyr
1               5                  10                 15
Lys Pro Cys
```

<210> SEQ ID NO 190
<211> LENGTH: 19
<212> TYPE: PRT
<213> ORGANISM: Nicotiana tabacum

<400> SEQUENCE: 190

```
Phe Thr Asp Gly His Cys Ser Lys Leu Leu Arg Arg Cys Ile Cys Thr
1               5                  10                 15
Lys Pro Cys
```

<210> SEQ ID NO 191
<211> LENGTH: 18
<212> TYPE: PRT
<213> ORGANISM: Beta vulgaris

<400> SEQUENCE: 191

```
Trp Pro Gly Gly Val Cys Val Pro Phe Leu Arg Cys Glu Cys Gln Arg
1               5                  10                 15
Ser Cys
```

<210> SEQ ID NO 192
<211> LENGTH: 18
<212> TYPE: PRT
<213> ORGANISM: Beta vulgaris

<400> SEQUENCE: 192

```
Trp Pro Asn Gly Lys Cys Leu Val Gly Phe Lys Cys Glu Cys Gln Arg
1               5                  10                 15
Pro Cys
```

<210> SEQ ID NO 193
<211> LENGTH: 18
<212> TYPE: PRT
<213> ORGANISM: Pisum sp.

<400> SEQUENCE: 193

```
Ala Ile Ser Gly Arg Cys Arg Asp Asp Phe Arg Cys Trp Cys Thr Lys
```

```
1               5                   10                  15
Asn Cys

<210> SEQ ID NO 194
<211> LENGTH: 18
<212> TYPE: PRT
<213> ORGANISM: Pisum sp.

<400> SEQUENCE: 194

Leu Leu Ser Gly Arg Cys Arg Asp Asp Phe Arg Cys Trp Cys Thr Asn
1               5                   10                  15

Arg Cys

<210> SEQ ID NO 195
<211> LENGTH: 16
<212> TYPE: PRT
<213> ORGANISM: Drosophila melanogaster

<400> SEQUENCE: 195

Arg Ser Ser Gly His Cys Ser Pro Ser Leu Lys Cys Trp Cys Glu Gly
1               5                   10                  15

<210> SEQ ID NO 196
<211> LENGTH: 19
<212> TYPE: PRT
<213> ORGANISM: Capsicum annuum

<400> SEQUENCE: 196

Phe Asn Gly Gly His Cys Arg Gly Phe Arg Arg Cys Phe Cys Thr
1               5                   10                  15

Arg His Cys

<210> SEQ ID NO 197
<211> LENGTH: 19
<212> TYPE: PRT
<213> ORGANISM: Petunia integrifolia

<400> SEQUENCE: 197

Phe Ile Gly Gly Asn Cys Arg Ala Phe Arg Arg Cys Phe Cys Thr
1               5                   10                  15

Arg Asn Cys

<210> SEQ ID NO 198
<211> LENGTH: 19
<212> TYPE: PRT
<213> ORGANISM: Arabidopsis thaliana

<400> SEQUENCE: 198

Phe Val Gly Gly Asn Cys Arg Gly Phe Arg Arg Cys Phe Cys Thr
1               5                   10                  15

Arg His Cys

<210> SEQ ID NO 199
<211> LENGTH: 19
<212> TYPE: PRT
<213> ORGANISM: Arabidopsis thaliana

<400> SEQUENCE: 199

Phe Pro Gly Gly Asp Cys Arg Gly Phe Arg Arg Cys Phe Cys Thr
1               5                   10                  15

Arg Asn Cys
```

```
<210> SEQ ID NO 200
<211> LENGTH: 19
<212> TYPE: PRT
<213> ORGANISM: Arabidopsis thaliana

<400> SEQUENCE: 200

Phe Gly Gly Gly Lys Cys Arg Gly Phe Arg Arg Cys Tyr Cys Thr
1               5                   10                  15

Arg His Cys

<210> SEQ ID NO 201
<211> LENGTH: 19
<212> TYPE: PRT
<213> ORGANISM: Helianthus annuus

<400> SEQUENCE: 201

Phe Ser Gly Gly Lys Cys Arg Gly Phe Arg Arg Cys Phe Cys Thr
1               5                   10                  15

Thr His Cys

<210> SEQ ID NO 202
<211> LENGTH: 19
<212> TYPE: PRT
<213> ORGANISM: Vigna unguiculata

<400> SEQUENCE: 202

Phe Ser Gly Gly Asn Cys Arg Gly Phe Arg Arg Cys Phe Cys Thr
1               5                   10                  15

Leu Lys Cys

<210> SEQ ID NO 203
<211> LENGTH: 20
<212> TYPE: PRT
<213> ORGANISM: Capsicum annuum

<400> SEQUENCE: 203

Phe Thr Asp Gly Ser Cys Ile Gly Phe Arg Leu Gln Cys Phe Cys Thr
1               5                   10                  15

Lys Pro Cys Ala
            20

<210> SEQ ID NO 204
<211> LENGTH: 17
<212> TYPE: PRT
<213> ORGANISM: Vicia faba

<400> SEQUENCE: 204

Tyr Lys Gly Gly Asp Cys His Gly Leu Arg Arg Arg Cys Met Cys Leu
1               5                   10                  15

Cys

<210> SEQ ID NO 205
<211> LENGTH: 17
<212> TYPE: PRT
<213> ORGANISM: Vicia faba

<400> SEQUENCE: 205

Tyr Lys Gly Gly Asp Cys His Gly Leu Arg Arg Arg Cys Met Cys Leu
1               5                   10                  15

Cys
```

<210> SEQ ID NO 206
<211> LENGTH: 19
<212> TYPE: PRT
<213> ORGANISM: Spinacia oleracea

<400> SEQUENCE: 206

Tyr Pro Ala Gly Asp Cys Lys Gly Ile Arg Arg Arg Cys Met Cys Ser
1               5                   10                  15

Lys Pro Cys

<210> SEQ ID NO 207
<211> LENGTH: 19
<212> TYPE: PRT
<213> ORGANISM: Triticum aestivum

<400> SEQUENCE: 207

Trp Gly Gly Gly Asn Cys Asp Gly Pro Phe Arg Arg Cys Lys Cys Ile
1               5                   10                  15

Arg Gln Cys

<210> SEQ ID NO 208
<211> LENGTH: 19
<212> TYPE: PRT
<213> ORGANISM: Triticum aestivum

<400> SEQUENCE: 208

Trp Gly Gly Gly Asn Cys Asp Gly Pro Phe Arg Arg Cys Lys Cys Ile
1               5                   10                  15

Arg Gln Cys

<210> SEQ ID NO 209
<211> LENGTH: 19
<212> TYPE: PRT
<213> ORGANISM: Hordeum vulgare

<400> SEQUENCE: 209

Trp Gly Gly Gly Asn Cys Asp Gly Pro Phe Arg Arg Cys Lys Cys Met
1               5                   10                  15

Arg Arg Cys

<210> SEQ ID NO 210
<211> LENGTH: 19
<212> TYPE: PRT
<213> ORGANISM: Zea mays

<400> SEQUENCE: 210

Tyr Gly Gly Gly Asn Cys Asp Gly Ile Met Arg Gln Cys Lys Cys Ile
1               5                   10                  15

Arg Gln Cys

<210> SEQ ID NO 211
<211> LENGTH: 16
<212> TYPE: PRT
<213> ORGANISM: Protophormia terraenovae

<400> SEQUENCE: 211

Asn Arg Gly Gly Tyr Cys Asn Gly Lys Gly Val Cys Val Cys Arg Asn
1               5                   10                  15

<210> SEQ ID NO 212
<211> LENGTH: 16
<212> TYPE: PRT
<213> ORGANISM: Sarcophaga peregrina

<400> SEQUENCE: 212

Asn Arg Gly Gly Tyr Cys Asn Gly Lys Ala Val Cys Val Cys Arg Asn
1               5                   10                  15

<210> SEQ ID NO 213
<211> LENGTH: 15
<212> TYPE: PRT
<213> ORGANISM: Tenebrio molitor

<400> SEQUENCE: 213

Arg Ser Gly Gly Tyr Cys Asn Gly Lys Arg Val Cys Val Cys Arg
1               5                   10                  15

<210> SEQ ID NO 214
<211> LENGTH: 16
<212> TYPE: PRT
<213> ORGANISM: Sarcophaga peregrina

<400> SEQUENCE: 214

Asn Arg Gly Gly Tyr Cys Thr Gly Asn Gly Ile Cys Val Cys Arg Asn
1               5                   10                  15

<210> SEQ ID NO 215
<211> LENGTH: 16
<212> TYPE: PRT
<213> ORGANISM: Stomoxys calcitrans

<400> SEQUENCE: 215

Asp Val Gly Gly Tyr Cys Thr Lys Glu Gly Leu Cys Val Cys Lys Glu
1               5                   10                  15

<210> SEQ ID NO 216
<211> LENGTH: 16
<212> TYPE: PRT
<213> ORGANISM: Aedes aegypti

<400> SEQUENCE: 216

Asn Arg Gly Gly Tyr Cys Asn Ala Lys Lys Val Cys Val Cys Arg Asn
1               5                   10                  15

<210> SEQ ID NO 217
<211> LENGTH: 16
<212> TYPE: PRT
<213> ORGANISM: Anopheles gambiae

<400> SEQUENCE: 217

Tyr Arg Gly Gly Tyr Cys Asn Ser Lys Ala Val Cys Val Cys Arg Asn
1               5                   10                  15

<210> SEQ ID NO 218
<211> LENGTH: 16
<212> TYPE: PRT
<213> ORGANISM: Aedes aegypti

<400> SEQUENCE: 218

Asn Arg Gly Gly Tyr Cys Asn Ser Gln Lys Val Cys Val Cys Arg Asn
1               5                   10                  15

<210> SEQ ID NO 219
<211> LENGTH: 16
<212> TYPE: PRT
<213> ORGANISM: Phlebotomus duboscqi

<400> SEQUENCE: 219

Tyr Arg Gly Gly Tyr Cys Asn Ser Lys Ala Val Cys Thr Cys Arg Arg
1               5                   10                  15

<210> SEQ ID NO 220
<211> LENGTH: 16
<212> TYPE: PRT
<213> ORGANISM: Drosophila melanogaster

<400> SEQUENCE: 220

Phe Lys Gly Gly Tyr Cys Asn Asp Lys Ala Val Cys Val Cys Arg Asn
1               5                   10                  15

<210> SEQ ID NO 221
<211> LENGTH: 14
<212> TYPE: PRT
<213> ORGANISM: Zophobas atratus

<400> SEQUENCE: 221

Arg Lys Gly Gly Tyr Cys Asn Ser Lys Ser Val Cys Val Cys
1               5                   10

<210> SEQ ID NO 222
<211> LENGTH: 16
<212> TYPE: PRT
<213> ORGANISM: Stomoxys calcitrans

<400> SEQUENCE: 222

Lys Ser Gly Gly Arg Cys Asn Asp Asp Ala Val Cys Val Cys Arg Lys
1               5                   10                  15

<210> SEQ ID NO 223
<211> LENGTH: 18
<212> TYPE: PRT
<213> ORGANISM: Androctonus australis

<400> SEQUENCE: 223

Arg Arg Gly Gly Tyr Cys Ala Gly Leu Phe Lys Gln Thr Cys Thr Cys
1               5                   10                  15

Tyr Arg

<210> SEQ ID NO 224
<211> LENGTH: 19
<212> TYPE: PRT
<213> ORGANISM: Leiurus quinquestriatus hebraeus

<400> SEQUENCE: 224

Arg Arg Gly Gly Tyr Cys Ala Gly Phe Phe Lys Gln Thr Cys Thr Cys
1               5                   10                  15

Tyr Arg Asn

<210> SEQ ID NO 225
<211> LENGTH: 18
<212> TYPE: PRT
<213> ORGANISM: Aeshna cyanea

<400> SEQUENCE: 225

Arg Ser Gly Gly Tyr Cys Ser Gly Pro Leu Lys Leu Thr Cys Thr Cys
1               5                   10                  15

Tyr Arg

<210> SEQ ID NO 226
<211> LENGTH: 15
<212> TYPE: PRT
<213> ORGANISM: Mytilus edulis

<400> SEQUENCE: 226

Arg Tyr Gly Gly Tyr Cys Gly Gly His Arg Leu Arg Cys Thr Cys
1               5                   10                  15

<210> SEQ ID NO 227
<211> LENGTH: 20
<212> TYPE: PRT
<213> ORGANISM: Mytilus galloprovincialis

<400> SEQUENCE: 227

Arg Cys Gly Gly Tyr Cys Gly Gly Trp His Arg Leu Arg Cys Thr Cys
1               5                   10                  15

Tyr Arg Cys Gly
            20

<210> SEQ ID NO 228
<211> LENGTH: 16
<212> TYPE: PRT
<213> ORGANISM: Mytilus edulis

<400> SEQUENCE: 228

Arg Gly Gly Tyr Cys Gly Gly His Arg Leu Arg Cys Thr Cys Tyr Arg
1               5                   10                  15

<210> SEQ ID NO 229
<211> LENGTH: 18
<212> TYPE: PRT
<213> ORGANISM: Heliothis virescens

<400> SEQUENCE: 229

Tyr Lys Gly Gly His Cys Gly Ser Phe Ala Asn Val Asn Cys Trp Cys
1               5                   10                  15

Glu Gly

<210> SEQ ID NO 230
<211> LENGTH: 18
<212> TYPE: PRT
<213> ORGANISM: Brassica napus

<400> SEQUENCE: 230

Gly Thr Val Gly Ser Cys Ala Glu Glu Lys Gly Phe Cys Asn Cys Ala
1               5                   10                  15

Cys Lys

<210> SEQ ID NO 231
<211> LENGTH: 16
<212> TYPE: PRT
<213> ORGANISM: Bombyx mori

<400> SEQUENCE: 231

Ala Ala Ser Gly Gln Cys Asn Pro Val Cys Val Glu Gly Cys Ala Cys
1               5                   10                  15

<210> SEQ ID NO 232
<211> LENGTH: 18
<212> TYPE: PRT
<213> ORGANISM: Sus sp.

<400> SEQUENCE: 232

Arg Gly Val Cys Val Cys Phe Arg Arg Arg Cys Tyr Cys Leu Gly Gly
1               5                   10                  15

Gly Arg

<210> SEQ ID NO 233
<211> LENGTH: 18
<212> TYPE: PRT
<213> ORGANISM: Sus sp.

<400> SEQUENCE: 233

Arg Gly Val Cys Val Cys Phe Arg Pro Arg Cys Tyr Cys Leu Arg Gly
1               5                   10                  15

Gly Arg

<210> SEQ ID NO 234
<211> LENGTH: 18
<212> TYPE: PRT
<213> ORGANISM: Sus sp.

<400> SEQUENCE: 234

Arg Gly Val Cys Phe Cys Ile Trp Gly Arg Cys Tyr Cys Leu Arg Gly
1               5                   10                  15

Gly Arg

<210> SEQ ID NO 235
<211> LENGTH: 17
<212> TYPE: PRT
<213> ORGANISM: Sus sp.

<400> SEQUENCE: 235

Gly Val Cys Ile Cys Phe Arg Arg Arg Cys Tyr Cys Leu Arg Gly Gly
1               5                   10                  15

Arg

<210> SEQ ID NO 236
<211> LENGTH: 18
<212> TYPE: PRT
<213> ORGANISM: Sus sp.

<400> SEQUENCE: 236

Arg Gly Val Cys Val Cys Phe Arg Arg Arg Cys Tyr Cys Leu Arg Gly
1               5                   10                  15

Gly Arg

<210> SEQ ID NO 237
<211> LENGTH: 18
<212> TYPE: PRT
<213> ORGANISM: Acanthoscurria gomesiana

<400> SEQUENCE: 237

Arg Gly Arg Cys Tyr Thr Val Cys Arg Gln Lys Tyr Cys Leu Arg Arg
1               5                   10                  15

Cys Gln

<210> SEQ ID NO 238
<211> LENGTH: 15
<212> TYPE: PRT
<213> ORGANISM: Rana sp.

<400> SEQUENCE: 238

Lys Gln Gly Ala Cys Tyr Ala Ala Cys Lys Ala Ser Lys Gln Cys
1               5                   10                  15

<210> SEQ ID NO 239
<211> LENGTH: 22

```
<212> TYPE: PRT
<213> ORGANISM: Artificial Sequence
<220> FEATURE:
<223> OTHER INFORMATION: Synthetic peptide
      consensus peptide
<220> FEATURE:
<221> NAME/KEY: MOD_RES
<222> LOCATION: (1)..(3)
<223> OTHER INFORMATION: variable amino acid
<220> FEATURE:
<221> NAME/KEY: MOD_RES
<222> LOCATION: (5)..(5)
<223> OTHER INFORMATION: variable amino acid
<220> FEATURE:
<221> NAME/KEY: MOD_RES
<222> LOCATION: (7)..(14)
<223> OTHER INFORMATION: variable amino acid
<220> FEATURE:
<221> NAME/KEY: MOD_RES
<222> LOCATION: (16)..(22)
<223> OTHER INFORMATION: variable amino acid

<400> SEQUENCE: 239

Xaa Xaa Xaa Gly Xaa Cys Xaa Xaa Xaa Xaa Xaa Xaa Xaa Cys Xaa
1               5                   10                  15

Xaa Xaa Xaa Xaa Xaa Xaa
            20

<210> SEQ ID NO 240
<211> LENGTH: 13
<212> TYPE: PRT
<213> ORGANISM: Androctonus australis

<400> SEQUENCE: 240

Arg Arg Arg Gly Gly Cys Tyr Tyr Arg Cys Thr Asn Arg
1               5                   10

<210> SEQ ID NO 241
<211> LENGTH: 10
<212> TYPE: PRT
<213> ORGANISM: Leuconostoc gelidum
<220> FEATURE:
<221> NAME/KEY: MOD_RES
<222> LOCATION: (2)..(2)
<223> OTHER INFORMATION: variable amino acid

<400> SEQUENCE: 241

Gly Xaa Cys Thr Lys Ser Gly Cys Ser Val
1               5                   10

<210> SEQ ID NO 242
<211> LENGTH: 14
<212> TYPE: PRT
<213> ORGANISM: Pseudacanthotermes spiniger

<400> SEQUENCE: 242

Arg Arg Ala Phe Cys Asp Arg Ser Gln Cys Lys Cys Val Phe
1               5                   10

<210> SEQ ID NO 243
<211> LENGTH: 22
<212> TYPE: PRT
<213> ORGANISM: Artificial Sequence
<220> FEATURE:
<223> OTHER INFORMATION: Synthetic peptide
      consensus peptide
<220> FEATURE:
<221> NAME/KEY: MOD_RES
<222> LOCATION: (1)..(3)
<223> OTHER INFORMATION: variable amino acid
<220> FEATURE:
```

```
<221> NAME/KEY: MOD_RES
<222> LOCATION: (5)..(5)
<223> OTHER INFORMATION: variable amino acid
<220> FEATURE:
<221> NAME/KEY: MOD_RES
<222> LOCATION: (7)..(14)
<223> OTHER INFORMATION: variable amino acid
<220> FEATURE:
<221> NAME/KEY: MOD_RES
<222> LOCATION: (16)..(22)
<223> OTHER INFORMATION: variable amino acid

<400> SEQUENCE: 243

Xaa Xaa Xaa Cys Xaa Gly Xaa Xaa Xaa Xaa Xaa Xaa Xaa Cys Xaa
1               5                   10                  15

Xaa Xaa Xaa Xaa Xaa Xaa
            20

<210> SEQ ID NO 244
<211> LENGTH: 21
<212> TYPE: PRT
<213> ORGANISM: Mytilus edulis

<400> SEQUENCE: 244

Arg Arg Cys Lys Gly Trp Ala Ser Ala Ser Phe Arg Gly Arg Cys Tyr
1               5                   10                  15

Cys Lys Cys Phe Arg
            20

<210> SEQ ID NO 245
<211> LENGTH: 17
<212> TYPE: PRT
<213> ORGANISM: Tachypleus tridentatus

<400> SEQUENCE: 245

Arg Gln Cys Arg Gly Tyr Thr Ser Gly Pro Phe Tyr Ser Arg Cys Thr
1               5                   10                  15

Leu

<210> SEQ ID NO 246
<211> LENGTH: 17
<212> TYPE: PRT
<213> ORGANISM: Phytolacca americana

<400> SEQUENCE: 246

Arg Asn Lys Cys Val Gly Tyr Ser Gln Gly Ala Ile Gln Phe Cys Tyr
1               5                   10                  15

Ser

<210> SEQ ID NO 247
<211> LENGTH: 12
<212> TYPE: PRT
<213> ORGANISM: Aspergillus giganteus

<400> SEQUENCE: 247

Cys Tyr Cys Lys Gly Lys Tyr Ser Asp Phe Glu Cys
1               5                   10

<210> SEQ ID NO 248
<211> LENGTH: 13
<212> TYPE: PRT
<213> ORGANISM: Podisus maculiventris

<400> SEQUENCE: 248

Met Arg Gln Cys Lys Gly Thr Arg Arg Asn Cys Tyr Ile
```

```
1               5                    10
```

<210> SEQ ID NO 249
<211> LENGTH: 13
<212> TYPE: PRT
<213> ORGANISM: Macaca mulatta

<400> SEQUENCE: 249

```
Ile Cys Arg Cys Val Gly Arg Arg Cys Leu Cys Arg Cys
1               5                   10
```

<210> SEQ ID NO 250
<211> LENGTH: 10
<212> TYPE: PRT
<213> ORGANISM: Amaranthus caudatus

<400> SEQUENCE: 250

```
Gly Cys Tyr Gly Phe Gln Ser Cys Cys Met
1               5                   10
```

<210> SEQ ID NO 251
<211> LENGTH: 15
<212> TYPE: PRT
<213> ORGANISM: Tachypleus tridentatus

<400> SEQUENCE: 251

```
Arg Arg Tyr Cys Ile Gly Arg Tyr Cys Val Arg Phe Cys Trp Lys
1               5                   10                  15
```

<210> SEQ ID NO 252
<211> LENGTH: 15
<212> TYPE: PRT
<213> ORGANISM: Tachypleus tridentatus

<400> SEQUENCE: 252

```
Arg Arg Tyr Cys Ile Gly Arg Tyr Cys Val Arg Phe Cys Trp Lys
1               5                   10                  15
```

<210> SEQ ID NO 253
<211> LENGTH: 15
<212> TYPE: PRT
<213> ORGANISM: Tachypleus gigas

<400> SEQUENCE: 253

```
Arg Arg Tyr Cys Ile Gly Arg Tyr Cys Val Arg Phe Cys Trp Lys
1               5                   10                  15
```

<210> SEQ ID NO 254
<211> LENGTH: 16
<212> TYPE: PRT
<213> ORGANISM: Limulus polyphemus

<400> SEQUENCE: 254

```
Arg Arg Tyr Cys Phe Gly Arg Tyr Cys Val Arg Phe Cys Trp Lys Lys
1               5                   10                  15
```

<210> SEQ ID NO 255
<211> LENGTH: 16
<212> TYPE: PRT
<213> ORGANISM: Limulus polyphemus

<400> SEQUENCE: 255

```
Arg Arg Tyr Cys Phe Gly Arg Tyr Cys Val Arg Phe Cys Trp Lys Lys
1               5                   10                  15
```

```
<210> SEQ ID NO 256
<211> LENGTH: 65
<212> TYPE: PRT
<213> ORGANISM: Centruroides exilicauda

<400> SEQUENCE: 256

Lys Glu Gly Tyr Leu Val Lys Ser Asp Gly Cys Lys Tyr Gly Cys
1               5                   10                  15

Leu Lys Leu Gly Glu Asn Glu Gly Cys Asp Thr Glu Cys Lys Ala Lys
            20                  25                  30

Asn Gln Gly Gly Ser Tyr Gly Tyr Cys Tyr Ala Phe Ala Cys Trp Cys
            35                  40                  45

Glu Gly Leu Pro Glu Ser Thr Pro Thr Tyr Pro Leu Pro Asn Lys Ser
    50                  55                  60

Cys
65

<210> SEQ ID NO 257
<211> LENGTH: 77
<212> TYPE: PRT
<213> ORGANISM: Hottentotta judaicus

<400> SEQUENCE: 257

Met Lys Lys Asn Gly Tyr Pro Leu Asp Arg Asn Gly Lys Thr Thr Glu
1               5                   10                  15

Cys Ser Gly Val Asn Ala Ile Ala Pro His Tyr Cys Asn Ser Glu Cys
            20                  25                  30

Thr Lys Val Tyr Tyr Ala Glu Ser Gly Tyr Cys Cys Trp Gly Ala Cys
            35                  40                  45

Tyr Cys Phe Gly Leu Glu Asp Asp Lys Pro Ile Gly Pro Met Lys Asp
    50                  55                  60

Ile Thr Lys Lys Tyr Cys Asp Val Gln Ile Ile Pro Ser
65                  70                  75

<210> SEQ ID NO 258
<211> LENGTH: 64
<212> TYPE: PRT
<213> ORGANISM: Mesobuthus martensii

<400> SEQUENCE: 258

Val Arg Asp Ala Tyr Ile Ala Lys Pro Glu Asn Cys Val Tyr His Cys
1               5                   10                  15

Ala Gly Asn Glu Gly Cys Asn Lys Leu Cys Thr Asp Asn Gly Ala Glu
            20                  25                  30

Ser Gly Tyr Cys Gln Trp Gly Gly Arg Tyr Gly Asn Ala Cys Trp Cys
            35                  40                  45

Ile Lys Leu Pro Asp Asp Val Pro Ile Arg Val Pro Gly Lys Cys His
    50                  55                  60

<210> SEQ ID NO 259
<211> LENGTH: 34
<212> TYPE: PRT
<213> ORGANISM: Heterometrus spinifer

<400> SEQUENCE: 259

Ala Ser Cys Arg Thr Pro Lys Asp Cys Ala Asp Pro Cys Arg Lys Glu
1               5                   10                  15

Thr Gly Cys Pro Tyr Gly Lys Cys Met Asn Arg Lys Cys Lys Cys Asn
            20                  25                  30

Arg Cys
```

<210> SEQ ID NO 260
<211> LENGTH: 63
<212> TYPE: PRT
<213> ORGANISM: Centruroides exilicauda

<400> SEQUENCE: 260

Lys Lys Asp Gly Tyr Pro Val Asp Ser Gly Asn Cys Lys Tyr Glu Cys
1               5                   10                  15

Leu Lys Asp Asp Tyr Cys Asn Asp Leu Cys Leu Glu Arg Lys Ala Asp
            20                  25                  30

Lys Gly Tyr Cys Tyr Trp Gly Lys Val Ser Cys Tyr Cys Tyr Gly Leu
        35                  40                  45

Pro Asp Asn Ser Pro Thr Lys Thr Ser Gly Lys Cys Asn Pro Ala
    50                  55                  60

<210> SEQ ID NO 261
<211> LENGTH: 84
<212> TYPE: PRT
<213> ORGANISM: Mesobuthus martensii

<400> SEQUENCE: 261

Met Asn Tyr Leu Val Met Ile Ser Phe Ala Leu Leu Leu Met Thr Gly
1               5                   10                  15

Val Glu Ser Val Arg Asp Ala Tyr Ile Ala Lys Pro His Asn Cys Val
            20                  25                  30

Tyr Glu Cys Ala Arg Asn Glu Tyr Cys Asn Asp Leu Cys Thr Lys Asn
        35                  40                  45

Gly Ala Lys Ser Gly Tyr Cys Gln Trp Val Gly Lys Tyr Gly Asn Gly
    50                  55                  60

Cys Trp Cys Ile Glu Leu Pro Asp Asn Val Pro Ile Arg Val Pro Gly
65                  70                  75                  80

Lys Cys His Arg

<210> SEQ ID NO 262
<211> LENGTH: 37
<212> TYPE: PRT
<213> ORGANISM: Tityus serrulatus

<400> SEQUENCE: 262

Val Phe Ile Asn Ala Lys Cys Arg Gly Ser Pro Glu Cys Leu Pro Lys
1               5                   10                  15

Cys Lys Glu Ala Ile Gly Lys Ala Ala Gly Lys Cys Met Asn Gly Lys
            20                  25                  30

Cys Lys Cys Tyr Pro
        35

<210> SEQ ID NO 263
<211> LENGTH: 37
<212> TYPE: PRT
<213> ORGANISM: Leiurus quinquestriatus hebraeus
<220> FEATURE:
<221> NAME/KEY: MOD_RES
<222> LOCATION: (1)..(1)
<223> OTHER INFORMATION: variable amino acid

<400> SEQUENCE: 263

Xaa Phe Thr Gln Glu Ser Cys Thr Ala Ser Asn Gln Cys Trp Ser Ile
1               5                   10                  15

Cys Lys Arg Leu His Asn Thr Asn Arg Gly Lys Cys Met Asn Lys Lys
            20                  25                  30

Cys Arg Cys Tyr Ser
        35

<210> SEQ ID NO 264
<211> LENGTH: 68
<212> TYPE: PRT
<213> ORGANISM: Leiurus quinquestriatus hebraeus
<220> FEATURE:
<221> NAME/KEY: MOD_RES
<222> LOCATION: (68)..(68)
<223> OTHER INFORMATION: variable amino acid

<400> SEQUENCE: 264

Val Arg Asp Gly Tyr Ile Ala Gln Pro Glu Asn Cys Val Tyr His Cys
1               5                   10                  15

Phe Pro Gly Ser Ser Gly Cys Asp Thr Leu Cys Lys Glu Lys Gly Gly
            20                  25                  30

Thr Ser Gly His Cys Gly Phe Lys Val Gly His Gly Leu Ala Cys Trp
        35                  40                  45

Cys Asn Ala Leu Pro Asp Asn Val Gly Ile Ile Val Glu Gly Glu Lys
    50                  55                  60

Cys His Ser Xaa
65

<210> SEQ ID NO 265
<211> LENGTH: 38
<212> TYPE: PRT
<213> ORGANISM: Androctonus mauretanicus mauretanicus

<400> SEQUENCE: 265

Gly Val Glu Ile Asn Val Lys Cys Ser Gly Ser Pro Gln Cys Leu Lys
1               5                   10                  15

Pro Cys Lys Asp Ala Gly Met Arg Phe Gly Lys Cys Met Asn Arg Lys
            20                  25                  30

Cys His Cys Thr Pro Lys
        35

<210> SEQ ID NO 266
<211> LENGTH: 37
<212> TYPE: PRT
<213> ORGANISM: Mesobuthus martensii
<220> FEATURE:
<221> NAME/KEY: MOD_RES
<222> LOCATION: (1)..(1)
<223> OTHER INFORMATION: variable amino acid

<400> SEQUENCE: 266

Xaa Phe Thr Asn Val Ser Cys Ser Ala Ser Ser Gln Cys Trp Pro Val
1               5                   10                  15

Cys Lys Lys Leu Phe Gly Thr Tyr Arg Gly Lys Cys Met Asn Ser Lys
            20                  25                  30

Cys Arg Cys Tyr Ser
        35

<210> SEQ ID NO 267
<211> LENGTH: 35
<212> TYPE: PRT
<213> ORGANISM: Tityus serrulatus

<400> SEQUENCE: 267

Val Val Ile Gly Gln Arg Cys Tyr Arg Ser Pro Asp Cys Tyr Ser Ala
1               5                   10                  15

Cys Lys Lys Leu Val Gly Lys Ala Thr Gly Lys Cys Thr Asn Gly Arg
                20                  25                  30

Cys Asp Cys
        35

<210> SEQ ID NO 268
<211> LENGTH: 37
<212> TYPE: PRT
<213> ORGANISM: Leiurus quinquestriatus hebraeus
<220> FEATURE:
<221> NAME/KEY: MOD_RES
<222> LOCATION: (1)..(1)
<223> OTHER INFORMATION: variable amino acid

<400> SEQUENCE: 268

Xaa Phe Thr Asn Val Ser Cys Thr Thr Ser Lys Glu Cys Trp Ser Val
1               5                   10                  15

Cys Gln Arg Leu His Asn Thr Ser Arg Gly Lys Cys Met Asn Lys Lys
                20                  25                  30

Cys Arg Cys Tyr Ser
        35

<210> SEQ ID NO 269
<211> LENGTH: 67
<212> TYPE: PRT
<213> ORGANISM: Leiurus quinquestriatus hebraeus

<400> SEQUENCE: 269

Val Arg Asp Gly Tyr Ile Ala Gln Pro Glu Asn Cys Val Tyr His Cys
1               5                   10                  15

Phe Pro Gly Ser Ser Gly Cys Asp Thr Leu Cys Lys Glu Lys Gly Gly
                20                  25                  30

Thr Ser Gly His Cys Gly Phe Lys Val Gly His Gly Leu Ala Cys Trp
        35                  40                  45

Cys Asn Ala Leu Pro Asp Asn Val Gly Ile Ile Val Glu Gly Glu Lys
    50                  55                  60

Cys His Ser
65

<210> SEQ ID NO 270
<211> LENGTH: 64
<212> TYPE: PRT
<213> ORGANISM: Androctonus australis

<400> SEQUENCE: 270

Val Lys Asp Gly Tyr Ile Val Asp Asp Val Asn Cys Thr Tyr Phe Cys
1               5                   10                  15

Gly Arg Asn Ala Tyr Cys Asn Glu Glu Cys Thr Lys Leu Lys Gly Glu
                20                  25                  30

Ser Gly Tyr Cys Gln Trp Ala Ser Pro Tyr Gly Asn Ala Cys Tyr Cys
        35                  40                  45

Tyr Lys Leu Pro Asp His Val Arg Thr Lys Gly Pro Gly Arg Cys His
    50                  55                  60

<210> SEQ ID NO 271
<211> LENGTH: 38
<212> TYPE: PRT
<213> ORGANISM: Leiurus quinquestriatus hebraeus

<400> SEQUENCE: 271

Gly Val Pro Ile Asn Val Ser Cys Thr Gly Ser Pro Gln Cys Ile Lys
1               5                   10                  15

```
Pro Cys Lys Asp Ala Gly Met Arg Phe Gly Lys Cys Met Asn Arg Lys
             20                  25                  30
Cys His Cys Thr Pro Lys
         35

<210> SEQ ID NO 272
<211> LENGTH: 64
<212> TYPE: PRT
<213> ORGANISM: Mesobuthus martensii

<400> SEQUENCE: 272

Gly Arg Asp Ala Tyr Ile Ala Asp Ser Glu Asn Cys Thr Tyr Phe Cys
1               5                   10                  15

Gly Ser Asn Pro Tyr Cys Asn Asp Val Cys Thr Glu Asn Gly Ala Lys
             20                  25                  30

Ser Gly Tyr Cys Gln Trp Ala Gly Arg Tyr Gly Asn Ala Cys Tyr Cys
         35                  40                  45

Ile Asp Leu Pro Ala Ser Glu Arg Ile Lys Glu Gly Gly Arg Cys Gly
     50                  55                  60

<210> SEQ ID NO 273
<211> LENGTH: 57
<212> TYPE: PRT
<213> ORGANISM: Mesobuthus eupeus

<400> SEQUENCE: 273

Met Lys Ile Ser Phe Val Leu Leu Thr Leu Phe Ile Cys Ser Ile
1               5                   10                  15

Gly Trp Ser Glu Ala Arg Pro Thr Asp Ile Lys Cys Ser Glu Ser Tyr
             20                  25                  30

Gln Cys Phe Pro Val Cys Lys Ser Arg Phe Gly Lys Thr Asn Gly Arg
         35                  40                  45

Cys Val Asn Gly Phe Cys Asp Cys Phe
     50                  55

<210> SEQ ID NO 274
<211> LENGTH: 35
<212> TYPE: PRT
<213> ORGANISM: Pandinus imperator

<400> SEQUENCE: 274

Thr Ile Ser Cys Thr Asn Pro Lys Gln Cys Tyr Pro His Cys Lys Lys
1               5                   10                  15

Glu Thr Gly Tyr Pro Asn Ala Lys Cys Met Asn Arg Lys Cys Lys Cys
             20                  25                  30

Phe Gly Arg
         35

<210> SEQ ID NO 275
<211> LENGTH: 59
<212> TYPE: PRT
<213> ORGANISM: Centruroides sculpturatus

<400> SEQUENCE: 275

Lys Asp Gly Tyr Pro Val Asp Ser Lys Gly Cys Lys Leu Ser Cys Val
1               5                   10                  15

Ala Asn Asn Tyr Cys Asp Asn Gln Cys Lys Met Lys Lys Ala Ser Gly
             20                  25                  30

Gly His Cys Tyr Ala Met Ser Cys Tyr Cys Glu Gly Leu Pro Glu Asn
         35                  40                  45
```

```
Ala Lys Val Ser Asp Ser Ala Thr Asn Ile Cys
    50                  55

<210> SEQ ID NO 276
<211> LENGTH: 86
<212> TYPE: PRT
<213> ORGANISM: Centruroides sculpturatus

<400> SEQUENCE: 276

Met Asn Ser Leu Leu Met Ile Thr Ala Cys Leu Val Leu Ile Gly Thr
1               5                   10                  15

Val Trp Ala Lys Asp Gly Tyr Leu Val Glu Lys Thr Gly Cys Lys Lys
            20                  25                  30

Thr Cys Tyr Lys Leu Gly Glu Asn Asp Phe Cys Asn Arg Glu Cys Lys
        35                  40                  45

Trp Lys His Ile Gly Gly Ser Tyr Gly Tyr Cys Tyr Gly Phe Gly Cys
    50                  55                  60

Tyr Cys Glu Gly Leu Pro Asp Ser Thr Gln Thr Trp Pro Leu Pro Asn
65                  70                  75                  80

Lys Thr Cys Gly Lys Lys
                85

<210> SEQ ID NO 277
<211> LENGTH: 78
<212> TYPE: PRT
<213> ORGANISM: Conus textile

<400> SEQUENCE: 277

Met Lys Leu Thr Cys Met Met Ile Val Ala Val Leu Phe Leu Thr Ala
1               5                   10                  15

Trp Thr Phe Ala Thr Ala Asp Asp Pro Arg Asn Gly Leu Gly Asn Leu
            20                  25                  30

Phe Ser Asn Ala His His Glu Met Lys Asn Pro Glu Ala Ser Lys Leu
        35                  40                  45

Asn Lys Arg Trp Cys Lys Gln Ser Gly Glu Met Cys Asn Leu Leu Asp
    50                  55                  60

Gln Asn Cys Cys Asp Gly Tyr Cys Ile Val Leu Val Cys Thr
65                  70                  75

<210> SEQ ID NO 278
<211> LENGTH: 49
<212> TYPE: PRT
<213> ORGANISM: Anthopleura xanthogrammica

<400> SEQUENCE: 278

Gly Val Pro Cys Leu Cys Asp Ser Asp Gly Pro Arg Pro Arg Gly Asn
1               5                   10                  15

Thr Leu Ser Gly Ile Leu Trp Phe Tyr Pro Ser Gly Cys Pro Ser Gly
            20                  25                  30

Trp His Asn Cys Lys Ala His Gly Pro Asn Ile Gly Trp Cys Cys Lys
        35                  40                  45

Lys

<210> SEQ ID NO 279
<211> LENGTH: 84
<212> TYPE: PRT
<213> ORGANISM: Tityus serrulatus

<400> SEQUENCE: 279
```

```
Met Lys Gly Met Ile Leu Phe Ile Ser Cys Leu Leu Leu Ile Gly Ile
1               5                   10                  15

Val Val Glu Cys Lys Glu Gly Tyr Leu Met Asp His Glu Gly Cys Lys
            20                  25                  30

Leu Ser Cys Phe Ile Arg Pro Ser Gly Tyr Cys Gly Arg Glu Cys Gly
        35                  40                  45

Ile Lys Lys Gly Ser Ser Gly Tyr Cys Ala Trp Pro Ala Cys Tyr Cys
    50                  55                  60

Tyr Gly Leu Pro Asn Trp Val Lys Val Trp Asp Arg Ala Thr Asn Lys
65                  70                  75                  80

Cys Gly Lys Lys

<210> SEQ ID NO 280
<211> LENGTH: 38
<212> TYPE: PRT
<213> ORGANISM: Hadronyche infensa

<400> SEQUENCE: 280

Lys Cys Leu Ala Glu Ala Ala Asp Cys Ser Pro Trp Ser Gly Asp Ser
1               5                   10                  15

Cys Cys Lys Pro Tyr Leu Cys Ser Cys Ile Phe Phe Tyr Pro Cys Ser
            20                  25                  30

Cys Arg Pro Lys Gly Trp
        35

<210> SEQ ID NO 281
<211> LENGTH: 35
<212> TYPE: PRT
<213> ORGANISM: Ornithoctonus huwena

<400> SEQUENCE: 281

Glu Cys Leu Glu Ile Phe Lys Ala Cys Asn Pro Ser Asn Asp Gln Cys
1               5                   10                  15

Cys Lys Ser Ser Lys Leu Val Cys Ser Arg Lys Thr Arg Trp Cys Lys
            20                  25                  30

Tyr Gln Ile
        35

<210> SEQ ID NO 282
<211> LENGTH: 66
<212> TYPE: PRT
<213> ORGANISM: Mesobuthus martensii

<400> SEQUENCE: 282

Val Arg Asp Gly Tyr Ile Ala Leu Pro His Asn Cys Ala Tyr Gly Cys
1               5                   10                  15

Leu Asn Asn Glu Tyr Cys Asn Asn Leu Cys Thr Lys Asp Gly Ala Lys
            20                  25                  30

Ile Gly Tyr Cys Asn Ile Val Gly Lys Tyr Gly Asn Ala Cys Trp Cys
        35                  40                  45

Ile Gln Leu Pro Asp Asn Val Pro Ile Arg Val Pro Gly Arg Cys His
    50                  55                  60

Pro Ala
65

<210> SEQ ID NO 283
<211> LENGTH: 38
<212> TYPE: PRT
<213> ORGANISM: Mesobuthus martensii
```

-continued

```
<400> SEQUENCE: 283

Ile Glu Ala Ile Arg Cys Gly Gly Ser Arg Asp Cys Tyr Arg Pro Cys
1               5                   10                  15

Gln Lys Arg Thr Gly Cys Pro Asn Ala Lys Cys Ile Asn Lys Thr Cys
                20                  25                  30

Lys Cys Tyr Gly Cys Ser
            35

<210> SEQ ID NO 284
<211> LENGTH: 42
<212> TYPE: PRT
<213> ORGANISM: Centruroides noxius

<400> SEQUENCE: 284

Asp Arg Asp Ser Cys Val Asp Lys Ser Arg Cys Ala Lys Tyr Gly Tyr
1               5                   10                  15

Tyr Gln Glu Cys Gln Asp Cys Cys Lys Asn Ala Gly His Asn Gly Gly
                20                  25                  30

Thr Cys Met Phe Phe Lys Cys Lys Cys Ala
            35                  40

<210> SEQ ID NO 285
<211> LENGTH: 36
<212> TYPE: PRT
<213> ORGANISM: Grammostola rosea

<400> SEQUENCE: 285

Asp Cys Val Arg Phe Trp Gly Lys Cys Ser Gln Thr Ser Asp Cys Cys
1               5                   10                  15

Pro His Leu Ala Cys Lys Ser Lys Trp Pro Arg Asn Ile Cys Val Trp
                20                  25                  30

Asp Gly Ser Val
            35

<210> SEQ ID NO 286
<211> LENGTH: 40
<212> TYPE: PRT
<213> ORGANISM: Tityus serrulatus

<400> SEQUENCE: 286

Trp Cys Ser Thr Cys Leu Asp Leu Ala Cys Gly Ala Ser Arg Glu Cys
1               5                   10                  15

Tyr Asp Pro Cys Phe Lys Ala Phe Gly Arg Ala His Gly Lys Cys Met
                20                  25                  30

Asn Asn Lys Cys Arg Cys Tyr Thr
            35                  40

<210> SEQ ID NO 287
<211> LENGTH: 35
<212> TYPE: PRT
<213> ORGANISM: Pandinus imperator

<400> SEQUENCE: 287

Thr Ile Ser Cys Thr Asn Pro Lys Gln Cys Tyr Pro His Cys Lys Lys
1               5                   10                  15

Glu Thr Gly Tyr Pro Asn Ala Lys Cys Met Asn Arg Lys Cys Lys Cys
                20                  25                  30

Phe Gly Arg
        35
```

-continued

<210> SEQ ID NO 288
<211> LENGTH: 39
<212> TYPE: PRT
<213> ORGANISM: Centruroides limbatus

<400> SEQUENCE: 288

Thr Val Ile Asp Val Lys Cys Thr Ser Pro Lys Gln Cys Leu Pro Pro
1               5                   10                  15

Cys Lys Ala Gln Phe Gly Ile Arg Ala Gly Ala Lys Cys Met Asn Gly
            20                  25                  30

Lys Cys Lys Cys Tyr Pro His
        35

<210> SEQ ID NO 289
<211> LENGTH: 31
<212> TYPE: PRT
<213> ORGANISM: Mesobuthus martensii

<400> SEQUENCE: 289

Ala Ala Cys Tyr Ser Ser Asp Cys Arg Val Lys Cys Val Ala Met Gly
1               5                   10                  15

Phe Ser Ser Gly Lys Cys Ile Asn Ser Lys Cys Lys Cys Tyr Lys
            20                  25                  30

<210> SEQ ID NO 290
<211> LENGTH: 37
<212> TYPE: PRT
<213> ORGANISM: Mesobuthus martensii
<220> FEATURE:
<221> NAME/KEY: MOD_RES
<222> LOCATION: (1)..(1)
<223> OTHER INFORMATION: variable amino acid

<400> SEQUENCE: 290

Xaa Phe Thr Asp Val Lys Cys Thr Gly Ser Lys Gln Cys Trp Pro Val
1               5                   10                  15

Cys Lys Gln Met Phe Gly Lys Pro Asn Gly Lys Cys Met Asn Gly Lys
            20                  25                  30

Cys Arg Cys Tyr Ser
        35

<210> SEQ ID NO 291
<211> LENGTH: 68
<212> TYPE: PRT
<213> ORGANISM: Arabidopsis thaliana
<220> FEATURE:
<221> NAME/KEY: MOD_RES
<222> LOCATION: (1)..(1)
<223> OTHER INFORMATION: variable amino acid

<400> SEQUENCE: 291

Xaa Pro Glu Ile Glu Ala Gln Gly Asn Glu Cys Leu Lys Glu Tyr Gly
1               5                   10                  15

Gly Asp Val Gly Phe Gly Phe Cys Ala Pro Arg Ile Phe Pro Thr Ile
            20                  25                  30

Cys Tyr Thr Arg Cys Arg Glu Asn Lys Gly Ala Lys Gly Gly Arg Cys
        35                  40                  45

Arg Trp Gly Gln Gly Ser Asn Val Lys Cys Leu Cys Asp Phe Cys Gly
    50                  55                  60

Asp Thr Pro Gln
65

<210> SEQ ID NO 292

```
<211> LENGTH: 29
<212> TYPE: PRT
<213> ORGANISM: Cucurbita maxima

<400> SEQUENCE: 292

Arg Val Cys Pro Arg Ile Leu Leu Glu Cys Lys Lys Asp Ser Asp Cys
1               5                   10                  15

Leu Ala Glu Cys Val Cys Leu Glu His Gly Tyr Cys Gly
            20                  25

<210> SEQ ID NO 293
<211> LENGTH: 55
<212> TYPE: PRT
<213> ORGANISM: Halocynthia roretzi

<400> SEQUENCE: 293

Ala His Met Asp Cys Thr Glu Phe Asn Pro Leu Cys Arg Cys Asn Lys
1               5                   10                  15

Met Leu Gly Asp Leu Ile Cys Ala Val Ile Gly Asp Ala Lys Glu Glu
            20                  25                  30

His Arg Asn Met Cys Ala Leu Cys Cys Glu His Pro Gly Gly Phe Glu
        35                  40                  45

Tyr Ser Asn Gly Pro Cys Glu
    50                  55

<210> SEQ ID NO 294
<211> LENGTH: 32
<212> TYPE: PRT
<213> ORGANISM: Amaranthus hypochondriacus

<400> SEQUENCE: 294

Cys Ile Pro Lys Trp Asn Arg Cys Gly Pro Lys Met Asp Gly Val Pro
1               5                   10                  15

Cys Cys Glu Pro Tyr Thr Cys Thr Ser Asp Tyr Tyr Gly Asn Cys Ser
            20                  25                  30

<210> SEQ ID NO 295
<211> LENGTH: 28
<212> TYPE: PRT
<213> ORGANISM: Ecballium elaterium

<400> SEQUENCE: 295

Gly Cys Pro Arg Ile Leu Met Arg Cys Lys Gln Asp Ser Asp Cys Leu
1               5                   10                  15

Ala Gly Cys Val Cys Gly Pro Asn Gly Phe Cys Gly
            20                  25

<210> SEQ ID NO 296
<211> LENGTH: 29
<212> TYPE: PRT
<213> ORGANISM: Cucurbita maxima

<400> SEQUENCE: 296

Arg Val Cys Pro Arg Ile Leu Met Glu Cys Lys Lys Asp Ser Asp Cys
1               5                   10                  15

Leu Ala Glu Cys Val Cys Leu Glu His Gly Tyr Cys Gly
            20                  25

<210> SEQ ID NO 297
<211> LENGTH: 34
<212> TYPE: PRT
<213> ORGANISM: Momordica cochinchinensis
<220> FEATURE:
```

```
<221> NAME/KEY: MOD_RES
<222> LOCATION: (1)..(1)
<223> OTHER INFORMATION: variable amino acid

<400> SEQUENCE: 297

Xaa Gly Ser Asp Gly Gly Val Cys Pro Lys Ile Leu Lys Lys Cys Arg
1               5                   10                  15

Arg Asp Ser Asp Cys Pro Gly Ala Cys Ile Cys Arg Gly Asn Gly Tyr
                20                  25                  30

Cys Gly

<210> SEQ ID NO 298
<211> LENGTH: 50
<212> TYPE: PRT
<213> ORGANISM: Brassica rapa

<400> SEQUENCE: 298

Asn Leu Met Lys Arg Cys Thr Arg Gly Phe Arg Lys Leu Gly Lys Cys
1               5                   10                  15

Thr Thr Leu Glu Glu Glu Lys Cys Lys Thr Leu Tyr Pro Arg Gly Gln
                20                  25                  30

Cys Thr Cys Ser Asp Ser Lys Met Asn Thr His Ser Cys Asp Cys Lys
            35                  40                  45

Ser Cys
    50

<210> SEQ ID NO 299
<211> LENGTH: 37
<212> TYPE: PRT
<213> ORGANISM: Glycine max

<400> SEQUENCE: 299

Ala Asp Cys Asn Gly Ala Cys Ser Pro Phe Glu Val Pro Pro Cys Arg
1               5                   10                  15

Ser Arg Asp Cys Arg Cys Val Pro Ile Gly Leu Phe Val Gly Phe Cys
                20                  25                  30

Ile His Pro Thr Gly
            35

<210> SEQ ID NO 300
<211> LENGTH: 46
<212> TYPE: PRT
<213> ORGANISM: Helleborus purpurascens

<400> SEQUENCE: 300

Lys Ser Cys Cys Arg Asn Thr Leu Ala Arg Asn Cys Tyr Asn Ala Cys
1               5                   10                  15

Arg Phe Thr Gly Gly Ser Gln Pro Thr Cys Gly Ile Leu Cys Asp Cys
                20                  25                  30

Ile His Val Thr Thr Thr Cys Pro Ser Ser His Pro Ser
            35                  40                  45

<210> SEQ ID NO 301
<211> LENGTH: 41
<212> TYPE: PRT
<213> ORGANISM: Macrovipera lebetina obtusa
<220> FEATURE:
<221> NAME/KEY: MOD_RES
<222> LOCATION: (1)..(1)
<223> OTHER INFORMATION: variable amino acid

<400> SEQUENCE: 301
```

-continued

```
Xaa Thr Thr Gly Pro Cys Cys Arg Gln Cys Lys Leu Lys Pro Ala Gly
1               5                   10                  15

Thr Thr Cys Trp Lys Thr Ser Leu Thr Ser His Tyr Cys Thr Gly Lys
            20                  25                  30

Ser Cys Asp Cys Pro Leu Tyr Pro Gly
            35                  40
```

<210> SEQ ID NO 302
<211> LENGTH: 50
<212> TYPE: PRT
<213> ORGANISM: Homo sapiens

<400> SEQUENCE: 302

```
Arg Lys Gly His Phe Ser Arg Cys Pro Lys Gln Tyr Lys His Tyr Cys
1               5                   10                  15

Ile Lys Gly Arg Cys Arg Phe Val Val Ala Glu Gln Thr Pro Ser Cys
            20                  25                  30

Val Cys Asp Glu Gly Tyr Ile Gly Ala Arg Cys Glu Arg Val Asp Leu
            35                  40                  45

Phe Tyr
    50
```

<210> SEQ ID NO 303
<211> LENGTH: 29
<212> TYPE: PRT
<213> ORGANISM: Oldenlandia affinis
<220> FEATURE:
<221> NAME/KEY: MOD_RES
<222> LOCATION: (1)..(1)
<223> OTHER INFORMATION: variable amino acid

<400> SEQUENCE: 303

```
Xaa Gly Leu Pro Val Cys Gly Glu Thr Cys Val Gly Thr Cys Asn
1               5                   10                  15

Thr Pro Gly Cys Thr Cys Ser Trp Pro Val Cys Thr Arg
            20                  25
```

<210> SEQ ID NO 304
<211> LENGTH: 23
<212> TYPE: PRT
<213> ORGANISM: Pseudoplusia includens
<220> FEATURE:
<221> NAME/KEY: MOD_RES
<222> LOCATION: (1)..(1)
<223> OTHER INFORMATION: variable amino acid

<400> SEQUENCE: 304

```
Xaa Asn Phe Asn Gly Gly Cys Leu Ala Gly Tyr Met Arg Thr Ala Asp
1               5                   10                  15

Gly Arg Cys Lys Pro Thr Phe
            20
```

<210> SEQ ID NO 305
<211> LENGTH: 25
<212> TYPE: PRT
<213> ORGANISM: Apanteles kariyai

<400> SEQUENCE: 305

```
Glu Asn Phe Ser Gly Gly Cys Val Ala Gly Tyr Met Arg Thr Pro Asp
1               5                   10                  15

Gly Arg Cys Lys Pro Thr Phe Tyr Gln
            20                  25
```

```
<210> SEQ ID NO 306
<211> LENGTH: 58
<212> TYPE: PRT
<213> ORGANISM: Desulfovibrio gigas

<400> SEQUENCE: 306

Pro Ile Glu Val Asn Asp Asp Cys Met Ala Cys Glu Ala Cys Val Glu
1               5                   10                  15

Ile Cys Pro Asp Val Phe Glu Met Asn Glu Glu Gly Asp Lys Ala Val
            20                  25                  30

Val Ile Asn Pro Asp Ser Asp Leu Asp Cys Val Glu Glu Ala Ile Asp
        35                  40                  45

Ser Cys Pro Ala Glu Ala Ile Val Arg Ser
    50                  55

<210> SEQ ID NO 307
<211> LENGTH: 32
<212> TYPE: PRT
<213> ORGANISM: Ornithoctonus huwena
<220> FEATURE:
<221> NAME/KEY: MOD_RES
<222> LOCATION: (1)..(1)
<223> OTHER INFORMATION: variable amino acid

<400> SEQUENCE: 307

Xaa Cys Leu Gly Asp Lys Cys Asp Tyr Asn Asn Gly Cys Cys Ser Gly
1               5                   10                  15

Tyr Val Cys Ser Arg Thr Trp Lys Trp Cys Val Leu Ala Gly Pro Trp
            20                  25                  30

<210> SEQ ID NO 308
<211> LENGTH: 55
<212> TYPE: PRT
<213> ORGANISM: Hirudo medicinalis

<400> SEQUENCE: 308

Thr Gln Gly Asn Thr Cys Gly Gly Glu Thr Cys Ser Ala Ala Gln Val
1               5                   10                  15

Cys Leu Lys Gly Lys Cys Val Cys Asn Glu Val His Cys Arg Ile Arg
            20                  25                  30

Cys Lys Tyr Gly Leu Lys Lys Asp Glu Asn Gly Cys Glu Tyr Pro Cys
        35                  40                  45

Ser Cys Ala Lys Ala Ser Gln
    50                  55

<210> SEQ ID NO 309
<211> LENGTH: 54
<212> TYPE: PRT
<213> ORGANISM: Pentadiplandra brazzeana
<220> FEATURE:
<221> NAME/KEY: MOD_RES
<222> LOCATION: (1)..(1)
<223> OTHER INFORMATION: variable amino acid

<400> SEQUENCE: 309

Xaa Asp Lys Cys Lys Lys Val Tyr Glu Asn Tyr Pro Val Ser Lys Cys
1               5                   10                  15

Gln Leu Ala Asn Gln Cys Asn Tyr Asp Cys Lys Leu Asp Lys His Ala
            20                  25                  30

Arg Ser Gly Glu Cys Phe Tyr Asp Glu Lys Arg Asn Leu Gln Cys Ile
        35                  40                  45

Cys Asp Tyr Cys Glu Tyr
    50
```

```
<210> SEQ ID NO 310
<211> LENGTH: 46
<212> TYPE: PRT
<213> ORGANISM: Crambe hispanica

<400> SEQUENCE: 310

Thr Thr Cys Cys Pro Ser Ile Val Ala Arg Ser Asn Phe Asn Val Cys
1               5                   10                  15

Arg Leu Pro Gly Thr Ser Glu Ala Ile Cys Ala Thr Tyr Thr Gly Cys
            20                  25                  30

Ile Ile Ile Pro Gly Ala Thr Cys Pro Gly Asp Tyr Ala Asn
        35                  40                  45

<210> SEQ ID NO 311
<211> LENGTH: 51
<212> TYPE: PRT
<213> ORGANISM: Hirudo medicinalis
<220> FEATURE:
<221> NAME/KEY: MOD_RES
<222> LOCATION: (1)..(1)
<223> OTHER INFORMATION: variable amino acid

<400> SEQUENCE: 311

Xaa Val Tyr Thr Asp Cys Thr Glu Ser Gly Gln Asn Leu Cys Leu Cys
1               5                   10                  15

Glu Gly Ser Asn Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
        35                  40                  45

Gln Ser His
    50

<210> SEQ ID NO 312
<211> LENGTH: 13
<212> TYPE: PRT
<213> ORGANISM: Homo sapiens

<400> SEQUENCE: 312

Thr Cys Glu Ile Cys Ala Tyr Ala Ala Cys Thr Gly Cys
1               5                   10

<210> SEQ ID NO 313
<211> LENGTH: 53
<212> TYPE: PRT
<213> ORGANISM: Mus musculus

<400> SEQUENCE: 313

Asn Ser Tyr Pro Gly Cys Pro Ser Ser Tyr Asp Gly Tyr Cys Leu Asn
1               5                   10                  15

Gly Gly Val Cys Met His Ile Glu Ser Leu Asp Ser Tyr Thr Cys Asn
            20                  25                  30

Cys Val Ile Gly Tyr Ser Gly Asp Arg Cys Gln Thr Arg Asp Leu Arg
        35                  40                  45

Trp Trp Glu Leu Arg
    50

<210> SEQ ID NO 314
<211> LENGTH: 16
<212> TYPE: PRT
<213> ORGANISM: Homo sapiens

<400> SEQUENCE: 314
```

```
Asn Asp Asp Cys Glu Leu Cys Val Asn Val Ala Cys Thr Gly Cys Leu
1               5                   10                  15
```

<210> SEQ ID NO 315
<211> LENGTH: 43
<212> TYPE: PRT
<213> ORGANISM: Hevea brasiliensis

<400> SEQUENCE: 315

```
Glu Gln Cys Gly Arg Gln Ala Gly Gly Lys Leu Cys Pro Asn Asn Leu
1               5                   10                  15

Cys Cys Ser Gln Trp Gly Trp Cys Gly Ser Thr Asp Glu Tyr Cys Ser
            20                  25                  30

Pro Asp His Asn Cys Gln Ser Asn Cys Lys Asp
        35                  40
```

<210> SEQ ID NO 316
<211> LENGTH: 70
<212> TYPE: PRT
<213> ORGANISM: Homo sapiens

<400> SEQUENCE: 316

```
Gly Ser Glu Val Ser Asp Lys Arg Thr Cys Val Ser Leu Thr Thr Gln
1               5                   10                  15

Arg Leu Pro Val Ser Arg Ile Lys Thr Tyr Thr Ile Thr Glu Gly Ser
            20                  25                  30

Leu Arg Ala Val Ile Phe Ile Thr Lys Arg Gly Leu Lys Val Cys Ala
        35                  40                  45

Asp Pro Gln Ala Thr Trp Val Arg Asp Val Val Arg Ser Met Asp Arg
    50                  55                  60

Lys Ser Asn Thr Arg Asn
65                  70
```

<210> SEQ ID NO 317
<211> LENGTH: 72
<212> TYPE: PRT
<213> ORGANISM: Homo sapiens

<400> SEQUENCE: 317

```
Ala Ser Val Ala Thr Glu Leu Arg Cys Gln Cys Leu Gln Thr Leu Gln
1               5                   10                  15

Gly Ile His Pro Lys Asn Ile Gln Ser Val Asn Val Lys Ser Pro Gly
            20                  25                  30

Pro His Cys Ala Gln Thr Glu Val Ile Ala Thr Leu Lys Asn Gly Arg
        35                  40                  45

Lys Ala Cys Leu Asn Pro Ala Ser Pro Ile Val Lys Lys Ile Ile Glu
    50                  55                  60

Lys Met Leu Asn Ser Asp Lys Ser
65                  70
```

<210> SEQ ID NO 318
<211> LENGTH: 71
<212> TYPE: PRT
<213> ORGANISM: Homo sapiens

<400> SEQUENCE: 318

```
Leu Ala Thr Glu Leu Arg Cys Gln Cys Leu Gln Thr Leu Gln Gly Ile
1               5                   10                  15

His Leu Lys Asn Ile Gln Ser Val Lys Val Lys Ser Pro Gly Pro His
            20                  25                  30
```

```
Cys Ala Gln Thr Glu Val Ile Ala Thr Leu Lys Asn Gly Gln Lys Ala
            35                  40                  45

Cys Leu Asn Pro Ala Ser Pro Met Val Lys Lys Ile Ile Glu Lys Met
50                  55                  60

Leu Lys Asn Gly Lys Ser Asn
65                  70

<210> SEQ ID NO 319
<211> LENGTH: 70
<212> TYPE: PRT
<213> ORGANISM: Homo sapiens

<400> SEQUENCE: 319

Glu Ala Glu Glu Asp Gly Asp Leu Gln Cys Leu Cys Val Lys Thr Thr
1               5                   10                  15

Ser Gln Val Arg Pro Arg His Ile Thr Ser Leu Glu Val Ile Lys Ala
            20                  25                  30

Gly Pro His Cys Pro Thr Ala Gln Leu Ile Ala Thr Leu Lys Asn Gly
        35                  40                  45

Arg Lys Ile Cys Leu Asp Leu Gln Ala Pro Leu Tyr Lys Lys Ile Ile
50                  55                  60

Lys Lys Leu Leu Glu Ser
65                  70

<210> SEQ ID NO 320
<211> LENGTH: 73
<212> TYPE: PRT
<213> ORGANISM: Homo sapiens

<400> SEQUENCE: 320

Ala Val Leu Arg Glu Leu Arg Cys Val Cys Leu Gln Thr Thr Gln Gly
1               5                   10                  15

Val His Pro Lys Met Ile Ser Asn Leu Gln Val Phe Ala Ile Gly Pro
            20                  25                  30

Gln Cys Ser Lys Val Glu Val Val Ala Ser Leu Lys Asn Gly Lys Glu
        35                  40                  45

Ile Cys Leu Asp Pro Glu Ala Pro Phe Leu Lys Lys Val Ile Gln Lys
50                  55                  60

Ile Leu Asp Gly Gly Asn Lys Glu Asn
65                  70

<210> SEQ ID NO 321
<211> LENGTH: 73
<212> TYPE: PRT
<213> ORGANISM: Homo sapiens

<400> SEQUENCE: 321

Ala Val Leu Thr Glu Leu Arg Cys Thr Cys Leu Arg Val Thr Leu Arg
1               5                   10                  15

Val Asn Pro Lys Thr Ile Gly Lys Leu Gln Val Phe Pro Ala Gly Pro
            20                  25                  30

Gln Cys Ser Lys Val Glu Val Val Ala Ser Leu Lys Asn Gly Lys Gln
        35                  40                  45

Val Cys Leu Asp Pro Glu Ala Pro Phe Leu Lys Lys Val Ile Gln Lys
50                  55                  60

Ile Leu Asp Ser Gly Asn Lys Lys Asn
65                  70
```

<210> SEQ ID NO 322
<211> LENGTH: 73
<212> TYPE: PRT
<213> ORGANISM: Homo sapiens

<400> SEQUENCE: 322

Asp Leu Tyr Ala Glu Leu Arg Cys Met Cys Ile Lys Thr Thr Ser Gly
1               5                   10                  15

Ile His Pro Lys Asn Ile Gln Ser Leu Glu Val Ile Gly Lys Gly Thr
            20                  25                  30

His Cys Asn Gln Val Glu Val Ile Ala Thr Leu Lys Asp Gly Arg Lys
        35                  40                  45

Ile Cys Leu Asp Pro Asp Ala Pro Arg Ile Lys Lys Ile Val Gln Lys
    50                  55                  60

Lys Leu Ala Gly Asp Glu Ser Ala Asp
65                  70

<210> SEQ ID NO 323
<211> LENGTH: 72
<212> TYPE: PRT
<213> ORGANISM: Homo sapiens

<400> SEQUENCE: 323

Ser Ala Lys Glu Leu Arg Cys Gln Cys Ile Lys Thr Tyr Ser Lys Pro
1               5                   10                  15

Phe His Pro Lys Phe Ile Lys Glu Leu Arg Val Ile Glu Ser Gly Pro
            20                  25                  30

His Cys Ala Asn Thr Glu Ile Ile Val Lys Leu Ser Asp Gly Arg Glu
        35                  40                  45

Leu Cys Leu Asp Pro Lys Glu Asn Trp Val Gln Arg Val Val Glu Lys
    50                  55                  60

Phe Leu Lys Arg Ala Glu Asn Ser
65                  70

<210> SEQ ID NO 324
<211> LENGTH: 72
<212> TYPE: PRT
<213> ORGANISM: Homo sapiens

<400> SEQUENCE: 324

Gly Arg Cys Ser Cys Ile Ser Thr Asn Gln Gly Thr Ile His Leu Gln
1               5                   10                  15

Ser Leu Lys Asp Leu Lys Gln Phe Ala Pro Ser Pro Ser Cys Glu Lys
            20                  25                  30

Ile Glu Ile Ile Ala Thr Leu Lys Asn Gly Val Gln Thr Cys Leu Asn
        35                  40                  45

Pro Asp Ser Ala Asp Val Lys Glu Leu Ile Lys Lys Trp Glu Lys Gln
    50                  55                  60

Val Ser Gln Lys Lys Lys Gln Lys
65                  70

<210> SEQ ID NO 325
<211> LENGTH: 71
<212> TYPE: PRT
<213> ORGANISM: Homo sapiens

<400> SEQUENCE: 325

Val Arg Cys Thr Cys Ile Ser Ile Ser Asn Gln Pro Val Asn Pro Arg
1               5                   10                  15

Ser Leu Glu Lys Leu Glu Ile Ile Pro Ala Ser Gln Phe Cys Pro Arg

-continued

```
                 20                  25                  30
Val Glu Ile Ile Ala Thr Met Lys Lys Gly Glu Lys Arg Cys Leu
             35                  40                  45

Asn Pro Glu Ser Lys Ala Ile Lys Asn Leu Leu Lys Ala Val Ser Lys
         50                  55                  60

Glu Arg Ser Lys Arg Ser Pro
 65                  70

<210> SEQ ID NO 326
<211> LENGTH: 67
<212> TYPE: PRT
<213> ORGANISM: Homo sapiens

<400> SEQUENCE: 326

Gly Arg Cys Leu Cys Ile Gly Pro Gly Val Lys Ala Val Lys Val Ala
  1               5                  10                  15

Asp Ile Glu Lys Ala Ser Ile Met Tyr Pro Ser Asn Asn Cys Asp Lys
             20                  25                  30

Ile Glu Val Ile Ile Thr Leu Lys Glu Asn Lys Gly Gln Arg Cys Leu
         35                  40                  45

Asn Pro Lys Ser Lys Gln Ala Arg Leu Ile Ile Lys Lys Val Glu Arg
     50                  55                  60

Lys Asn Phe
 65

<210> SEQ ID NO 327
<211> LENGTH: 66
<212> TYPE: PRT
<213> ORGANISM: Homo sapiens

<400> SEQUENCE: 327

Tyr Arg Cys Pro Cys Arg Phe Phe Glu Ser His Val Ala Arg Ala Asn
  1               5                  10                  15

Val Lys His Leu Lys Ile Leu Asn Thr Pro Asn Cys Ala Leu Gln Ile
             20                  25                  30

Val Ala Arg Leu Lys Asn Asn Asn Arg Gln Val Cys Ile Asp Pro Lys
         35                  40                  45

Leu Lys Trp Ile Gln Glu Tyr Leu Glu Lys Ala Leu Asn Lys Arg Phe
     50                  55                  60

Lys Met
 65

<210> SEQ ID NO 328
<211> LENGTH: 72
<212> TYPE: PRT
<213> ORGANISM: Homo sapiens

<400> SEQUENCE: 328

Leu Arg Cys Arg Cys Val Gln Glu Ser Ser Val Phe Ile Pro Arg Arg
  1               5                  10                  15

Phe Ile Asp Arg Ile Gln Ile Leu Pro Arg Gly Asn Gly Cys Pro Arg
             20                  25                  30

Lys Glu Ile Ile Val Trp Lys Lys Asn Lys Ser Ile Val Cys Val Asp
         35                  40                  45

Pro Gln Ala Glu Trp Ile Gln Arg Met Met Glu Val Leu Arg Lys Arg
     50                  55                  60

Ser Ser Ser Thr Leu Pro Val Pro
 65                  70
```

<210> SEQ ID NO 329
<211> LENGTH: 67
<212> TYPE: PRT
<213> ORGANISM: Homo sapiens

<400> SEQUENCE: 329

Phe Ser Arg Cys Cys Phe Ser Phe Ala Glu Gln Glu Ile Pro Leu Arg
1               5                   10                  15

Ala Ile Leu Cys Tyr Arg Asn Thr Ser Ser Ile Cys Ser Asn Glu Gly
            20                  25                  30

Leu Ile Phe Lys Leu Lys Arg Gly Lys Glu Ala Cys Ala Leu Asp Thr
        35                  40                  45

Val Gly Trp Val Gln Arg His Arg Lys Met Leu Arg His Cys Pro Ser
    50                  55                  60

Lys Arg Lys
65

<210> SEQ ID NO 330
<211> LENGTH: 69
<212> TYPE: PRT
<213> ORGANISM: Homo sapiens

<400> SEQUENCE: 330

Pro Ile Thr Cys Cys Phe Asn Val Ile Asn Arg Lys Ile Pro Ile Gln
1               5                   10                  15

Arg Leu Glu Ser Tyr Thr Arg Ile Thr Asn Ile Gln Cys Pro Lys Glu
            20                  25                  30

Ala Val Ile Phe Lys Thr Lys Arg Gly Lys Glu Val Cys Ala Asp Pro
        35                  40                  45

Lys Glu Arg Trp Val Arg Asp Ser Met Lys His Leu Asp Gln Ile Phe
    50                  55                  60

Gln Asn Leu Lys Pro
65

<210> SEQ ID NO 331
<211> LENGTH: 68
<212> TYPE: PRT
<213> ORGANISM: Homo sapiens

<400> SEQUENCE: 331

Pro Ser Thr Cys Cys Phe Thr Phe Ser Ser Lys Lys Ile Ser Leu Gln
1               5                   10                  15

Arg Leu Lys Ser Tyr Val Ile Thr Thr Ser Arg Cys Pro Gln Lys Ala
            20                  25                  30

Val Ile Phe Arg Thr Lys Leu Gly Lys Glu Ile Cys Ala Asp Pro Lys
        35                  40                  45

Glu Lys Trp Val Gln Asn Tyr Met Lys His Leu Gly Arg Lys Ala His
    50                  55                  60

Thr Leu Lys Thr
65

<210> SEQ ID NO 332
<211> LENGTH: 61
<212> TYPE: PRT
<213> ORGANISM: Homo sapiens

<400> SEQUENCE: 332

Ser Glu Cys Cys Phe Thr Tyr Thr Thr Tyr Lys Ile Pro Arg Gln Arg
1               5                   10                  15

```
Ile Met Asp Tyr Tyr Glu Thr Asn Ser Gln Cys Ser Lys Pro Gly Ile
            20                  25                  30

Val Phe Ile Thr Lys Arg Gly His Ser Val Cys Thr Asn Arg Ser Asp
            35                  40                  45

Lys Trp Val Gln Asp Tyr Ile Lys Asp Met Lys Glu Asn
    50                  55                  60

<210> SEQ ID NO 333
<211> LENGTH: 67
<212> TYPE: PRT
<213> ORGANISM: Homo sapiens

<400> SEQUENCE: 333

Phe His Phe Ala Ala Asp Cys Cys Thr Ser Tyr Ile Ser Gln Ser Ile
1               5                   10                  15

Pro Cys Ser Leu Met Lys Ser Tyr Phe Glu Thr Ser Ser Glu Cys Ser
            20                  25                  30

Lys Pro Gly Val Ile Phe Leu Thr Lys Lys Gly Arg Gln Val Cys Ala
            35                  40                  45

Lys Pro Ser Gly Pro Gly Val Gln Asp Cys Met Lys Lys Leu Lys Pro
            50                  55                  60

Tyr Ser Ile
65

<210> SEQ ID NO 334
<211> LENGTH: 64
<212> TYPE: PRT
<213> ORGANISM: Homo sapiens

<400> SEQUENCE: 334

Arg Glu Cys Cys Leu Glu Tyr Phe Lys Gly Ala Ile Pro Leu Arg Lys
1               5                   10                  15

Leu Lys Thr Trp Tyr Gln Thr Ser Glu Asp Cys Ser Arg Asp Ala Ile
            20                  25                  30

Val Phe Val Thr Val Gln Gly Arg Ala Ile Cys Ser Asp Pro Asn Asn
            35                  40                  45

Lys Arg Val Lys Asn Ala Val Lys Tyr Leu Gln Ser Leu Glu Arg Ser
    50                  55                  60

<210> SEQ ID NO 335
<211> LENGTH: 62
<212> TYPE: PRT
<213> ORGANISM: Homo sapiens

<400> SEQUENCE: 335

Glu Leu Cys Cys Leu Val Tyr Thr Ser Trp Gln Ile Pro Gln Lys Phe
1               5                   10                  15

Ile Val Asp Tyr Ser Glu Thr Ser Pro Gln Cys Pro Lys Pro Gly Val
            20                  25                  30

Ile Leu Leu Thr Lys Arg Gly Arg Gln Ile Cys Ala Asp Pro Asn Lys
            35                  40                  45

Lys Trp Val Gln Lys Tyr Ile Ser Asp Leu Lys Leu Asn Ala
    50                  55                  60

<210> SEQ ID NO 336
<211> LENGTH: 72
<212> TYPE: PRT
<213> ORGANISM: Homo sapiens

<400> SEQUENCE: 336
```

```
Glu Asp Cys Cys Leu Ser Val Thr Gln Lys Pro Ile Pro Gly Tyr Ile
1               5                   10                  15

Val Arg Asn Phe His Tyr Leu Leu Ile Lys Asp Gly Cys Arg Val Pro
            20                  25                  30

Ala Val Val Phe Thr Thr Leu Arg Gly Arg Gln Leu Cys Ala Pro Pro
            35                  40                  45

Asp Gln Pro Trp Val Glu Arg Ile Ile Gln Arg Leu Gln Arg Thr Ser
        50                  55                  60

Ala Lys Met Lys Arg Ser Ser
65                  70

<210> SEQ ID NO 337
<211> LENGTH: 74
<212> TYPE: PRT
<213> ORGANISM: Homo sapiens

<400> SEQUENCE: 337

Phe His Ala Thr Ser Ala Asp Cys Cys Ile Ser Tyr Thr Pro Arg Ser
1               5                   10                  15

Ile Pro Cys Ser Leu Leu Glu Ser Tyr Phe Glu Thr Asn Ser Glu Cys
            20                  25                  30

Ser Lys Pro Gly Val Ile Phe Leu Thr Lys Lys Gly Arg Arg Phe Cys
            35                  40                  45

Ala Asn Pro Ser Asp Lys Gln Val Gln Val Cys Val Arg Met Leu Lys
        50                  55                  60

Leu Asp Thr Arg Ile Lys Thr Arg Lys Asn
65                  70

<210> SEQ ID NO 338
<211> LENGTH: 70
<212> TYPE: PRT
<213> ORGANISM: Homo sapiens

<400> SEQUENCE: 338

Ser Pro Cys Cys Met Phe Phe Val Ser Lys Arg Ile Pro Glu Asn Arg
1               5                   10                  15

Val Val Ser Tyr Gln Leu Ser Ser Arg Ser Thr Cys Leu Lys Ala Gly
            20                  25                  30

Val Ile Phe Thr Thr Lys Lys Gly Gln Gln Phe Cys Gly Asp Pro Lys
            35                  40                  45

Gln Glu Trp Val Gln Arg Tyr Met Lys Asn Leu Asp Ala Lys Gln Lys
        50                  55                  60

Lys Ala Ser Pro Arg Ala
65                  70

<210> SEQ ID NO 339
<211> LENGTH: 76
<212> TYPE: PRT
<213> ORGANISM: Homo sapiens

<400> SEQUENCE: 339

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
            35                  40                  45

Lys Glu Ile Cys Ala Asp Pro Lys Gln Lys Trp Val Gln Asp Ser Met
        50                  55                  60
```

Asp His Leu Asp Lys Gln Thr Gln Thr Pro Lys Thr
65                  70                  75

<210> SEQ ID NO 340
<211> LENGTH: 62
<212> TYPE: PRT
<213> ORGANISM: Homo sapiens

<400> SEQUENCE: 340

Thr Ala Cys Cys Phe Ser Tyr Thr Ser Arg Gln Ile Pro Gln Asn Phe
1               5                   10                  15

Ile Ala Asp Tyr Phe Glu Thr Ser Ser Gln Cys Ser Lys Pro Gly Val
            20                  25                  30

Ile Phe Leu Thr Lys Arg Ser Arg Gln Val Cys Ala Asp Pro Ser Glu
        35                  40                  45

Glu Trp Val Gln Lys Tyr Val Ser Asp Leu Glu Leu Ser Ala
50                  55                  60

<210> SEQ ID NO 341
<211> LENGTH: 61
<212> TYPE: PRT
<213> ORGANISM: Homo sapiens

<400> SEQUENCE: 341

Thr Ala Cys Cys Phe Ser Tyr Thr Ala Arg Lys Leu Pro Arg Asn Phe
1               5                   10                  15

Val Val Asp Tyr Tyr Glu Thr Ser Ser Leu Cys Ser Gln Pro Ala Val
            20                  25                  30

Val Phe Gln Thr Lys Arg Ser Lys Gln Val Cys Ala Asp Pro Ser Glu
        35                  40                  45

Ser Trp Val Gln Glu Tyr Val Tyr Asp Leu Glu Leu Asn
50                  55                  60

<210> SEQ ID NO 342
<211> LENGTH: 68
<212> TYPE: PRT
<213> ORGANISM: Homo sapiens

<400> SEQUENCE: 342

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
50                  55                  60

Leu Glu Met Ser
65

<210> SEQ ID NO 343
<211> LENGTH: 69
<212> TYPE: PRT
<213> ORGANISM: Homo sapiens

<400> SEQUENCE: 343

Ser Thr Thr Cys Cys Tyr Arg Phe Ile Asn Lys Lys Ile Pro Lys Gln
1               5                   10                  15

Arg Leu Glu Ser Tyr Arg Arg Thr Thr Ser Ser His Cys Pro Arg Glu
            20                  25                  30

```
Ala Val Ile Phe Lys Thr Lys Leu Asp Lys Glu Ile Cys Ala Asp Pro
            35                  40                  45

Thr Gln Lys Trp Val Gln Asp Phe Met Lys His Leu Asp Lys Lys Thr
        50                  55                  60

Gln Thr Pro Lys Leu
65

<210> SEQ ID NO 344
<211> LENGTH: 69
<212> TYPE: PRT
<213> ORGANISM: Homo sapiens

<400> SEQUENCE: 344

Pro Thr Thr Cys Cys Phe Asn Leu Ala Asn Arg Lys Ile Pro Leu Gln
1               5                   10                  15

Arg Leu Glu Ser Tyr Arg Arg Ile Thr Ser Gly Lys Cys Pro Gln Lys
            20                  25                  30

Ala Val Ile Phe Lys Thr Lys Leu Ala Lys Asp Ile Cys Ala Asp Pro
            35                  40                  45

Lys Lys Lys Trp Val Gln Asp Ser Met Lys Tyr Leu Asp Gln Lys Ser
        50                  55                  60

Pro Thr Pro Lys Pro
65

<210> SEQ ID NO 345
<211> LENGTH: 68
<212> TYPE: PRT
<213> ORGANISM: Homo sapiens

<400> SEQUENCE: 345

Ser Thr Cys Cys Leu Lys Tyr Tyr Glu Lys Val Leu Pro Arg Arg Leu
1               5                   10                  15

Val Val Gly Tyr Arg Lys Ala Leu Asn Cys His Leu Pro Ala Ile Ile
            20                  25                  30

Phe Val Thr Lys Arg Asn Arg Glu Val Cys Thr Asn Pro Asn Asp Asp
            35                  40                  45

Trp Val Gln Glu Tyr Ile Lys Asp Pro Asn Leu Pro Leu Leu Pro Thr
        50                  55                  60

Arg Asn Leu Ser
65

<210> SEQ ID NO 346
<211> LENGTH: 67
<212> TYPE: PRT
<213> ORGANISM: Homo sapiens

<400> SEQUENCE: 346

Phe Asp Cys Cys Leu Gly Tyr Thr Asp Arg Ile Leu His Pro Lys Phe
1               5                   10                  15

Ile Val Gly Phe Thr Arg Gln Leu Ala Asn Glu Gly Cys Asp Ile Asn
            20                  25                  30

Ala Ile Ile Phe His Thr Lys Lys Lys Leu Ser Val Cys Ala Asn Pro
            35                  40                  45

Lys Gln Thr Trp Val Lys Tyr Ile Val Arg Leu Leu Ser Lys Lys Val
        50                  55                  60

Lys Asn Met
65
```

```
<210> SEQ ID NO 347
<211> LENGTH: 73
<212> TYPE: PRT
<213> ORGANISM: Homo sapiens

<400> SEQUENCE: 347

Gln Asp Cys Cys Leu Lys Tyr Ser Gln Arg Lys Ile Pro Ala Lys Val
1               5                   10                  15

Val Arg Ser Tyr Arg Lys Gln Glu Pro Ser Leu Gly Cys Ser Ile Pro
            20                  25                  30

Ala Ile Leu Phe Leu Pro Arg Lys Arg Ser Gln Ala Glu Leu Cys Ala
        35                  40                  45

Asp Pro Lys Glu Leu Trp Val Gln Gln Leu Met Gln His Leu Asp Lys
    50                  55                  60

Thr Pro Ser Pro Gln Lys Pro Ala Gln
65                  70

<210> SEQ ID NO 348
<211> LENGTH: 60
<212> TYPE: PRT
<213> ORGANISM: Homo sapiens

<400> SEQUENCE: 348

Ser Val Cys Cys Arg Asp Tyr Val Arg Tyr Arg Leu Pro Leu Arg Val
1               5                   10                  15

Val Lys His Phe Tyr Trp Thr Ser Asp Ser Cys Pro Arg Pro Gly Val
            20                  25                  30

Val Leu Leu Thr Phe Arg Asp Lys Glu Ile Cys Ala Asp Pro Arg Val
        35                  40                  45

Pro Trp Val Lys Met Ile Leu Asn Lys Leu Ser Gln
    50                  55                  60

<210> SEQ ID NO 349
<211> LENGTH: 75
<212> TYPE: PRT
<213> ORGANISM: Homo sapiens

<400> SEQUENCE: 349

Phe Glu Asp Cys Cys Leu Ala Tyr His Tyr Pro Ile Gly Trp Ala Val
1               5                   10                  15

Leu Arg Arg Ala Trp Thr Tyr Arg Ile Gln Glu Val Ser Gly Ser Cys
            20                  25                  30

Asn Leu Pro Ala Ala Ile Phe Tyr Leu Pro Lys Arg His Arg Lys Val
        35                  40                  45

Cys Gly Asn Pro Lys Ser Arg Glu Val Gln Arg Ala Met Lys Leu Leu
    50                  55                  60

Asp Ala Arg Asn Lys Val Phe Ala Lys Leu His
65                  70                  75

<210> SEQ ID NO 350
<211> LENGTH: 73
<212> TYPE: PRT
<213> ORGANISM: Homo sapiens

<400> SEQUENCE: 350

Thr Ala Cys Cys Thr Gln Leu Tyr Arg Lys Pro Leu Ser Asp Lys Leu
1               5                   10                  15

Leu Arg Lys Val Ile Gln Val Glu Leu Gln Glu Ala Asp Gly Asp Cys
            20                  25                  30

His Leu Gln Ala Phe Val Leu His Leu Ala Gln Arg Ser Ile Cys Ile
```

```
                35                  40                  45

His Pro Gln Asn Pro Ser Leu Ser Gln Trp Phe Glu His Gln Glu Arg
 50                  55                  60

Lys Leu His Gly Thr Leu Pro Lys Leu
 65                  70

<210> SEQ ID NO 351
<211> LENGTH: 72
<212> TYPE: PRT
<213> ORGANISM: Homo sapiens

<400> SEQUENCE: 351

Ser Ser Cys Cys Thr Glu Val Ser His His Ile Ser Arg Arg Leu Leu
 1                5                  10                  15

Glu Arg Val Asn Met Cys Arg Ile Gln Arg Ala Asp Gly Asp Cys Asp
                20                  25                  30

Leu Ala Ala Val Ile Leu His Val Lys Arg Arg Arg Ile Cys Val Ser
                35                  40                  45

Pro His Asn His Thr Val Lys Gln Trp Met Lys Val Gln Ala Ala Lys
 50                  55                  60

Lys Asn Gly Lys Gly Asn Val Cys
 65                  70

<210> SEQ ID NO 352
<211> LENGTH: 19
<212> TYPE: PRT
<213> ORGANISM: Aesculus hippocastanum

<400> SEQUENCE: 352

His Gly Ala Cys His Lys Arg Glu Asn His Trp Lys Cys Phe Cys Tyr
 1                5                  10                  15

Phe Asn Cys

<210> SEQ ID NO 353
<211> LENGTH: 20
<212> TYPE: PRT
<213> ORGANISM: Homo sapiens

<400> SEQUENCE: 353

Cys Ala Asn Thr Glu Ile Ile Val Lys Leu Ser Asp Gly Arg Glu Leu
 1                5                  10                  15

Cys Leu Asp Pro
                20

<210> SEQ ID NO 354
<211> LENGTH: 23
<212> TYPE: PRT
<213> ORGANISM: Homo sapiens

<400> SEQUENCE: 354

Cys Pro Thr Ala Gln Leu Ile Ala Thr Leu Lys Asn Gly Arg Lys Ile
 1                5                  10                  15

Cys Leu Asp Leu Gln Ala Pro
                20

<210> SEQ ID NO 355
<211> LENGTH: 23
<212> TYPE: PRT
<213> ORGANISM: Homo sapiens

<400> SEQUENCE: 355
```

```
Cys Ala Gln Thr Glu Val Ile Ala Thr Leu Lys Asn Gly Arg Lys Ala
1               5                   10                  15

Cys Leu Asn Pro Ala Ser Pro
            20
```

<210> SEQ ID NO 356
<211> LENGTH: 17
<212> TYPE: PRT
<213> ORGANISM: Homo sapiens

<400> SEQUENCE: 356

```
Arg Ala Val Ile Phe Ile Thr Lys Arg Gly Leu Lys Val Cys Ala Asp
1               5                   10                  15

Pro
```

<210> SEQ ID NO 357
<211> LENGTH: 20
<212> TYPE: PRT
<213> ORGANISM: Homo sapiens

<400> SEQUENCE: 357

```
Cys Pro Lys Glu Ala Val Ile Phe Lys Thr Ile Val Ala Lys Glu Ile
1               5                   10                  15

Cys Ala Asp Pro
            20
```

<210> SEQ ID NO 358
<211> LENGTH: 20
<212> TYPE: PRT
<213> ORGANISM: Homo sapiens

<400> SEQUENCE: 358

```
Cys Ser Asn Pro Ala Val Val Phe Val Thr Arg Lys Asn Arg Gln Val
1               5                   10                  15

Cys Ala Asn Pro
            20
```

<210> SEQ ID NO 359
<211> LENGTH: 27
<212> TYPE: PRT
<213> ORGANISM: Artificial Sequence
<220> FEATURE:
<223> OTHER INFORMATION: Synthetic peptide

<400> SEQUENCE: 359

```
Asp Ser Ala Asp Val Lys Glu Leu Ile Lys Lys Trp Glu Lys Gln Val
1               5                   10                  15

Ser Gln Lys Lys Lys Gln Lys Asn Gly Lys Lys
            20                  25
```

<210> SEQ ID NO 360
<211> LENGTH: 16
<212> TYPE: PRT
<213> ORGANISM: Artificial Sequence
<220> FEATURE:
<223> OTHER INFORMATION: Synthetic peptide motif
<220> FEATURE:
<221> NAME/KEY: MOD_RES
<222> LOCATION: (1)..(3)
<223> OTHER INFORMATION: Variable amino acid and this region may
      encompass 1 to 3 residues
<220> FEATURE:
<221> NAME/KEY: MOD_RES
<222> LOCATION: (5)..(5)
<223> OTHER INFORMATION: Variable amino acid
<220> FEATURE:

```
<221> NAME/KEY: MOD_RES
<222> LOCATION: (7)..(15)
<223> OTHER INFORMATION: Variable amino acid and this region may
      encompass 2 to 9 residues

<400> SEQUENCE: 360

Xaa Xaa Xaa Gly Xaa Cys Xaa Xaa Xaa Xaa Xaa Xaa Xaa Xaa Xaa Cys
1               5                   10                  15

<210> SEQ ID NO 361
<211> LENGTH: 22
<212> TYPE: PRT
<213> ORGANISM: Artificial Sequence
<220> FEATURE:
<223> OTHER INFORMATION: Synthetic peptidepeptide motif
<220> FEATURE:
<221> NAME/KEY: MOD_RES
<222> LOCATION: (2)..(14)
<223> OTHER INFORMATION: region may encompass between 10 and 13 variable
      amino acids
<220> FEATURE:
<221> NAME/KEY: MOD_RES
<222> LOCATION: (16)..(18)
<223> OTHER INFORMATION: variable amino acid
<220> FEATURE:
<221> NAME/KEY: MOD_RES
<222> LOCATION: (20)..(21)
<223> OTHER INFORMATION: variable amino acid

<400> SEQUENCE: 361

Cys Xaa Xaa Xaa Xaa Xaa Xaa Xaa Xaa Xaa Xaa Xaa Xaa Xaa Gly Xaa
1               5                   10                  15

Xaa Xaa Cys Xaa Xaa Pro
            20

<210> SEQ ID NO 362
<211> LENGTH: 16
<212> TYPE: PRT
<213> ORGANISM: Artificial Sequence
<220> FEATURE:
<223> OTHER INFORMATION: Synthetic peptidepeptide motif
<220> FEATURE:
<221> NAME/KEY: MOD_RES
<222> LOCATION: (2)..(10)
<223> OTHER INFORMATION: region may encompass between 3 and 9 variable
      amino acids
<220> FEATURE:
<221> NAME/KEY: MOD_RES
<222> LOCATION: (12)..(12)
<223> OTHER INFORMATION: variable amino acid
<220> FEATURE:
<221> NAME/KEY: MOD_RES
<222> LOCATION: (14)..(16)
<223> OTHER INFORMATION: region may encompass between 1 and 3 variable
      amino acids

<400> SEQUENCE: 362

Cys Xaa Xaa Xaa Xaa Xaa Xaa Xaa Xaa Xaa Cys Xaa Gly Xaa Xaa Xaa
1               5                   10                  15

<210> SEQ ID NO 363
<211> LENGTH: 16
<212> TYPE: PRT
<213> ORGANISM: Artificial Sequence
<220> FEATURE:
<223> OTHER INFORMATION: Synthetic peptidepeptide motif
<220> FEATURE:
<221> NAME/KEY: MOD_RES
<222> LOCATION: (2)..(10)
<223> OTHER INFORMATION: region may encompass between 3 and 9 variable
      amino acids
<220> FEATURE:
<221> NAME/KEY: MOD_RES
```

```
<222> LOCATION: (12)..(12)
<223> OTHER INFORMATION: variable amino acid
<220> FEATURE:
<221> NAME/KEY: MOD_RES
<222> LOCATION: (14)..(16)
<223> OTHER INFORMATION: region may encompass between 1 and 3 variable
      amino acids

<400> SEQUENCE: 363

Cys Xaa Xaa Xaa Xaa Xaa Xaa Xaa Xaa Xaa Gly Xaa Cys Xaa Xaa Xaa
1               5                   10                  15

<210> SEQ ID NO 364
<211> LENGTH: 19
<212> TYPE: PRT
<213> ORGANISM: Artificial Sequence
<220> FEATURE:
<223> OTHER INFORMATION: Synthetic peptidepeptide motif
<220> FEATURE:
<221> NAME/KEY: MOD_RES
<222> LOCATION: (1)..(11)
<223> OTHER INFORMATION: region may encompass between 8 and 11 variable
      amino acids
<220> FEATURE:
<221> NAME/KEY: MOD_RES
<222> LOCATION: (13)..(15)
<223> OTHER INFORMATION: variable amino acid
<220> FEATURE:
<221> NAME/KEY: MOD_RES
<222> LOCATION: (17)..(18)
<223> OTHER INFORMATION: variable amino acid

<400> SEQUENCE: 364

Xaa Xaa Xaa Xaa Xaa Xaa Xaa Xaa Xaa Xaa Xaa Gly Xaa Xaa Xaa Cys
1               5                   10                  15

Xaa Xaa Pro
```